(12) United States Patent
Puskas

(10) Patent No.: US 10,857,282 B2
(45) Date of Patent: Dec. 8, 2020

(54) SYSTEMS AND METHODS FOR IMPLODING LEUKEMIA CELLS

(71) Applicant: William L. Puskas, New London, NH (US)

(72) Inventor: William L. Puskas, New London, NH (US)

( * ) Notice: Subject to any disclaimer, the term of this patent is extended or adjusted under 35 U.S.C. 154(b) by 296 days.

(21) Appl. No.: 15/771,375

(22) PCT Filed: May 10, 2016

(86) PCT No.: PCT/US2016/031677
§ 371 (c)(1),
(2) Date: Apr. 26, 2018

(87) PCT Pub. No.: WO2017/074509
PCT Pub. Date: May 4, 2017

(65) Prior Publication Data
US 2018/0361052 A1 Dec. 20, 2018

Related U.S. Application Data

(63) Continuation-in-part of application No. 14/923,206, filed on Oct. 26, 2015, now Pat. No. 10,201,651,
(Continued)

(51) Int. Cl.
*A61M 1/36* (2006.01)
*C12N 13/00* (2006.01)
(Continued)

(52) U.S. Cl.
CPC ............ *A61M 1/3678* (2014.02); *A61M 1/36* (2013.01); *A61M 1/3621* (2013.01); *A61M 1/38* (2013.01);
(Continued)

(58) Field of Classification Search
CPC ........ A61M 1/36; A61M 1/3621; A61M 1/38; A61M 2205/3375
See application file for complete search history.

(56) References Cited

U.S. PATENT DOCUMENTS

| 4,315,514 A | 2/1982 | Drewes et al. |
| 4,322,008 A | 3/1982 | Schneider |

(Continued)

FOREIGN PATENT DOCUMENTS

| WO | 2005042178 | 5/2005 |

OTHER PUBLICATIONS

Data, S., et al., Ultrasound-Enhanced Thrombolysis Using Definity as a Cavitation Nucleation Agent, Ultrasound in Medicine & Biology, 2008, vol. 34, No. 9, pp. 1421-1433.
(Continued)

*Primary Examiner* — Leslie R Deak
(74) *Attorney, Agent, or Firm* — Lathrop GPM LLP

(57) ABSTRACT

A system for imploding leukemia cells of a patient includes (a) a first vessel for containing a volume of blood received from the patient, and (b) drive circuitry cooperatively coupled with at least one transducer to produce ultrasound energy that spatially decoheres and disperses throughout the volume, to implode the leukemia cells throughout the volume via absorption of the ultrasound energy by the leukemia cells. The transducer may be an immersible transducer configured to be immersed in the blood. The system may include a second vessel for containing a liquid, within which the ultrasound energy is decohered and dispersed and from which at least a portion of the ultrasound energy is transmitted to the first vessel to implode the leukemia cells.

4 Claims, 24 Drawing Sheets

Related U.S. Application Data which is a continuation of application No. 13/961,832, filed on Aug. 7, 2013, now Pat. No. 9,675,747.

(60) Provisional application No. 61/786,827, filed on Mar. 15, 2013.

(51) Int. Cl.
  A61M 1/38 (2006.01)
  C12N 1/06 (2006.01)

(52) U.S. Cl.
  CPC ............. C12N 1/066 (2013.01); C12N 13/00 (2013.01); *A61M 2205/3375* (2013.01)

(56) References Cited

U.S. PATENT DOCUMENTS

| | | | |
|---|---|---|---|
| 5,401,237 | A | 3/1995 | Tachibana et al. |
| 5,523,058 | A | 6/1996 | Umemura et al. |
| 6,156,549 | A | 12/2000 | Drewes |
| 6,433,460 | B1 | 8/2002 | Puskas |
| 6,538,360 | B2 | 3/2003 | Laugham et al. |
| 8,518,681 | B2 | 8/2013 | Schafer |
| 9,675,747 | B2 | 6/2017 | Puskas |
| 2002/0171331 | A1 | 11/2002 | Puskas |
| 2004/0087879 | A1 | 5/2004 | Mitragotri et al. |
| 2006/0058707 | A1 | 3/2006 | Barthe et al. |
| 2007/0205695 | A1 | 9/2007 | Puskas |
| 2010/0011845 | A1 | 1/2010 | Laugham et al. |
| 2013/0131432 | A1 | 5/2013 | Kline |

OTHER PUBLICATIONS

Miller, D. L., et al., Lithotripter Shock Waves with Cavitation Nucleation Agents Produce Tumor Growth Reduction and Gene Transfer in Vivo, Ultrasound in Medicine & Biology, 2002, vol. 28, No. 10, pp. 1343-1348.

Xu, Z., et al., "A New Strategy to Enhance Cavitational Tissue Erosion Using a High-Intensity, Initiating Sequence," Ultrasonics, Ferroelectrics and Frequency Control, IEEE Transactions, 2006, vol. 53, No. 8, pp. 1412-1424.

PCT Patent Application PCT/US2014/027073 International Search Report and Written Opinion dated Jul. 25, 2014, 11 pages.

U.S. Appl. No. 13/961,832 Office Action dated Apr. 18, 2014, 19 pages.

U.S. Appl. No. 13/961,832 Final Office Action dated Sep. 11, 2014, 14 pages.

U.S. Appl. No. 13/961,832 Office Action dated Mar. 18, 2015, 12 pages.

U.S. Appl. No. 13/961,832 Final Office Action dated Sep. 28, 2015, 12 pages.

U.S. Appl. No. 13/961,832 Office Action dated Jan. 13, 2016, 11 pages.

International Search Report and Written Opinion corresponding to International Patent Application No. PCT/US2016/031677, dated Aug. 12, 2016, 14 pages.

Appeal Brief corresponding to U.S. Appl. No. 13/961,832, filed Jun. 13, 2016, 19 pages.

Decision on Appeal corresponding to U.S. Appl. No. 13/961,832, dated Dec. 27, 2016, 8 pages.

Examiner's Answer corresponding to U.S. Appl. No. 13/961,832, dated Aug. 4, 2016, 11 pages.

Notice of Allowance corresponding to U.S. Appl. No. 13/961,832, dated Mar. 23, 2017, 7 pages.

Notice of Panel Decision from Pre-Appeal Brief Review corresponding to U.S. Appl. No. 13/961,832, dated Apr. 28, 2016, 2 pages.

Pre-Appeal Brief Request for Review corresponding to U.S. Appl. No. 13/961,832, filed Aug. 7, 2013, 8 pages.

Reply Brief corresponding to U.S. Appl. No. 13/961,832, filed Oct. 4, 2016, 18 pages.

Final Rejection corresponding to U.S. Appl. No. 14/754,374, dated Oct. 6, 2017, 14 pp.

Non-Final Rejection corresponding to U.S. Appl. No. 14/923,206, dated Jul. 24, 2018, 8 pp.

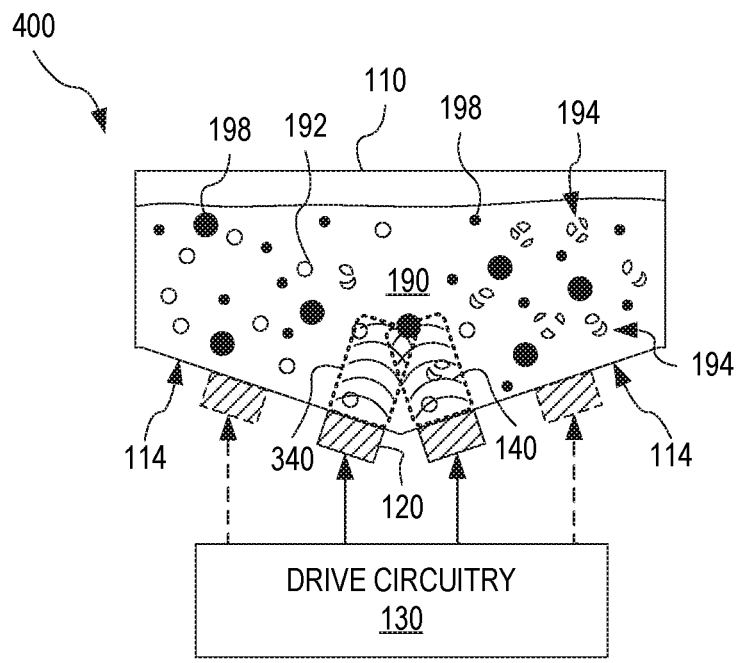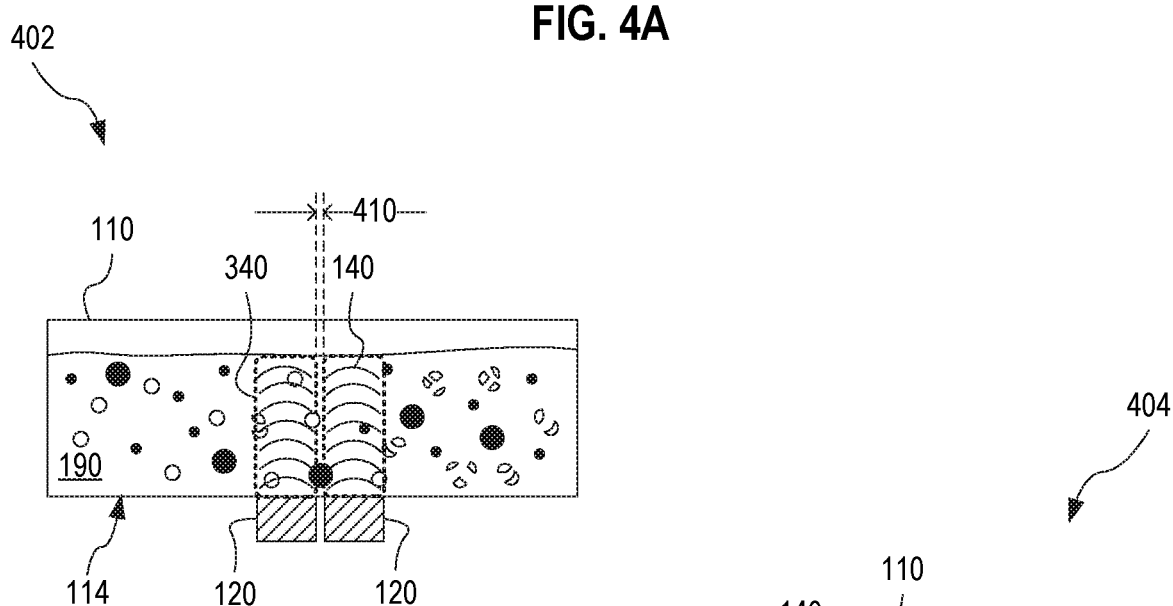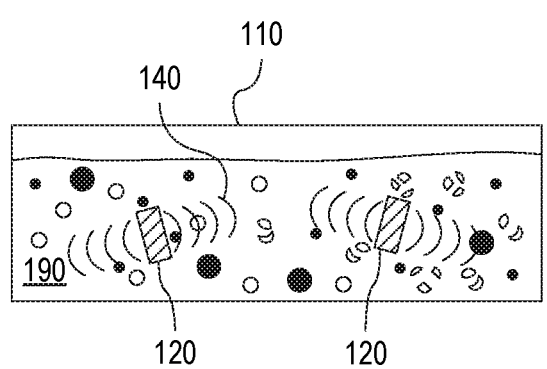
FIG. 4A
FIG. 4B
FIG. 4C

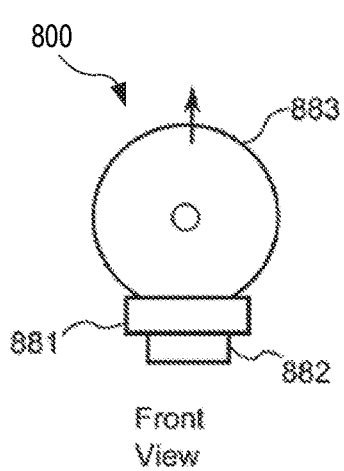
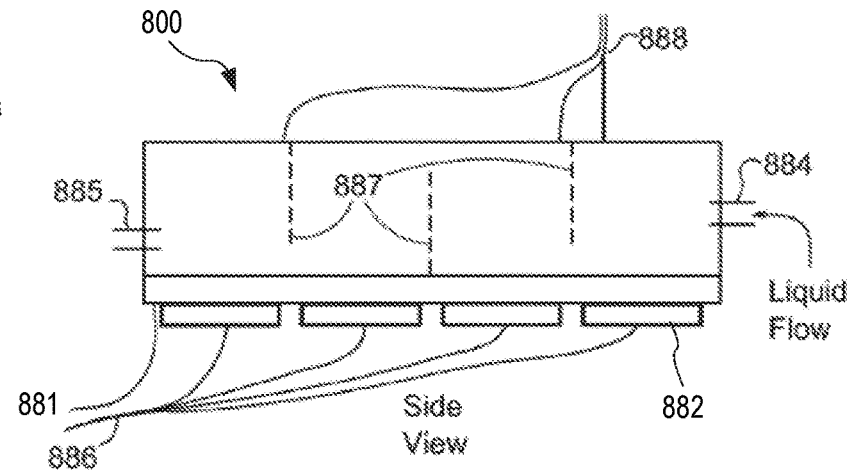
FIG. 8A
FIG. 8B
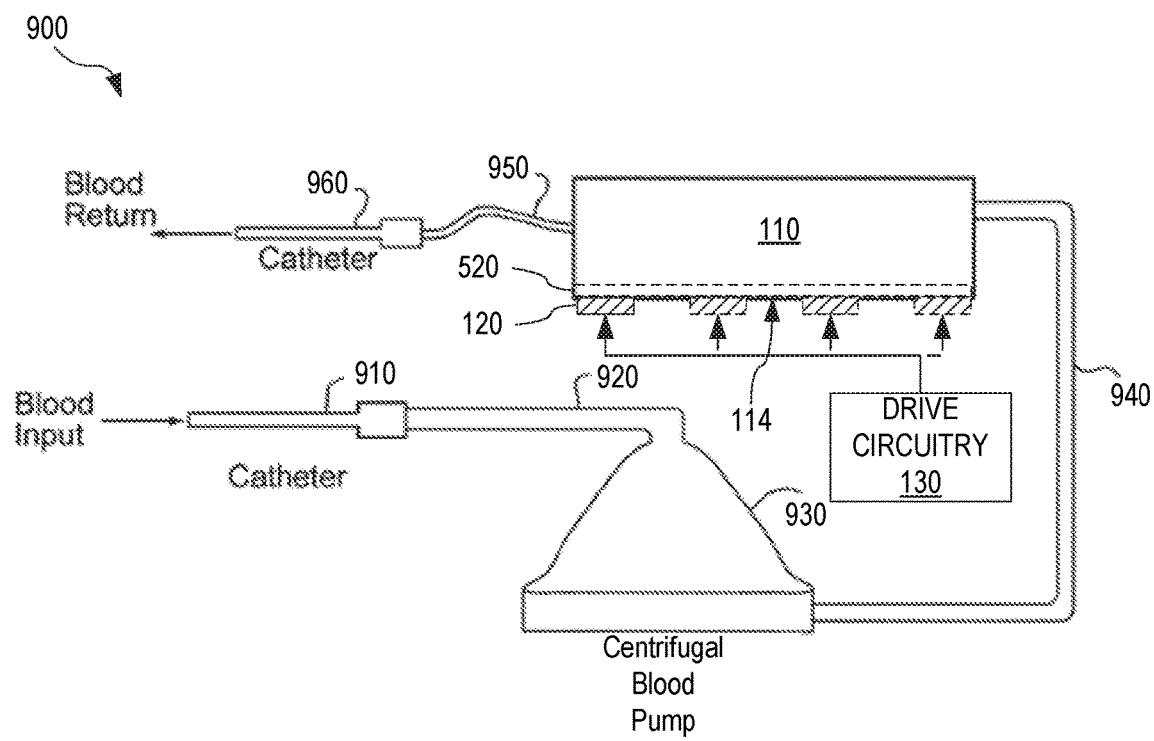
FIG. 9

SYSTEMS AND METHODS FOR IMPLODING LEUKEMIA CELLS

CROSS-REFERENCE TO RELATED APPLICATIONS

This application is a continuation in part of U.S. patent application Ser. No. 14/923,206, filed Oct. 26, 2015, which is a continuation of U.S. patent application Ser. No. 13/961,832, filed Aug. 7, 2013, which claims priority of U.S. Provisional Patent Application No. 61/786,827, filed Mar. 15, 2013. All of the aforementioned references are incorporated herein by reference in their entireties.

BACKGROUND

Leukemia is a form of blood cancer. In a patient with leukemia, cancerous blood cells form. This typically results in high numbers of abnormal white blood cells. These cells are not fully developed and are known as blasts or leukemia cells. Leukemia is a very serious illness with a high mortality rate. Leukemia is widespread and affects all ages. Statistics show that approximately 1.5% of the United States population will be diagnosed with leukemia during their lifetime. Only about 60% of patients diagnosed with leukemia are still alive 5 years after having been diagnosed. Most forms of leukemia are treated with pharmaceutical medication, typically in the form of a multi-drug chemotherapy regimen. Some forms of leukemia are also treated with radiation therapy. In some cases, the patient receives a bone marrow transplant.

SUMMARY

In an embodiment, a system for imploding leukemia cells of a patient includes a first vessel for containing a volume of blood received from the patient. The system further includes drive circuitry cooperatively coupled with at least one transducer to produce ultrasound energy that spatially decoheres and disperses throughout the volume, so as to implode the leukemia cells throughout the volume via absorption of the ultrasound energy by the leukemia cells.

In an embodiment, a system for imploding leukemia cells of a patient includes a first vessel for containing a volume of blood received from the patient. The system further includes drive circuitry coupled with at least one immersible transducer. Each immersible transducer is configured to be immersed in blood within the first vessel. The drive circuitry and the at least one immersible transducer are cooperatively configured to produce ultrasound energy that spatially decoheres and disperses throughout the volume and implodes leukemia cells throughout the volume via absorption of the ultrasound energy by the leukemia cells.

In an embodiment, a system for imploding leukemia cells of a patient includes an outer vessel for containing a liquid permitting spatial decoherence and dispersion of ultrasound energy delivered to the liquid and at least one transducer coupled to an outer surface of the outer vessel. The system further includes drive circuitry cooperatively coupled with the transducer to produce ultrasound energy that spatially decoheres and disperses as incoherent ultrasound energy throughout the liquid. The system also includes an inner vessel having an inlet for receiving blood, an outlet for removing the blood, and a plurality of baffles configured to extend flow path of the blood between the inlet and the outlet. Furthermore, the system includes a pump for circulating blood out of the patient through the inner vessel, via the inlet and the outlet, and back to the patient. When the inner vessel is in contact with the liquid and the blood passes through the inner vessel, the leukemia cells in the blood are imploded via absorption of a portion of the incoherent ultrasound transmitted from the liquid to the blood and dispersed throughout the blood within the inner vessel.

BRIEF DESCRIPTION OF THE DRAWINGS

FIGS. 4A-C illustrate systems for imploding leukemia cells of a patient, which utilize coupling between two or more beams of sound energy to decohere the sound energy and disperse the sound energy to the entire volume of blood within a vessel, according to an embodiment.

FIGS. 8A and 8B illustrate a system for imploding leukemia cells of a patient using sound energy having a sweeping frequency, according to an embodiment.

FIG. 9 illustrates another system for circulating blood out of a patient and through a vessel to implode leukemia cells in the blood before returning the blood to the patient, according to an embodiment.

DETAILED DESCRIPTION OF THE EMBODIMENTS

Figure 1:
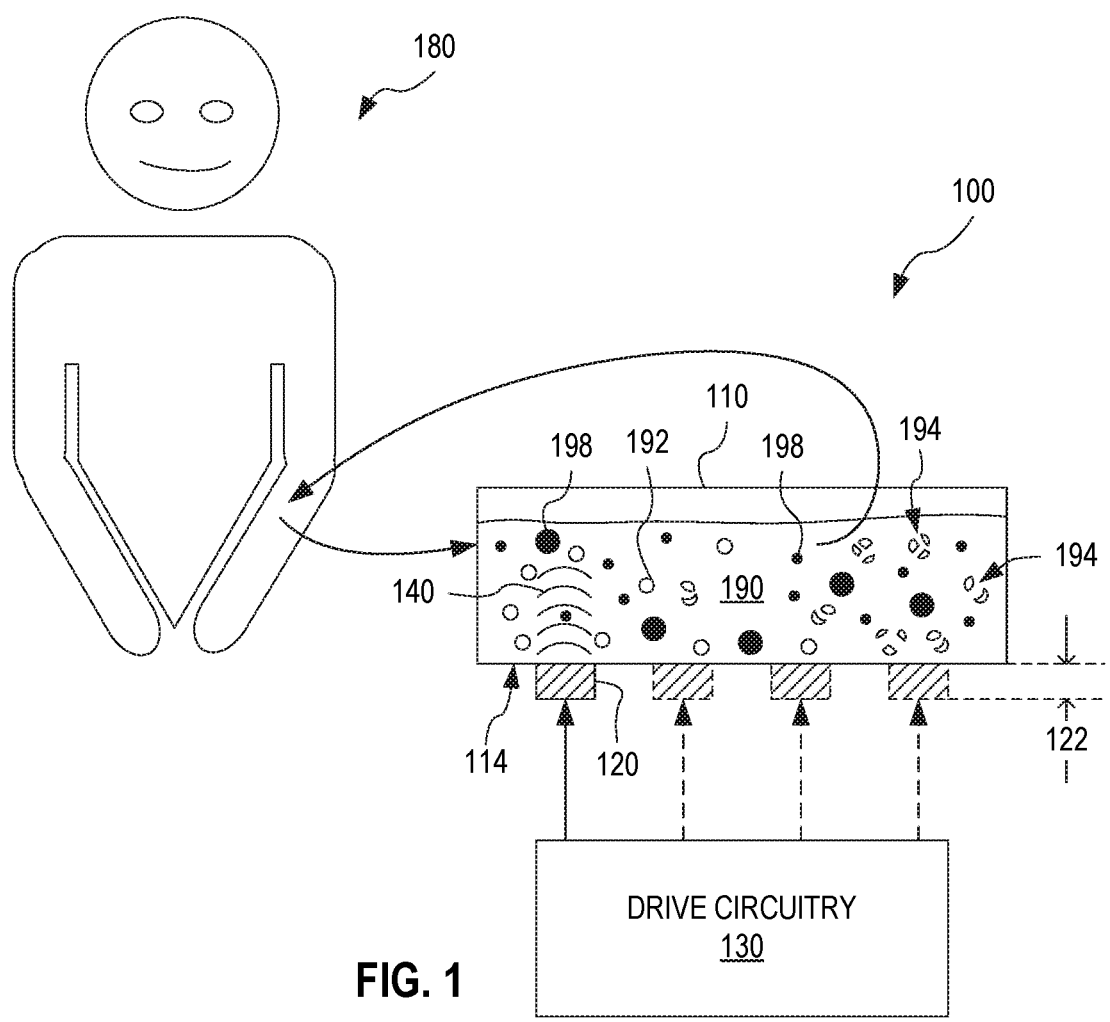
FIG. 1 illustrates a system for imploding leukemia cells of a patient, according to an embodiment.

FIG. 1 illustrates one exemplary system 100 for imploding leukemia cells of a patient. System 100 exposes blood 190 from a patient 180 to sound energy 140 to implode leukemia cells 192 in blood 190. Patient 180 may be a human or a non-human animal. System 100 treats blood 190 in a vessel 110 located externally to patient 180. System 100 exposes blood 190 to sound energy 140 to cause cavitation of leukemia cells 192. In other words, system 100 causes leukemia cells 192 to become cavitation nuclei and implode. Leukemia cells 192 are destroyed by the implosion where leukemia cells 192 break apart in two or more fragments. The frequency of sound energy 140 is resonant with implosion of leukemia cells 192.

Figure 2:
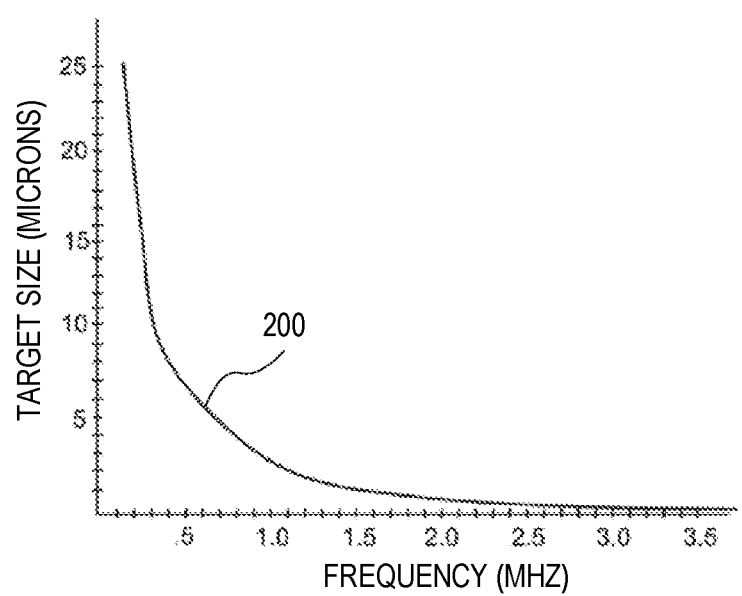
FIG. 2 shows an exemplary correspondence between the size of a target cell and the resonance frequency of sound energy-induced implosion of the target cell.

FIG. 2 shows one exemplary correspondence 200 between the size of a target cell, such as leukemia cell 192, and the resonance frequency for implosion of the target cell by sound energy 140. It is evident that the resonance frequency strongly depends on the size of the target cell. Furthermore, the resonance frequencies associated with typical blood cell sizes, including the size of leukemia cells 192, fall in the ultrasonic frequency range. Herein, the ultrasonic range refers to the range from about 20 kilohertz (kHz) to about 15 megahertz (MHz).

Referring again to FIG. 1, system 100 utilizes that leukemia cells 192 generally have a different size than healthy cells 198, such that sound energy 140 is not resonant with most healthy cells 198 in blood 190. Thus, system 100 is capable of specifically targeting implosion of leukemia cells 192 while leaving other cells, not resonant with sound energy 140, viable. This is of significant benefit to the general health of patient 180. Many conventional chemotherapy treatments have substantial side effects wherein other cells/tissues/organs of patient 180 are harmed by the treatment. However, system 100 acts only on blood 190 of patient 180 and, by virtue of the resonance-driven energy transfer of sound energy 140 to blood 190, leaves all or mostly all healthy cells 198 of blood 190 viable.

In one embodiment, system 100 exposes blood 190 to sound energy 140 in the ultrasonic frequency range.

System 100 includes a vessel 110, one or more transducers 120, and drive circuitry 130. For clarity of illustration, only one transducer 120 is labeled in FIG. 1. Vessel 110 may have shape different from that shown in FIG. 1, without departing from the scope hereof. Vessel 110 receives blood 190 from patient 180. In one exemplary scenario, blood 190 is circulated out of patient 180, through vessel 110, and back into patient 180. The volume capacity of vessel may be in the range from 0.1 to 1.0 liters, such that vessel 110 may hold about 2-20% of the full volume of blood 190 of patient 180. Drive circuitry 130 generates an electric drive signal (e.g., an oscillating voltage) to drive acoustic oscillation of each transducer 120 to produce sound energy 140. For clarity of illustration, sound energy 140 is shown for only one transducer 120. Each transducer 120 may be a piezoelectric transducer that includes a piezoelectric material. The piezoelectric material may be a single piezoelectric layer or a stack of individually driven piezoelectric layers. Optionally, the piezoelectric material is coupled with one or more masses.

In one embodiment, each transducer 120 is a direct-bonded piezoelectric transducer, i.e., configured for generation of sound energy 140 without use of additional masses coupled to the piezoelectric material. The direct-bonded piezoelectric transducer includes electrical connections coupled to the piezoelectric material. Optionally, the direct-bonded piezoelectric transducer further includes other elements of negligible effect on the resonance properties of the transducer disposed therebetween, such as packaging material to electrically isolate the transducer from its environment. This embodiment is particularly well-suited for generating sound energy 140 in the frequency range between 100 kHz and 15 MHz.

In another embodiment, each transducer 120 is a Langevin transducer, wherein the piezoelectric material is placed between two masses. In one example of this embodiment, the Langevin transducer is similar to those disclosed in U.S. Patent Application Serial No. 2007/0080609 which is incorporated herein by reference in its entirety. This embodiment is particularly well-suited for generating sound energy 140 at frequencies below 1 MHz.

In yet another embodiment, system 100 includes at least one direct-bonded piezoelectric transducer and at least one Langevin transducer. This embodiment may allow for efficient generation of sound energy 140 over a wider frequency range than embodiments configured with direct-bonded piezoelectric transducers alone or Langevin transducers alone.

Each transducer 120 is either (a) coupled to a wall of vessel 110 or (b) placed inside vessel 110 such that transducer 120 is fully or partly immersed in blood 190 during operation of system 100. In embodiments wherein a transducer 120 is coupled to a wall of vessel 110, transducer 120 may be coupled directly or indirectly to an outside surface 114 of the wall of vessel 110.

In certain embodiments, each transducer 120 is configured to resonantly oscillate at the resonance frequency for imploding leukemia cells 192, such that the surface of transducer 120 coupled to vessel 110 forms an antinode when operating transducer 120. In one such embodiment, each transducer 120 is a direct-bonded piezoelectric transducer and the thickness 122 of each transducer 120 is an odd integer number of half wavelengths of the sound energy in transducer 120. In one example of this embodiment, transducer 120 is a direct-bonded piezoelectric transducer made of a piezoelectric material PZT-8 and thickness 122 is 5.057 millimeters. This particular value of thickness 122 corresponds to three half-wavelengths of sound energy 140 at a frequency of 1.4 MHz, which propagates through the PZT-8 material at a speed of 4720 meters/second. In a more general example, transducer 120 is a direct-bonded piezoelectric transducer with thickness in the range from about one millimeter to about twelve millimeters. For example, an 11.8 mm thick transducer will produce 200 kHz when driven at one-half wavelength in the PZT-8 material. A 1.101 millimeter thick transducer will produce 15 MHz when driven with seven half wavelengths in the PZT-8 material. In an alternate embodiment, a 1.416 millimeter thick transducer may produce the 15 MHz driven with 9 half wavelengths in PZT-8 material. PZT-8 material thicker than 11.8 mm may be used to produce frequencies below 200 kHz, however, where these lower frequencies are required.

System 100 is configured to decohere and disperse sound energy 140, generated by transducers 120, to substantially the entire volume of blood 190 within vessel 110. In an embodiment, each transducer 120 generates a beam of sound energy 140, and system 100 is configured to disrupt the coherence of such beam(s) to disperse sound energy 140 is to substantially the entire volume of blood 190 within vessel 110. Throughout the present disclosure, a "beam" of sound energy refers to the general direction of sound energy propagating away from the transducer generating the sound energy. It is understood that, in the presence of a mechanism to disrupt the coherence of one or more beams, actual beams may not exist, in which case the term "beam" refers to the direction of the sound energy if the beam had not been disrupted. Herein, "dispersion" of sound energy to a certain volume refers to distribution of the sound energy throughout this volume. Herein, "decoherence" refers to disruption of the coherence of sound energy beams.

Although FIG. 1 shows vessel 110 as only being partly filled with blood 190, vessel 110 may be completely filled with blood 190 without departing from the scope hereof.

By addressing the entire volume of blood 190 within vessel 110, system 100 ensures that it is not possible for leukemia cells 192 to escape exposure to sound energy 140 when inside vessel 110. Thus, system 100 achieves reliable implosion of leukemia cells 192 without the need for diffusion or mixing of blood 190 within vessel 110.

Both Drewes et al. (U.S. Pat. Nos. 6,156,549 and 4,315,514) and Kline (U.S. Patent Application 2013/0131432) discuss treating cancer using ultrasound. Drewes discussed the application of ultrasound to a blood sample from a patient to treat leukemia. However, in contrast to the presently disclosed systems and methods, Drewes et al. does not decohere or disperse the ultrasound to an extended volume. In fact, Drewes et al. focuses ultrasound onto the location of interest. The ultrasound propagates from a transducer through the blood sample to (and through) the focal point but does not destroy leukemia cells in portions of the blood sample away from this focal point. Thus, the technology disclosed by Drewes et al. is not capable of addressing the entire volume of blood sample. Without addressing the entire volume, the treatment cannot successfully destroy all leukemia cells in the blood sample. Kline is concerned with application of ultrasound directly to the patient to locally target neoplastic cells within the patient. This form of treatment does not work for leukemia where the leukemia cells are dispersed throughout the blood of the patient. Kline does not disclose means for decohering or dispersing ultrasound and therefore also fails to provide a method or system suitable for treatment of leukemia. In contrast, since the presently disclosed systems and methods decohere and disperse sound energy to the entire volume of blood within a vessel, the presently disclosed systems and methods may successfully treat leukemia. In U.S. Patent Application 2010/0113983, Heckerman et al. discusses using ultrasound to disrupt pathogens. However, Heckerman does not disclose means for decohering and dispersing ultrasound and therefore also fails to provide a method or system suitable for treatment of leukemia.

As discussed in further detail below, for example in reference to FIGS. 3A-4C, 6, and 25, system 100 may use a variety of methods to efficiently decohere sound energy 140 and disperse sound energy 140 to the entire volume of blood 190 within vessel 110. Efficient decoherence and dispersion of sound energy 140 facilitates implosion of leukemia cells 192 throughout the entire volume of blood 190 within vessel 110 while operating transducers 120 at reasonable power levels. Optionally, blood 190 is conditioned to enhance the decoherence and dispersion of sound energy 140 and/or the rate of implosion of leukemia cells 192. For example, the temperature of blood 190 may be increased above normal body temperature. However, the methods and systems disclosed herein may provide decoherence and dispersion of sound energy 140 at efficiencies that are sufficient to eliminate the need for conditioning of blood 190.

Drive circuitry 130 may drive transducer(s) 120 at a power of about 0.5-10 watts per square centimeter of transducer surface area. In one example, each transducer 120 has a rectangular surface area with dimension 25 to 30 millimeters by 50 to 200 millimeters, and drive circuitry 130 drives each transducer 120 at about 100 watts. The volume of vessel 110 is in the range from 0.1 liters to 1.5 liters, for example. The total surface area of transducer(s) 120 contacting vessel 110 may be about 50 to 240 square centimeters, and transducer(s) 120 may be driven at a total power of 25 to 2400 watts.

Without departing from the scope hereof, vessel 110 may be a portion of a larger vessel, wherein blood 190, intended to be treated, passes through vessel 110 such that system 100 exposes the entire volume of blood 190 to sound energy 140. In one such example, vessel 110 receives blood 190 from a pre-chamber and/or delivers blood 190 to a post-chamber after treatment of blood. Vessel 110 may be integrated with the pre-chamber and/or post-chamber.

In certain embodiments, discussed in further detail below in reference to FIGS. 29-35B, vessel 110 holds a first liquid, such as water, and blood 190 is deposited in an inner vessel that is positioned in contact with the liquid of vessel 110. In these embodiments, sound energy 140 generated by transducer(s) 120 couples via the first liquid into blood 190 deposited in the inner vessel.

Without departing from the scope hereof, system 100 may be used in conjunction with other leukemia treatment methods such as a bone marrow transplant.

Figure 3A:
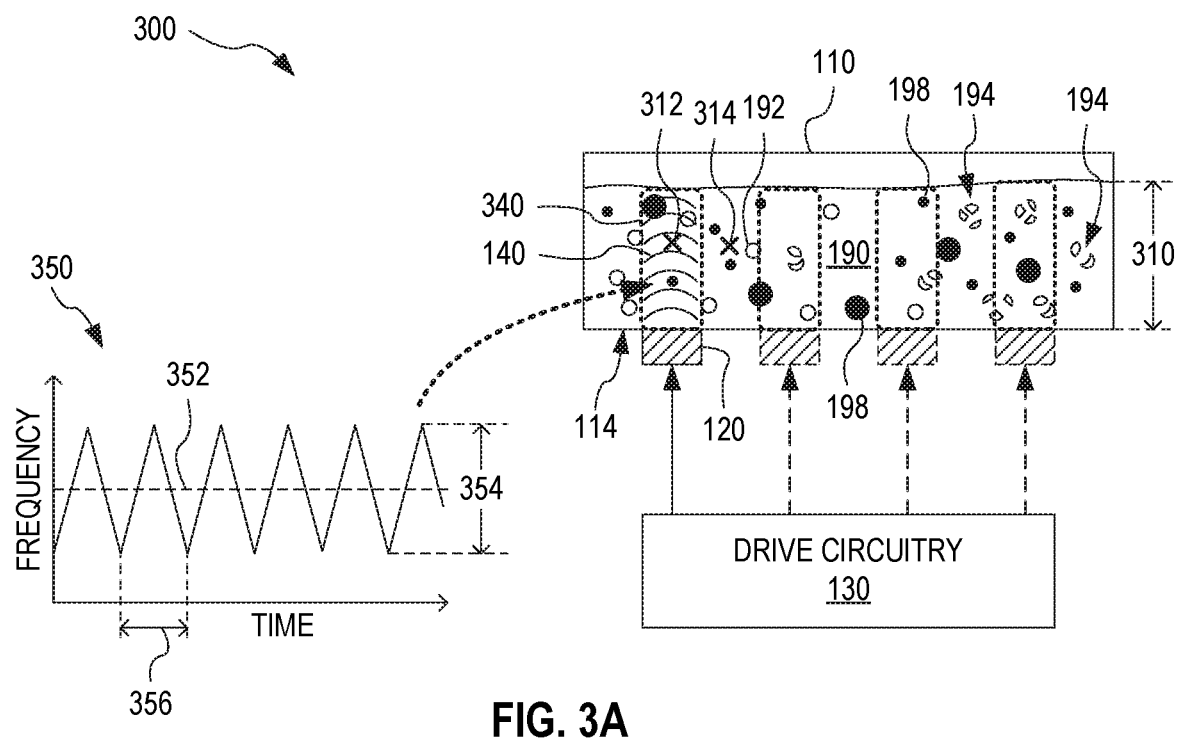
FIGS. 3A and 3B illustrate systems for imploding leukemia cells of a patient, which utilize frequency sweeping of the sound energy to decohere the sound energy and disperse the sound energy to the entire volume of blood within a vessel, according to an embodiment.
Figure 3B:
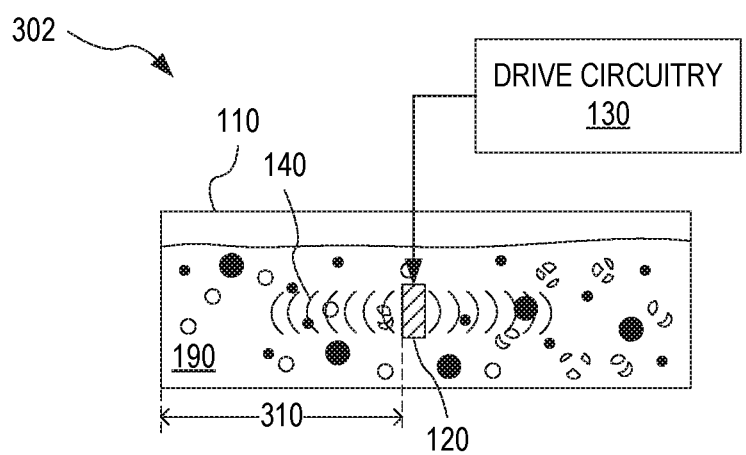

FIGS. 3A and 3B illustrate exemplary systems 300 and 302 for imploding leukemia cells 192 of patient 180, which utilize frequency sweeping of sound energy 140 to decohere sound energy 140 and disperse sound energy 140 to the entire volume of blood 190 within vessel 110. Each of systems 300 and 302 is an embodiment of system 100, wherein drive circuitry 130 is adapted to drive each transducer 120 at a sweeping frequency. FIG. 3A shows system 300. In system 300, each transducer 120 is placed on outside surface 114 of a wall of vessel 110. FIG. 3B shows system 302. In system 302, one or more transducers 120 are located inside vessel 110 to be immersed in blood 190. Although only one transducer 120 is shown in FIG. 3B, several transducers 120 may be immersed in blood 190 inside vessel 110 without departing from the scope hereof. FIGS. 3A and 3B utilize the same mechanism for dispersion of sound energy 140 to the entire volume of blood 190 within vessel 110 and are best viewed together.

As shown in a diagram 350, drive circuitry 130 of both system 300 and system 302 repeatedly sweeps the frequency of sound energy 140 (for clarity of illustration, diagram 350 is depicted in FIG. 3A only, although diagram 350 applies to FIG. 3B as well). In systems 300 and 302, sound energy 140 has a center frequency 352, a frequency bandwidth 354, and a sweep period 356. Center frequency 352 is the same as or near the resonance frequency for implosion of leukemia cells 192. Herein, "bandwidth" refers to the frequency range of sound energy 140. Although diagram 350 shows a triangular sweep pattern, drive circuitry 130 may, without departing from the scope hereof, use a different sweep pattern. For example, drive circuitry 130 may sweep the frequency of sound energy 140 according to a sawtooth pattern, a sinusoidal pattern, a square pattern, random frequency across frequency bandwidth 354, or another pattern known in the art.

Center frequency 352 is in the ultrasonic frequency range, for example. The sweep rate may be in the range from 0.2 kHz/millisecond (kHz/ms) to 100 kHz/ms. Together with frequency bandwidth 354 and the type of sweep pattern, this sweep rate defines sweep period 356.

Each transducer 120 generates sound energy 140 travelling away from transducer 120 in a certain direction. This direction is generally parallel to the dimension associated with material displacement within transducer 120. For example, for a transducer 120 based upon a piezoelectric ceramic, sound energy 140 generally propagates away from transducer 120 in a direction parallel to the dimension associated with thickness oscillation of the piezoelectric ceramic (perpendicular to the plane defined by the interface between transducer 120 and vessel 110). In the absence of frequency sweeping, or other means of coherence disruption, sound energy 140 is mostly confined to a beam 340. However, frequency sweeping of sound energy 140 disrupts the coherence of beam 340 and sound energy 140 is dispersed to the entire volume of blood 190 within vessel 110. For clarity of illustration in FIG. 3A, only one transducer 120 is labeled, only one beam 340 is labeled, and sound energy 140 is shown for only one transducer 120. Also for clarity of illustration, beams 340 are not labeled in FIG. 3B.

In certain embodiments, each transducer 120 is a piezoelectric transducer configured to operate at center frequency 352 in the range from 200 kHz to 15 MHz, and frequency bandwidth 354 is between 0.1 percent and 15 percent of center frequency 352. In one such embodiment, each transducer 120 is a direct-bonded piezoelectric transducer configured to generate sound energy 140 over a frequency bandwidth 354 between 0.1 percent and 7 percent of center frequency 352. In another such embodiment, each transducer is a Langevin transducer configured to generate ultrasound energy 140 over a frequency bandwidth 354 between 2 percent and 15 percent of center frequency 352. Langevin transducers generally have greater bandwidth for efficient generation of sound energy than direct-bonded piezoelectric transducers and may therefore advantageously be implemented in embodiments of systems 300 and 302 intended for generation of sound energy 140 in the frequency range up about 500 kHz or even 1 MHz. For embodiments of system 300/302 requiring a wide range of frequencies, for example spanning from below 200-500 kHz to one or several MHz, system 300/302 may advantageously implement a combination of direct-bonded piezoelectric transducers and Langevin transducers.

In an experimental demonstration, a hydrophone was used to measure the energy density of sound energy 140 to demonstrate sweeping-induced decoherence of sound energy 140 and dispersion of sound energy 140 throughout the entire volume of blood 190 within vessel 110 of system 300. This experiment utilized an embodiment of system 300 having two transducers 120 coupled to outside surface 114 of a wall of vessel 110. Center frequency 352 was 430 kHz, and blood 190 was replaced by water. The energy density was measured in two different scenarios. In one scenario, the sweeping functionality of system 300 was turned off, such that the frequency of sound energy 140 was constant. In this scenario, stable beams 340 formed above each of the two transducers. The hydrophone produced a signal of 42 volts rms (root mean square) at location 312 within beam 340 and a signal of only 3 volts rms at location 314 not in a beam 340. In another scenario, sweeping was applied as shown in diagram 350 with bandwidth 354 set at 5 kHz and sweep period 356 set at 2 ms. In this scenario, beams 340 were disrupted and it was visually clear that sound energy 140 was dispersed to the entire volume of water within vessel 110. The hydrophone produced a signal of 41 volts rms at location 314, thus quantitatively demonstrating dispersion of sound energy 140 to the entire volume of water within vessel 110.

Another experiment demonstrated sweeping-induced dispersion of sound energy 140 throughout the entire volume of blood 190 within vessel 110 of system 302. This experiment utilized an embodiment of system 302 having a single transducer 120 immersed in 300 milliliters of deionized water (simulating blood 190) inside a tubular embodiment of vessel 110. Transducer 120 was driven at 60 watts with center frequency 352 being 440 kHz, sweep period 356 being 2 ms, and frequency bandwidth 354 being 8 kHz. Dispersion of the resulting sound energy 140 to the entire volume of liquid inside vessel 110 was visually apparent.

Without being bound by theory, it is believed that beam 340 is disrupted when sound energy 140 back-reflected toward transducer 120 from the blood-to-air interface (or alternatively the blood-to-solid interface as shown in FIG. 3B or if blood 190 fills vessel 110 in FIG. 3A). That is, reflected sound energy 140 interferes with forward-propagating sound energy 140 propagating from transducer 120 toward the blood-to-air interface (or blood-to-solid interface). The index-of-refraction different between blood 190 and air (or solid) produces nearly 100% back-reflection of sound energy 140. Due to frequency sweeping, back-reflected sound energy 140, which is generated earlier than forward-propagating sound energy 140, is not in phase with forward-propagating sound energy 140. Without frequency sweeping, a standing wave forms between transducer 120 and the blood-to-air interface (or blood-to-solid interface). However, with frequency sweeping, the phase mismatch disrupts this standing wave. As a result, sound energy 140 is dispersed to the entire volume of blood 190 within vessel 110. In an embodiment, sweep period 356, center frequency 352, frequency bandwidth 354, and distance 310 from transducer 120 to the blood-to-air interface (or blood-to-solid interface) cooperate to produce a phase shift, between back-reflected sound energy 140 and forward-propagating sound energy 140 at the midpoint of distance 310, which is at least a fraction of the period of the acoustic oscillation associated with sound energy 140. In one example, this phase shift is at least a quarter of the period of the acoustic oscillation associated with sound energy 140. This theoretical consideration is equally applicable to both system 300 and system 302.

Since each beam 340 is disrupted by its own reflection, each of systems 300 and 302 may function with only a single transducer 120. In one embodiment, system 300 includes only a single transducer 120. In a similar embodiment, system 302 includes only a single transducer 120. In another embodiment, system 300 includes two or more transducers 120. In a similar embodiment, system 302 includes two or more transducers 120. Without departing from the scope hereof, features of systems 300 and 302 may be combined to form a system that includes both one or more transducers 120 mounted to outside surface 114 of a wall of vessel 110 and one or more transducers 120 located within vessel 110 to be immersed in blood 190.

Each of systems 300 and 302, as well as combinations thereof, may further include fluid handling components to circulate blood 190 out of patient 180, through vessel 110, and back into patient 180 after treatment of blood 190 in vessel 110, as discussed below in reference to FIG. 5.

FIGS. 4A-C illustrate exemplary systems 400, 402, and 404 for imploding leukemia cells 192 of patient 180, which utilize coupling between two or more beams 340 of sound energy 140 to decohere sound energy 140 and disperse sound energy 140 to the entire volume of blood 190 within vessel 110. Each of systems 400, 402, and 404 is an embodiment of system 100, which includes at least two transducers 120. FIG. 4A shows system 400, wherein at least two transducers 120 are placed on outside surface 114 of a wall of vessel 110 such that sound energy 140, generated by at least two different transducers 120, spatially overlaps. FIG. 4B shows system 402, wherein at least two transducers 120 are placed on outside surface 114 of a wall of vessel 110 such that distance 420 between respective sound energy beams 340 is sufficiently small for the sound energy beams 340 to couple with each other. FIG. 4C shows system 404, wherein at least two transducers 120 are located inside vessel 110 to be immersed in blood 190. For clarity of illustration, FIGS. 4B and 4C do not show drive circuitry 130, although each of system 402 and 404 includes drive circuitry 130. Without departing from the scope hereof, each of systems 400, 402, and 404 may include more transducers than shown. Systems 400, 402, and 404 utilize the same fundamental mechanism, i.e., coupling between beams 340, to decohere sound energy 140 and disperse sound energy 140 to the entire volume of blood 190 within vessel 110. FIGS. 4A-C are best viewed together.

When a plurality of beams 340 spatially overlap, each of these beams 340 exerts a force on a common portion of blood 190. Thus, blood 190 acts as a medium to introduce coupling between these beams 340. If the force exerted by one beam 340 is in a different direction than the force exerted by at least one other beam 340, the coherence of these beams 340 may be disrupted. Likewise, when a plurality of beams 340 are sufficiently close that the viscosity of blood 190 introduces coupling between the beams 340, difference in direction between forces associated with different beams 340 may disrupt the coherence of the beams 340. System 400 utilizes coupling between two or more beams 340 to disrupt the coherence of these beams 340, which results in the dispersion of sound energy 140 to the entire volume of blood 190 within vessel 110.

In system 400, two transducers 120 direct sound energy 140 in two intersecting directions. Upon turning on transducers 120, transducers 120 generate two beams 340 (the two most central beams 340 shown in FIG. 4A) that intersect at an angle to each other. The movement of blood 190 induced by the left-central beam 340 interferes with the movement of blood 190 induced by the right-central beam 340. As a result, these two beams 340 are disrupted and sound energy 140 is dispersed to the entire volume of blood 190 within vessel 110. Such disruption of beams 340 may also occur after at least one of the beams 340 has been reflected by a blood-to-air or blood-to-solid interface. For example, if included, the leftmost transducer 120 shown in FIG. 4A may generate a beam 340 that couples with one or more other beams 340 after being reflected by the blood-to-air or blood-to-solid interface. For clarity of illustration, not all transducers 120 are labeled in FIG. 4A.

In system 402, two beams 340 are parallel but spaced by a distance 410 sufficiently small that the viscosity of blood 190 couples the two beams 340. Drive circuitry 130 drives one transducer 120 at a different frequency or phase than the other transducer 120 such that the coupling between the two beams 340 disrupts the coherence of beams 340. As a result, sound energy 140 is dispersed to the entire volume of blood 190 within vessel 110. When utilizing different frequencies for the two transducers 120, each frequency is sufficiently close to the resonance frequency for cavitation of leukemia cells 192 to resonantly implode leukemia cells 192.

In system 404, two of more transducers 120 are located inside vessel 110 to be immersed in blood 190. Beams 340 of sound energy 140 from these transducers 120 spatially overlap to disrupt the coherence of beams 340 and disperse sound energy 140 to the entire volume of blood 190 within vessel 110. For clarity of illustration, beams 340 are not labeled in FIG. 4C.

Without departing from the scope hereof, features of two or all of systems 400, 402, and 404 may be combined. In one such embodiment, transducers 120 of system 404 may be configured to generate non-overlapping beams 340 separated only by a short distance, such that beams 340 couple with each other through the viscosity of blood 190 to disrupt the coherence of beams 340 (as discussed in reference to FIG. 4B). In another such embodiment, drive circuitry 130 drives transducers 120 of system 400 (and or transducers 120 of system 404) at different frequencies or phases as discussed in reference to FIG. 4B. Yet another such embodiment includes a combination of two or more of (a) transducers 120 configured as shown in FIG. 4A, (b) transducers 120 configured as shown in FIG. 4B, and (c) transducers 120 configured as shown in FIG. 4C.

Also without departing from the scope hereof, any of systems 400, 402, and 404, as well as combinations thereof, may further include frequency sweeping functionality as discussed above in reference to FIGS. 3A and 3B. Likewise, any of systems 300, 302, and combinations thereof may further include transducers 120 configured to couple with each other as discussed above in reference to FIGS. 4A-C.

Each of systems 400, 402, 404, and combinations thereof may further include fluid handling components to circulate blood 190 out of patient 180, through vessel 110, and back into patient 180 after treatment of blood 190 in vessel 110, as discussed below in reference to FIG. 5.

Figure 5:
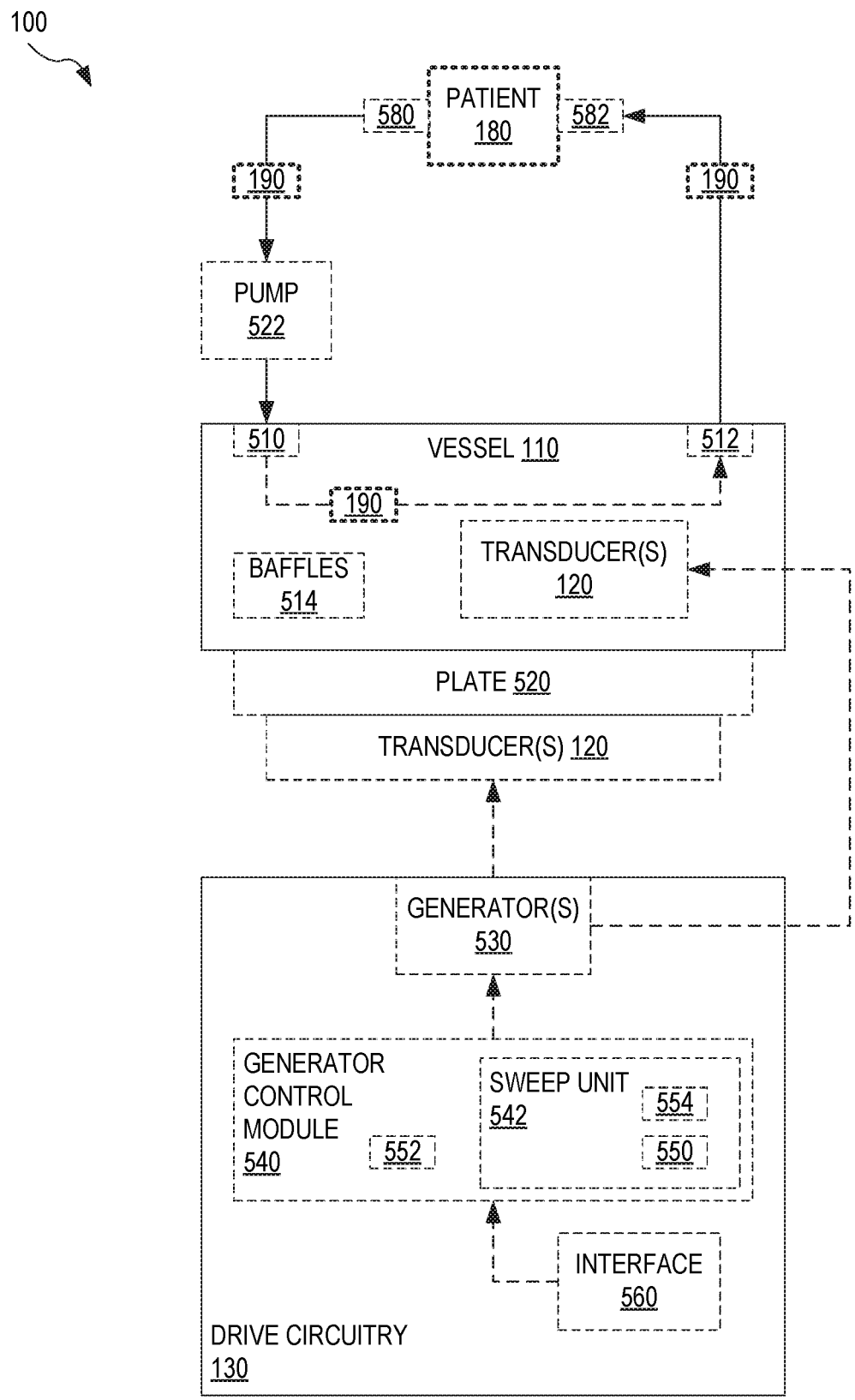
FIG. 5 is a block diagram of the system of FIG. 1, according to an embodiment.

FIG. 5 is a block diagram of system 100. System 100 includes vessel 110 and drive circuitry 130. System 100 further includes (a) one or more transducers 120 mounted to outside surface 114 of a wall of vessel 110 and/or (b) one or more transducers 120 located inside vessel 110 (for clarity of illustration, outside surface 114 is not indicated in FIG. 5). Each transducer 120 is communicatively coupled with drive circuitry 130. Transducers 120 may be configured as discussed above in reference to FIGS. 3A-4C.

In certain embodiments, drive circuitry 130 includes one or more generators 530 and a generator control module 540. Generator control module 540 controls each generator 530 to generate an electrical drive signal that drives one or more transducers 120 to generate sound energy 140. Generator control module 540 includes a frequency setting 552 that defines the frequency of the electrical drive signal(s) generated by generator control module 540. In operation, frequency setting 552 is set to substantially match the resonance frequency for implosion of leukemia cells 192, such that each transducer 120 produces sound energy 140 resonant with implosion of leukemia cells 192. Although not explicitly shown in FIG. 5, blood 190 may include leukemia cells 192. In one embodiment, generator control module 540 includes a sweep unit 542 that repeatedly sweeps the frequency of the drive signal generated by at least one generator 530. Sweep unit 542 includes a frequency bandwidth setting 554 and a sweep pattern setting 550. Frequency bandwidth setting 554 defines frequency bandwidth 354 for the electrical drive signal(s) generated by generator control module 540. Sweep pattern setting 550 defines the sweep pattern of the electrical drive signal(s) generated by generator control module 540, as discussed above in reference to FIGS. 3A and 3B. In operation, frequency bandwidth setting 554 and sweep pattern setting 550 are set to induce decoherence of sound energy 140 and dispersion of sound energy 140 to the entire volume of blood 190 within vessel 110. In embodiments of generator control module 540 that include sweep unit 542, frequency setting 552 defines center frequency 352. Optionally, drive circuitry 130 includes an interface 560. An operator, and/or an external computer system, may communicate frequency setting 552, frequency bandwidth setting 554, and/or sweep pattern setting 550 to generator control module 540 via interface 560. In addition, an operator, and/or an external computer system, may control other functionality of drive circuitry 130 via interface 560, such as turn on and off generator(s) 530.

In an embodiment, system 100 includes fluid handling components to circulate blood 190 through vessel 110. In this embodiment, vessel 110 includes an inlet 510 and an outlet 512. Blood 190 enters vessel 110 via inlet 510 and leaves vessel 110 via outlet 512. Inlet 510 is spaced apart from outlet 512 to at least partly define a flow path of blood 190 through vessel 110. Vessel 110 may include baffles 514 or other obstructions to extend the flow path of blood 190 through vessel 110. System 100 may further include a pump 522 that pumps blood 190 out of patient 180 via a catheter 580, through vessel 110 via inlet 510 and outlet 512, and back into patient 180 via a catheter 582. In a treatment scenario, blood 190 with leukemia cells 192 is extracted from patient 180 via catheter 580. Blood 190 is then treated inside vessel 110, before blood 190 with imploded leukemia cells 192 is returned to patient 180 via catheter 582. Optionally, system 100 includes catheter 580 and catheter 582. Pump 522 is a centrifugal blood pump, for example. System 100 may further include tubing (not shown in FIG. 5) configured to complete the fluidic circuit from catheter 580 through vessel 110 to catheter 582.

In an embodiment, system 100 includes at least one plate 520 and one or more transducers 120 mounted to vessel 110 via plate 520. Plate 520 has a thickness that is an integer number of half wavelengths of sound energy 140 within plate 520, such that sound energy 140 is efficiently coupled from each associated transducer 120 to blood 190. In one implementation, plate 520 is a steel plate. The thickness of this steel plate is, for example, 1, 2, or 3 half wavelengths of sound energy 140 within the steel plate. In one implementation, plate 520 forms a wall of vessel 110. In another implementation, plate 520 is coupled to outside surface 114 of a wall of vessel 110, wherein this wall of vessel 110 has negligible thickness. In an alternative embodiment, plate 520 is mounted to outside surface 114 of a wall of vessel 110, and the combined thickness of this wall and plate 520 is an integer number of half wavelengths of sound energy 140. In yet another alternative embodiment, plate 520 forms a wall of vessel 110, and the thickness of this wall/plate 520 is either near zero or an integer number of half wavelengths of sound energy 140, where near zero refers to a thin plate that is less than 10% of a half wavelength. This "thin plate" embodiment is particularly well suited for use at low frequencies (e.g., at about 500 kHz or less) with transducer(s) 120 of the Langevin style.

Embodiments of system 100 that utilize only transducer(s) 120 located inside vessel, for immersion in blood 190, need not include plate 520. This significantly reduces the combined cost of vessel 110, transducers, and hardware required to mount transducers. In one such embodiment, vessel 110, transducer(s) 120, and associated mounting hardware form a disposable portion of system 100 that is used, for example, to treat blood 190 of only a single patient 180, thus eliminating the need for cleaning and decontamination of this portion of system 100.

Without departing from the scope hereof, vessel 110, transducers 120, and plate 520 (if included), and optionally other mounting hardware may form a stand-alone system configured to operate in conjunction with third party drive circuitry 130 to implode leukemia cells 192 in blood 190.

Figure 6:
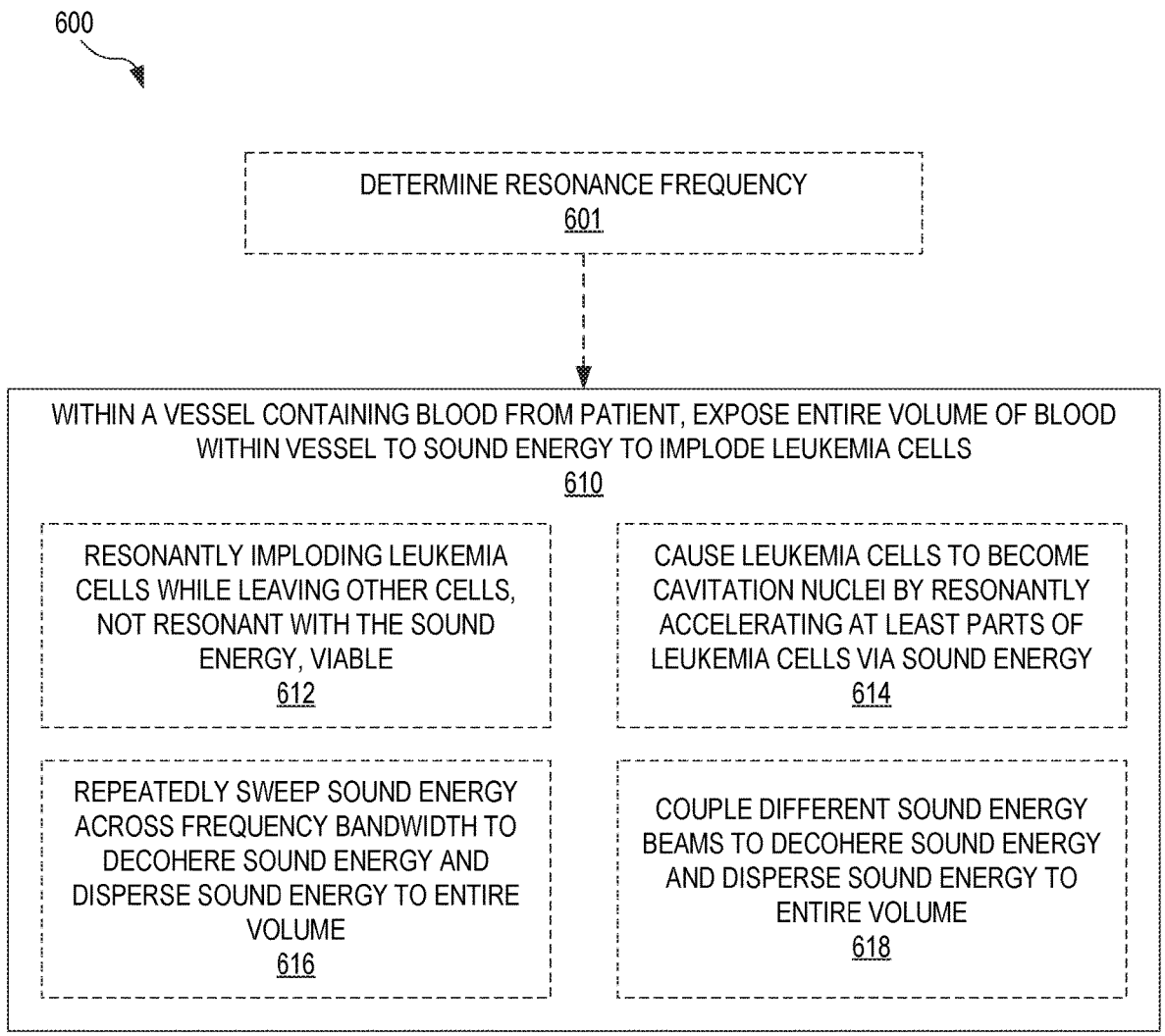
FIG. 6 illustrates a method for imploding leukemia cells in blood of a patient, according to an embodiment.

FIG. 6 illustrates one exemplary method 600 for imploding leukemia cells 192 in blood 190 of patient 180. Method 600 is performed by system 100, for example.

In a step 610, method 600 treats blood 190 located within a vessel that is external to patient 180. Step 610 exposes the entire volume of blood 190, within the vessel, to sound energy to implode leukemia cells 192 in blood 190. The sound energy is resonant with implosion of leukemia cells 192. In one example of step 610, drive circuitry 130 drives transducers 120 with an electric drive signal having frequency resonant with implosion of leukemia cells 192, such that transducers 120 expose the entire volume of blood 190, within vessel 110, to sound energy 140 that is resonant with implosion of leukemia cells 192.

Step 610 may include a step 612 of resonantly imploding leukemia cells 192 while leaving other cells, not resonant with the sound energy, viable, as discussed above in reference to FIG. 1. In one example of step 612, leukemia cells 192 have size different from most other cells in blood 190 such that these other cells remain viable when system 100 exposes blood 190 to sound energy 140.

Optionally, step 610 includes a step 614 of causing leukemia cells 192 to become cavitation nuclei by resonantly accelerating at least a part of each such leukemia cell 192 via the sound energy to induce oscillatory motion of this part of leukemia cell 192. The sound energy may resonantly accelerate the nucleus, a part of the nucleus, the cell wall, a part of the cell wall, or a combination thereof. In one example of step 614, sound energy 140, generated by transducers 120 and incident on a leukemia cell 192, resonantly accelerates at least one of the aforementioned parts of this leukemia cell 192.

In one embodiment, step 610 includes a step 616 of repeatedly sweeping the sound energy across a frequency bandwidth to decohere the sound energy and disperse the sound energy to the entire volume of blood 190 within the vessel, as discussed above in reference to FIGS. 3A and 3B. In one example of step 616, sweep unit 542 repeatedly sweeps the frequency of the control signal generated by generator(s) 530 across frequency bandwidth 354, to decohere sound energy 140 and disperse sound energy 140 to the entire volume of blood 190 within vessel 110, as discussed above in reference to FIGS. 3A and 3B.

In another embodiment, step 610 includes a step 618 of mutually coupling a plurality of different sound energy beams to decohere the sound energy of these sound energy beams and disperse the sound energy to the entire volume of blood 190 within the vessel, as discussed above in reference to FIGS. 4A-C. In one example of step 618, a plurality of transducers 120 are arranged such that the respective plurality of beams 340 of sound energy 140 generated by transducers 120 couple with each other to disrupt the coherence of beams 340. This disruption results in dispersion of sound energy 140 to the entire volume of blood 190 within vessel 110, as discussed above in reference to FIGS. 4A-C.

In yet another embodiment, step 610 includes both step 616 and step 618.

In one embodiment, step 610 is preceded by a step 601 of determining the resonance frequency for implosion of leukemia cells 192. In another embodiment, step 610 utilizes existing knowledge of the resonance frequency for implosion of leukemia cells 192.

In one exemplary scenario, method 600 is used to treat blood 190 of a patient 180 having 5 liters of blood 190 and a total number of leukemia cells 192 of around $10^{10}$. In an example of step 610 applied to this scenario, consider FIG. 1 where the bonding area between transducer(s) 120 and vessel 110 is 100 centimeter, and the power of sound energy 140 delivered to blood 190 is between 120 and 240 watts, that is, between 120 and 240 Joules/second. The energy associated with implosion of a leukemia cell 192 is on order of 0.1 microjoules. The efficiency of conversion of sound energy 140 into implosion of leukemia cell 192 may be about 1 percent. In this scenario, the total processing time required to implode all $10^{10}$ leukemia cells 192 in the 5 liters of blood 190 is approximately between 7 and 14 minutes. Thus, an exemplary treatment of patient 180, according to method 600, may encompass circulating the blood 190 of patient 180 through vessel 110 to treat the full volume of blood 190 of patient 180 over a duration of approximately 7-14 minutes.

Figure 7:
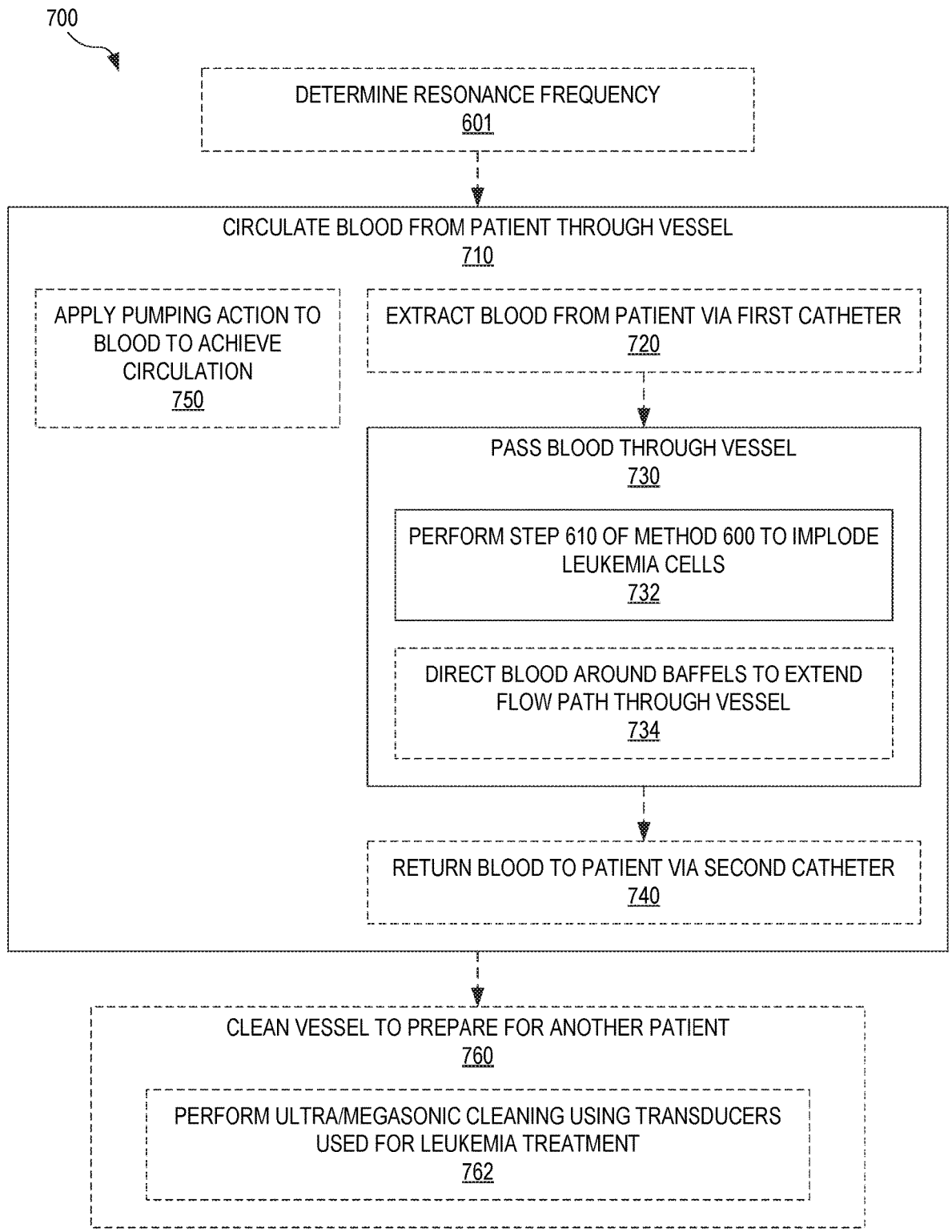
FIG. 7 illustrates a method for circulating blood out of a patient and through a vessel to implode leukemia cells in the blood before returning the blood to the patient, according to an embodiment.

FIG. 7 illustrates one exemplary method 700 for circulating blood 190 out of patient 180 and through a vessel to implode leukemia cells 192 in blood 190 before returning blood 190 to patient 180. Method 700 is an embodiment of method 600. Method 700 is performed by system 100, for example.

A step 710 circulates blood 190 from patient 180 through a vessel that is external to patient 180. Step 710 includes step 730, and optionally also steps 720 and 740.

In step 720, method 700 extracts blood 190 from patient 180 via a first catheter. In one example of step 710, system 100 extracts blood 190 from patient 180 via catheter 580.

In step 730, method 700 passes blood 190 through the vessel. In one example of step 730, system 100 passes blood 190 into vessel 110 via inlet 510, through vessel 110 from inlet 510 to outlet 512, and out of vessel 110 via outlet 512. Step 730 includes a step 732 of performing step 610 of method 600 to implode leukemia cells 192 in blood 190 within vessel 110. Optionally, step 730 further includes a step 734 of directing blood 190 around a set of baffles to extend the flow path of blood 190 through vessel 110, for example to prolong the time during which blood 190 is exposed to treatment. In one example of step 734, vessel 110 includes baffles 514 to extend the flow path of blood 190 from inlet 510 to outlet 512.

In step 740, blood 190 with imploded leukemia cells 192 is returned to patient 180 via a second catheter. In one example of step 740, system 100 returns blood 190 to patient via catheter 582.

Optionally, step 710 includes a step 750 of applying pumping action to blood 190 to achieve the circulation of blood 190 out of patient 180, through the vessel, and back into patient 180. In one example of step 750, pump 522 pumps blood 190.

Method 700 may include performing step 601 of method 600 prior to performing step 710, to determine the resonance frequency for implosion of leukemia cells 192.

In an embodiment, method 700 includes a step 760 of cleaning the vessel used in step 710 to prepare the vessel for another patient 180. Step 760 may utilize methods known in the art for decontaminating medical equipment. Step 760 may include a step 762 of performing ultrasonic and/or megasonic cleaning of the vessel 110. Herein, the megasonic frequency range refers to the range from about 350 kHz to about 15 megahertz (MHz). Step 762 utilizes the same transducers used to generate the sound energy used in step 732 to implode leukemia cells 192. Step 762 may use these transducers at the same frequency as used in step 732, and/or apply one or more frequencies that are different from the frequency used in step 732. In one example of step 762, vessel 110 is filled with a suitable cleaning liquid, and drive circuitry 130 drives transducers 120 to perform ultrasonic and/or megasonic cleaning of vessel 110, optionally decohereing the ultra/megasonic energy and dispersing the ultra/megasonic energy to the entire volume of liquid within vessel 110, as discussed above in reference to FIGS. 3A-4C. The cleaning liquid may be chosen to perform cold sterilization. In this case, the cleaning liquid may first be glutaraldehyde in sterile water, and next (as a rinsing step) sterilized water. For ease of cleaning, vessel 110 may be designed with coved corners and sanitary connection fittings.

FIGS. 8A and 8B illustrate one exemplary system 800 for imploding leukemia cells 192 of patient 180 using sound energy 140 having a sweeping frequency. System 800 is an embodiment of system 300. System 800 may perform method 600. FIG. 8A shows a frontal view of system 800, and FIG. 8B shows a cross-sectional side view of system 800. FIGS. 8A and 8B are best viewed together.

System 800 includes a case 883 and a plate 881, which cooperate to form an embodiment of vessel 110. Plate 881 is an embodiment of plate 520. System 800 further includes a plurality of transducers 882 mounted to plate 881. For clarity of illustration, not all transducers 882 are labeled in FIG. 8B. Each transducer 882 is an embodiment of transducer 120. Each transducer 882 includes a piezoelectric ceramic. The thickness of this piezoelectric ceramic is an odd integer number of half wavelengths of the sound energy within the piezoelectric ceramic, when transducer 882 is driven to generate sound energy 140 resonant with imploding leukemia cells 192. Thus, each transducer 882 may be resonantly driven to generate sound energy 140 resonant with implosion of leukemia cells 192. Since the thickness of plate 881 is an integer number of half-wavelengths of sound energy 140 (within plate 881), sound energy 140 is efficiently propagated to blood 190 within the vessel formed by plate 881 and case 883.

Case 883 includes an inlet 884 and an outlet 885, which are embodiments of inlet 510 and outlet 512, respectively. Case 883 may further include baffles 887 to extend the flow path of blood 190 between inlet 884 and outlet 885. Baffles 887 are embodiments of baffles 514. Optionally, system 800 includes escape tubing 888 that releases gas or air from blood 190.

System 800 may include cables 886 that connect transducers 882 to drive circuitry 130 (not shown in FIGS. 8A and 8B).

FIG. 9 illustrates one exemplary system 900 for circulating blood 190 out of patient 180 and through vessel 110 to implode leukemia cells 192 in blood 190 before returning blood 190 to patient 180. System 900 is an embodiment of system 100. System 900 may perform method 700.

System 900 includes vessel 110 and at least one transducer 120 coupled to outside surface 114 of a wall of vessel 110. For clarity of illustration, only one transducer 120 is labeled in FIG. 9. In an embodiment, system 900 includes plate 520, wherein plate 520 forms a wall of vessel 110 and each transducer 120 is coupled to plate 520. System 900 further includes drive circuitry 130 that is coupled to each transducer 120.

System 900 includes fluid handling components that function to circulate blood 190 out of patient 180, through vessel 110, and back into patient 180. Specifically, system 900 includes a catheter 910 that extracts blood 190 from a vein of patient 180, a catheter 960 that returns blood 190 to patient 180, and a pump 930 that applies pumping action to blood 190 to circulate blood 190 out of catheter 910 through vessel 110 to catheter 960. Pump 930 is a centrifugal blood pump. To complete the fluidic circuit, system 900 includes a fluidic connector 920 that connects catheter 910 to an inlet of pump 930, a tube 940 that connects an outlet of pump 930 to vessel 110 (for example to inlet 510, not shown in FIG. 9), and a tube 950 that connects vessel 110 (for example outlet 512, not shown in FIG. 9) to catheter 960.

System 900 may implement system 800 as vessel 110, plate 520, and transducers 120.

Figure 10A:
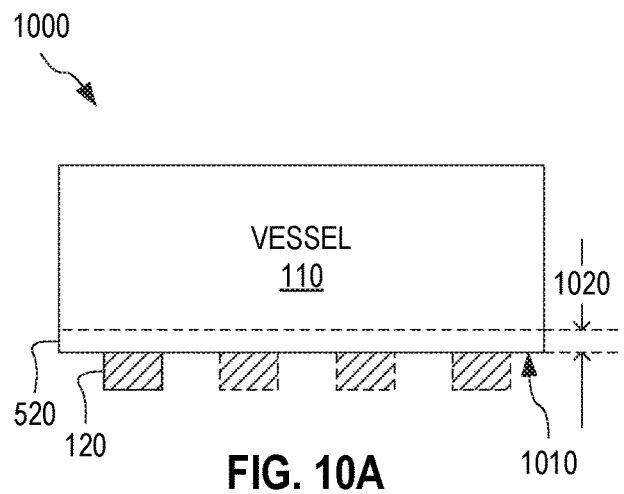
FIGS. 10A and 10B illustrate one exemplary configuration of the vessel and transducers of the system of FIG. 1.
Figure 10B:
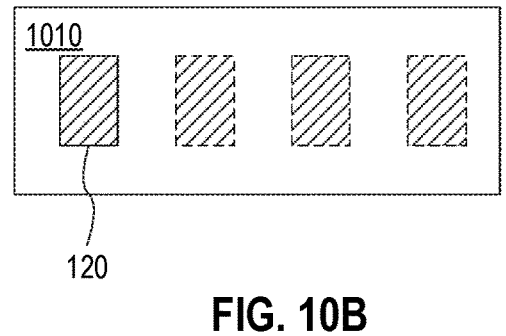

FIGS. 10A and 10B illustrate one exemplary configuration 1000 of vessel 110 and transducers 120 of system 100. In configuration 1000, each transducer 120 is mounted to an outside surface 1010 of vessel 110. Outside surface 1010 is an embodiment of outside surface 114. In an embodiment, outside surface 1010 is a surface of a substantially planar wall of vessel 110. In an embodiment, plate 520 forms a wall of vessel 110, and outside surface 1010 is the surface of plate 520 facing away from vessel 110. FIG. 10A shows a cross-sectional side view of vessel 110 with transducer(s) 120 and, optionally, plate 520. FIG. 10B shows the placement of transducer(s) 120 on outside surface 1010. FIGS. 10A and 10B are best viewed together.

In embodiments of system 100, which include a plurality of transducers 120 arranged according to configuration 1000, transducers 120 are arranged along a row. For clarity of illustration, not all transducers 120 are labeled in FIGS. 10A and 10B.

In embodiments of system 100, which are arranged according to configuration 1000 and include plate 520, plate 520 has thickness 1020 that is an integer number of half wavelengths of sound energy 140 within plate 520. In one example, plate 520 is a stainless steel plate (316 stainless steel), and thickness 1020 is about 0.242 inches. When operating to generate sound energy 140 at a frequency of about 467 kHz, the thickness of plate 520 is one half wavelength of sound energy 140 within plate 520. When operating to generate sound energy 140 at a frequency of about 1.4 MHz, the thickness of plate 520 is about three half wavelengths of sound energy 140 within plate 520.

Without departing from the scope hereof, vessel 110 may have a different shape than shown in FIGS. 10A and 10B. For example, vessel 110 may be partly tubular as shown in FIGS. 8A and 8B.

Figure 11:
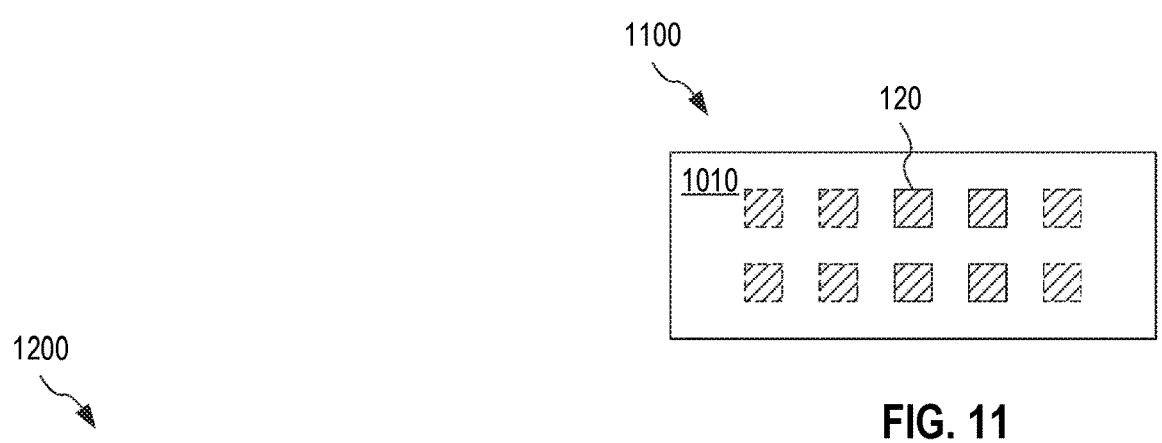
FIG. 11 illustrates another exemplary configuration of the vessel and transducers of the system of FIG. 1.

FIG. 11 illustrates another exemplary configuration 1100 of vessel 110 and transducers 120 of system 100. FIG. 11 shows configuration 1100 in the same view as used in FIG. 10B. Configuration 1100 is similar to configuration 1000 except that a plurality of transducers 120 arranged in an array having at least two rows and at least two columns. For clarity of illustration, not all transducers 120 are labeled in FIG. 11. Without departing from the scope hereof, configuration 1100 may include any number of transducers 120 configurable in a plurality of rows and columns.

Figure 12:
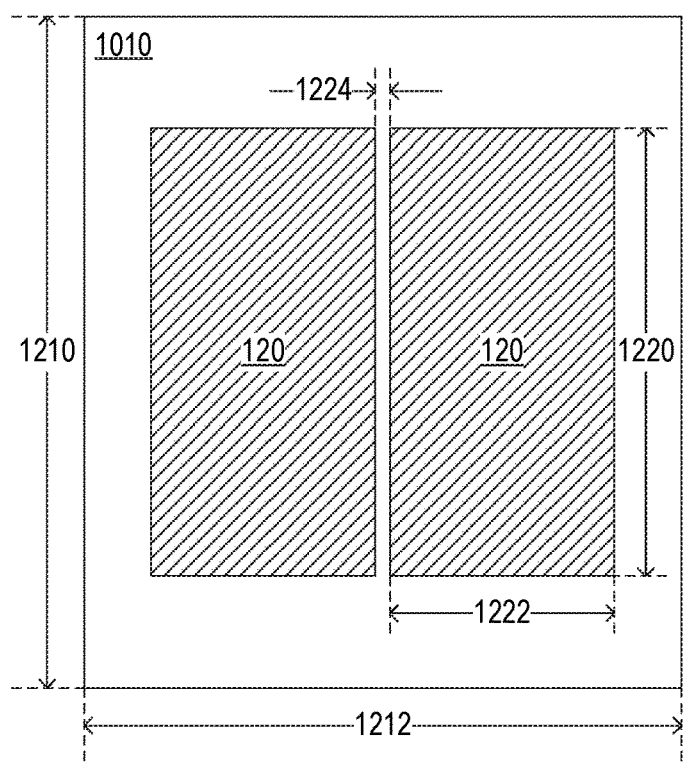
FIG. 12 illustrates yet another exemplary configuration of the vessel and transducers of the system of FIG. 1.

FIG. 12 illustrates yet another configuration 1200 of vessel 110 and transducers 120 of system 100. FIG. 12 shows configuration 1200 in the same view as used in FIG. 10B. Configuration 1200 is similar to configuration 1000. In embodiments of system 100, arranged according to configuration 1200, system 100 includes two transducers 120 arranged side-by-side with spacing 1224 between them. Each transducer 120 has length 1220 and width 1222, in the plane parallel with surface 1010. Surface 1010 has length 1210 and width 1212.

In one implementation, length 1210 is 90 millimeters (mm), width 1212 is 80 mm, length 1220 is 66.55 mm, width 1222 is 28.45 mm, and spacing 1224 is 0.5 mm. The thickness of each transducer 120 (dimension orthogonal to length 1220 and width 1222) may be about 5 mm to be resonant with sound energy at 440 kHz and overtones at 1.4 MHz, 2.3 MHz, and 3.2 MHz. Without departing from the scope hereof, the thickness of each transducer 120 may be adapted to be resonant with sound energy of the frequency required for implosion of leukemia cells 192. For example, the thickness of 5 mm may be reduced by 50% to make transducer 120 resonant with sound energy at 880 kHz.

Figure 13:
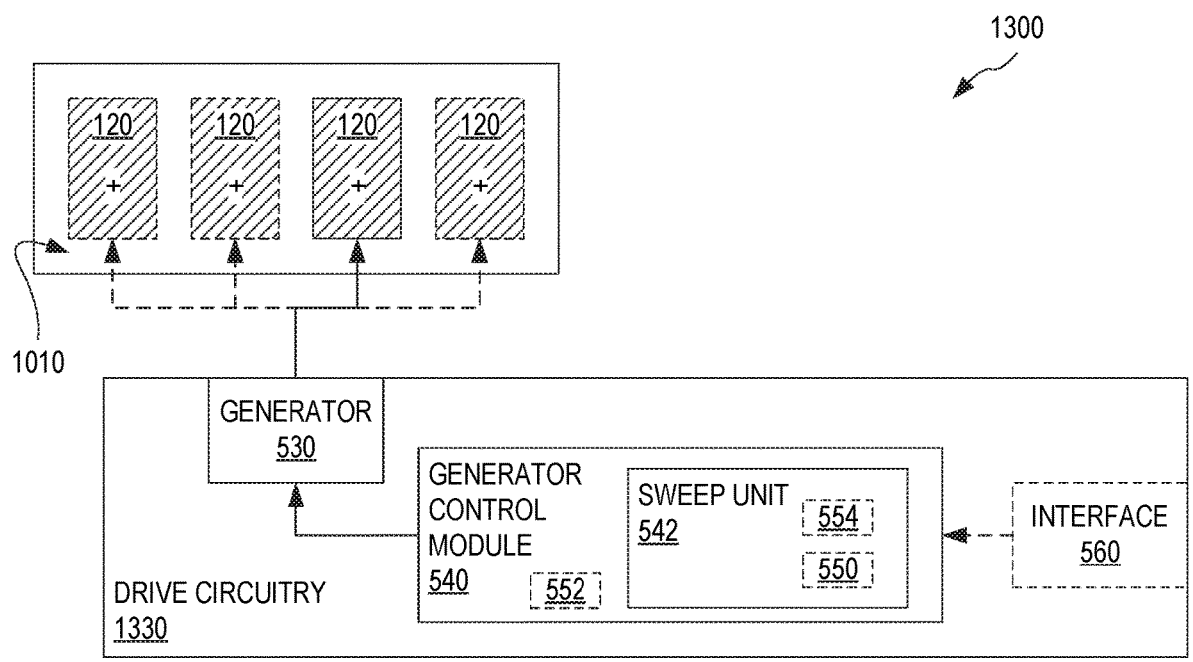
FIG. 13 illustrates a system for imploding leukemia cells of a patient, which utilizes frequency sweeping of the sound energy to decohere the sound energy and disperse the sound energy to the entire volume of blood within a vessel, according to an embodiment.

FIG. 13 illustrates one exemplary system 1300 for imploding leukemia cells 192 of patient 180, which utilizes frequency sweeping of sound energy 140 to disperse sound energy 140 to the entire volume of blood 190 within vessel 110. System 1300 is an embodiment of system 300. System 1300 may perform method 600. System 1300 includes vessel 110, at least one transducer 120 mounted to surface 1010, and drive circuitry 1330. Surface 1010 may be a surface of plate 520. FIG. 13 shows transducer(s) 120 and vessel 110 in the same view as used in FIG. 10B.

Vessel 110 and transducer(s) 120 may be arranged according to any of configurations 1000, 1100, and 1200. However, other configurations may be used as well, without departing from the scope hereof. For example, a plurality of transducers 120 may be mounted to surface 1010 in a non-rectangular array, e.g., a circular pattern.

Drive circuitry 1330 is an embodiment of drive circuitry 130, which implements generator 530 and generator control module 540, wherein generator control module 540 implements sweep unit 542. In operation, generator control module 540, with the use of sweep unit 542, controls generator 530 to generate a control signal with a sweeping frequency according to frequency setting 552, frequency bandwidth setting 554, and sweep pattern setting 550.

In embodiments of system 1300 including a plurality of transducers 120, generator 530 applies the same control signal to each transducer 120 and generator 530 is coupled to each transducer 120 with the same polarity. As discussed above in reference to FIG. 3A, decoherence of sound energy 140 and dispersion of sound energy 140 to the entire volume of blood 190 within vessel 110 is ensured by sweeping the frequency of sound energy 140. Without departing from the scope hereof, system 1300 may be configured with more or fewer than the four transducers 120 shown in FIG. 13.

Figure 14:
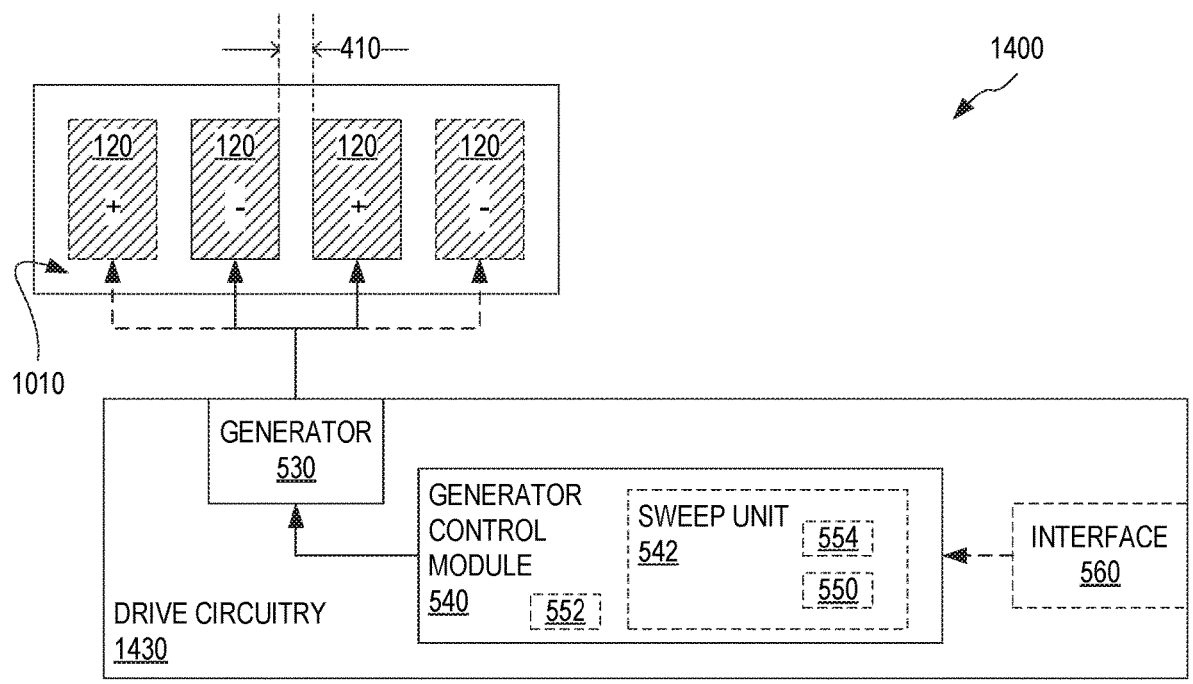
FIG. 14 illustrates a system for imploding leukemia cells of a patient, which is configured to operate two or more transducers out of phase with each other to decohere the sound energy and disperse sound energy to the entire volume of blood within a vessel, according to an embodiment.

FIG. 14 illustrates one exemplary system 1400 for imploding leukemia cells 192 of patient 180, which is configured to operate two or more transducers 120 out of phase with each other to decohere sound energy 140 and disperse sound energy 140 to the entire volume of blood 190 within vessel 110. FIG. 14 shows transducer(s) 120 and vessel 110 in the same view as used in FIG. 13. System 1400 is an embodiment of system 402. System 1400 may perform method 600. Without departing from the scope hereof, system 1400 may include any number of transducers 120 greater than one.

System 1400 is similar to system 1300 except for (a) including a plurality of transducers 120 arranged such that adjacent transducers 120 are spaced apart by distance 410 and coupled to generator 530 with opposite polarity, and (b) including drive circuitry 1430 instead of drive circuitry 1330. Drive circuitry 1430 is similar to drive circuitry 1330, except for sweep unit 542 being optional in drive circuitry 1430. By virtue of using opposite coupling polarity for adjacent transducers 120, adjacent transducers 120 produce respective sound energy 140 that are 180 degrees out of phase with each other. As discussed above in reference to FIG. 4B, this results in decoherence of sound energy 140 and dispersion of sound energy 140 to the entire volume of blood 190 within vessel 110.

In an embodiment of system 1400, generator control module 540 includes sweep unit 542, such that system 1400 may sweep the frequency of sound energy 140 generated by transducers 120 to, at least potentially, improve the efficiency of decoherence of sound energy 140 and dispersion of sound energy 140 to the entire volume of blood 190 within vessel 110.

Figure 15:
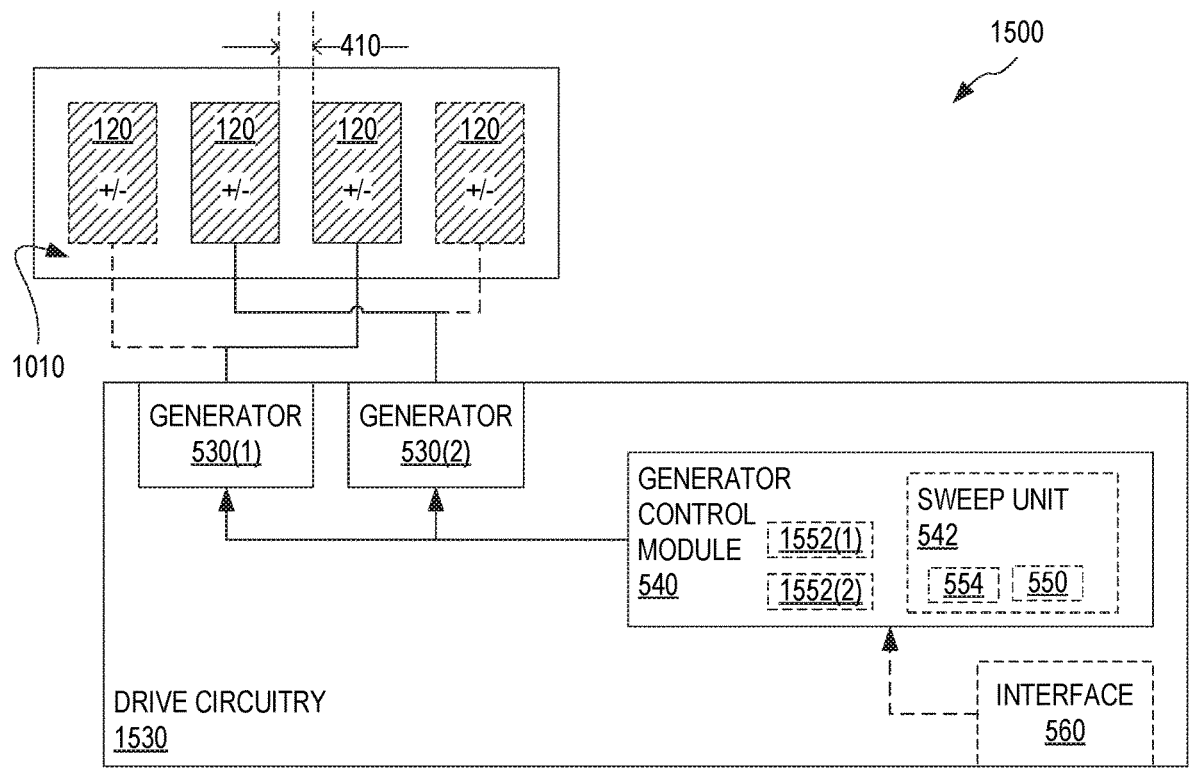
FIG. 15 illustrates a system for imploding leukemia cells of a patient, which is configured to operate two or more transducers at slightly different frequencies to decohere the sound energy and disperse sound energy to the entire volume of blood within a vessel, according to an embodiment.

FIG. 15 illustrates one exemplary system 1500 for imploding leukemia cells 192 of patient 180, which is configured to operate two or more transducers 120 at slightly different frequencies to decohere sound energy 140 and disperse sound energy 140 to the entire volume of blood 190 within vessel 110. FIG. 15 shows transducer(s) 120 and vessel 110 in the same view as used in FIG. 13. System 1500 is an embodiment of system 402. System 1500 may perform method 600. Without departing from the scope hereof, system 1500 may include any number of transducers 120 greater than one.

System 1500 is similar to system 1400 except that adjacent transducers 120 are configured to receive respective control signals of different frequencies. For this purpose, system 1500 implements drive circuitry 1530 instead of drive circuitry 1430. Drive circuitry 1530 is similar to drive circuitry 1430 except that (a) drive circuitry 1530 includes two generators 530(1) and 530(2), and (b) generator control module 540 has two frequency settings 1552(1) and 1552(2). In each pair of adjacent transducers 120, one transducer 120 is coupled to generator 530(1) while the other transducer 120 is coupled to generator 530(2). Frequency setting 1552(1) defines the frequency of the control signal generated by generator 530(1). Frequency setting 1552(2) defines the frequency of the control signal generated by generator 530(2). Each of frequency settings 1552(1) and 1552(2) is an example of frequency setting 552. Each of frequency settings 1552(1) and 1552(2) defines a frequency that is substantially resonant with imploding leukemia cells 192 in blood 190. However, the two frequencies defined by frequency settings 1552(1) and 1552(2) are sufficiently different that the different frequencies of sound energy 140 generated by adjacent transducers 120 result in decoherence of sound energy 140 and dispersion of sound energy 140 to the entire volume of blood 190 within vessel 110, as discussed above in reference to FIG. 4B.

In an embodiment of system 1500, generator control module 540 includes sweep unit 542, such that system 1500 may sweep the frequency of sound energy 140 generated by transducers 120 to, at least potentially, improve the efficiency of decoherence of sound energy 140 and dispersion of sound energy 140 to the entire volume of blood 190 within vessel 110. In this embodiment, generator 530(1) sweeps the frequency of its associated control signal about the frequency defined by frequency setting 1552(1), while generator 530(2) sweeps the frequency of its associated control signal about the frequency defined by frequency setting 1552(2).

Optionally, to at least potentially improve the efficiency of decoherence of sound energy 140 and dispersion of sound energy 140 to the entire volume of blood 190 within vessel 110, adjacent transducers 120 are coupled to generator 530(1)/530(2) with mutually opposite polarities to obtain the sound energy dispersion benefit discussed above in reference to FIG. 14.

Figure 16:
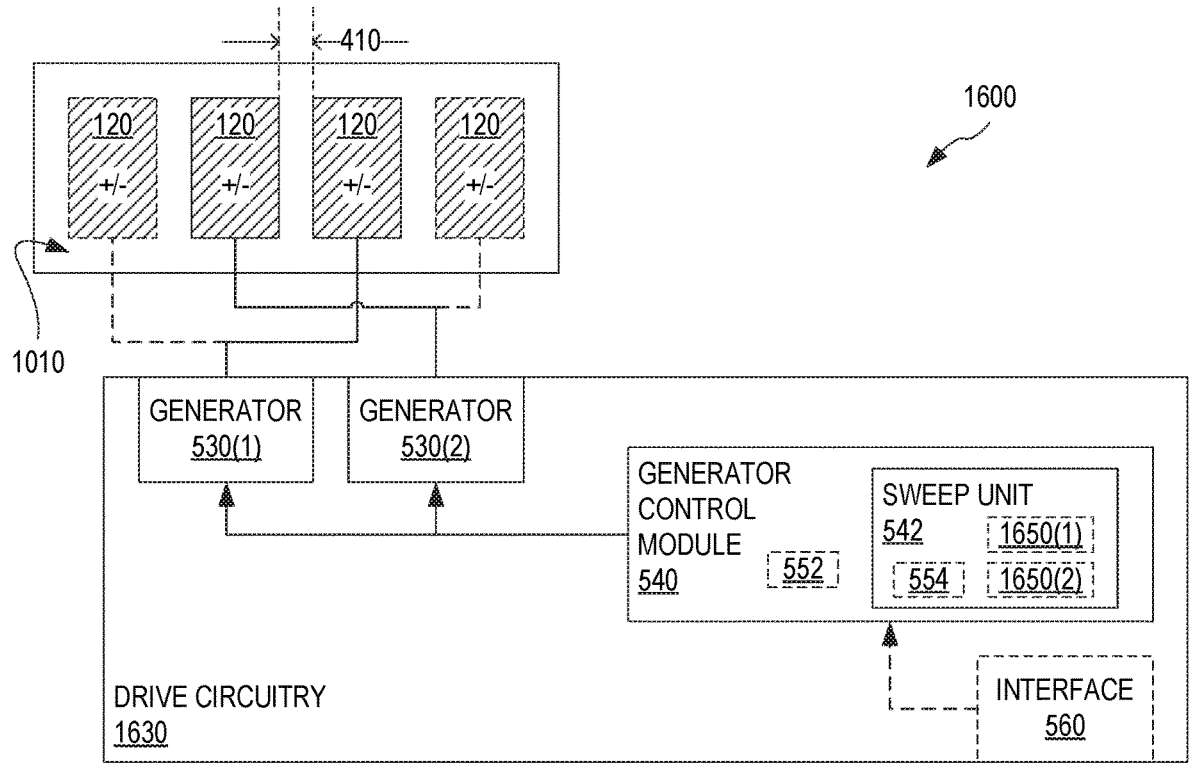
FIG. 16 illustrates a system for imploding leukemia cells of a patient, which utilizes frequency sweeping with a plurality of sweep patterns to decohere the sound energy and disperse sound energy to the entire volume of blood within a vessel, according to an embodiment.

FIG. 16 illustrates one exemplary system 1600 for imploding leukemia cells 192 of patient 180, which utilizes frequency sweeping with a plurality of sweep patterns to decohere sound energy 140 and disperse sound energy 140 to the entire volume of blood 190 within vessel 110. FIG. 16 shows transducer(s) 120 and vessel 110 in the same view as used in FIG. 13. System 1600 is an embodiment of each of systems 400 and 402, and combines features of systems 400 and 402. System 1600 may perform method 600. Without departing from the scope hereof, system 1600 may include any number of transducers 120 greater than one.

System 1600 is similar to system 1500 except for implementing drive circuitry 1630 that (a) requires sweep unit 542 such that generators 530(1) and 530(2) sweep the frequency of the associated control signals, and (b) sweep unit 542 is configured with two sweep pattern settings 1650(1) and 1650(2) instead of two frequency settings 1552(1) and 1552(2). Sweep pattern setting 1650(1) defines the sweep pattern for generator 530(1), while sweep pattern setting 1650(2) defines the sweep pattern for generator 530(2). In one implementation, sweep pattern settings 1650(1) and 1650(2) define respective sweep patterns that differ from each other in sweep period 356 and/or phase of the sweep pattern. For example, sweep pattern settings 1650(1) and 1650(2) may define respective periodic sweep patterns that are 180 degrees out of phase with each other, such that generator 530(1) outputs the lowest frequency when generator 530(1) outputs the highest frequency. As discussed above in reference to FIG. 4B, this results in decoherence of sound energy 140 and dispersion of sound energy 140 to the entire volume of blood 190 within vessel 110.

To improve the efficiency of decoherence of sound energy 140 and dispersion of sound energy 140 to the entire volume of blood 190 within vessel 110, adjacent transducers 120 may be coupled to generator 530(1)/530(2) with opposite polarity to obtain the sound energy dispersion benefit discussed above in reference to FIG. 14.

Furthermore, although not shown in FIG. 16, drive circuitry 1630 may be configured with frequency settings 1552(1) and 1552(2) to operate adjacent transducers 120 with different center frequencies 352 to improve the efficiency of decoherence of sound energy 140 and dispersion of sound energy 140 to the entire volume of blood 190 within vessel 110, without departing from the scope hereof.

Figure 17A:
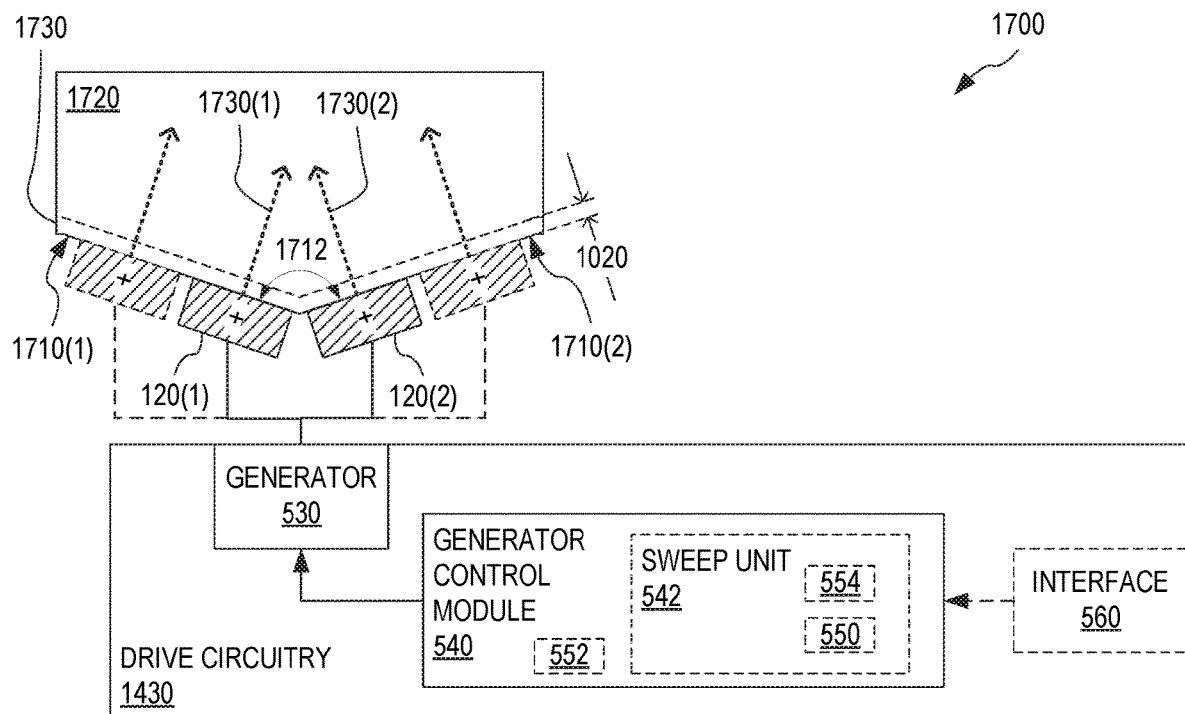
FIGS. 17A and 17B illustrate a system for imploding leukemia cells of a patient, which directs sound energy in a plurality of intersecting directions to decohere the sound energy and disperse the sound energy to the entire volume of blood within a vessel, according to an embodiment.
Figure 17B:
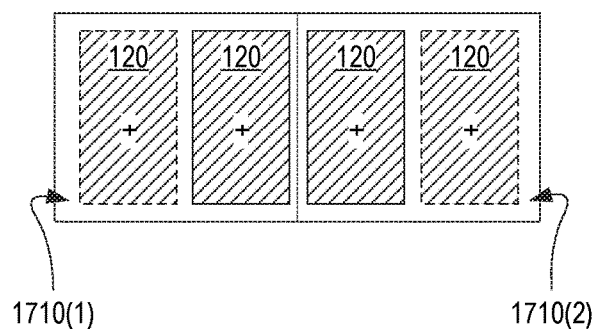

FIGS. 17A and 17B illustrate one exemplary system 1700 for imploding leukemia cells 192 of patient 180, which directs sound energy 140 in a plurality of intersecting directions to decohere sound energy 140 and disperse sound energy 140 to the entire volume of blood 190 within a vessel 1720. System 1700 is an embodiment of system 400. System 1700 may perform method 600. FIG. 17A shows system 1700 in the same view as used in FIG. 10A, and FIG. 17B shows system 1700 in the same view as used in FIG. 10B. FIGS. 17A and 17B are best viewed together.

System 1700 is similar to system 1400 except for implementing vessel 110 as a vessel 1720 having a bent wall to overlap sound energy 140 generated by transducers 120, mounted to the bent wall, instead of requiring opposite polarity coupling of adjacent transducers 120. Vessel 1720 is an embodiment of vessel 110. One wall of vessel 1720 includes two surfaces 1710(1) and 1710(2) that are non-parallel. Each of outside surfaces 1710(1) and 1710(2) is an embodiment of outside surface 114. Thus, angle 1712 indicated in FIG. 17A is less than 180 degrees. Angle 1712 may be in the range from 170 to 175 degrees. In an embodiment, a plate 1730 forms surfaces 1710(1) and 1710(2). Plate 1730 is an extension of plate 520 and has two substantially planar portions forming surfaces 1710(1) and 1710(2), respectively. Plate 1730 has thickness 1020 as discussed for plate 520 above in reference to FIGS. 10A and 10B. Plate 1730 may be at least partly formed from two separate plates respectively forming surfaces 1710(1) and 1710(2). For clarity of illustration, not all transducers 120 are labeled in FIG. 17A. Without departing from the scope hereof, system 1700 may include any number of transducers 120 greater than one.

At least one transducer 120(1) is mounted to surface 1710(1) and at least one transducer 120(2) is mounted to surface 1710(2). Transducer 120(1) directs sound energy along a direction 1730(1), and transducer 120(2) directs sound energy along a direction 1730(2). Since angle 1712 is less than 180 degrees, directions 1730(1) and 1730(2) are non-parallel. In the illustration shown in FIG. 17A, directions 1730(1) and 1730(2) intersect before sound energy 140 propagating along directions 1730(1) and 1730(2) reach the top of vessel 1720. Alternatively, directions 1730(1) and 1730(2) may intersect after reflection of sound energy 140, propagating along directions 1730(1) and 1730(2), off of the blood-to-solid interface at the top of vessel 1720 (if vessel 1720 is filled with blood 190) or off of the blood-to-air interface (if vessel 1720 is only partly filled with blood 190). As discussed in reference to FIG. 4A, the coupling between sound energy 140 propagating along directions 1730(1) and 1730(2) results in decoherence of sound energy 140 and dispersion of sound energy 140 to the entire volume of blood 190 within vessel 1720.

Without departing from the scope hereof, the bent wall of system 1700 may be replaced by a curved wall or a wall that is both bent and curved, to overlap sound energy 140 generated by transducers 120 mounted to the curved (or bent and curved) wall.

In an embodiment of system 1700, generator control module 540 includes sweep unit 542, such that system 1700 may sweep the frequency of sound energy 140 generated by transducers 120 to improve the efficiency of decoherence of sound energy 140 and dispersion of sound energy 140 to the entire volume of blood 190 within vessel 1720.

Figure 18:
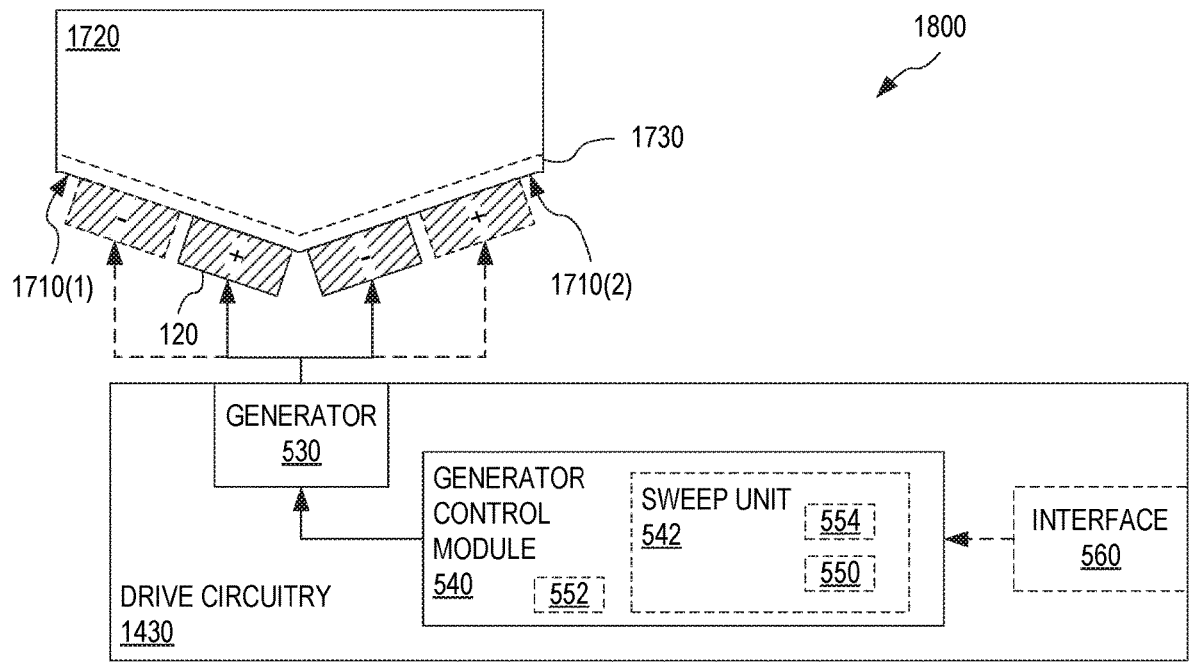
FIG. 18 illustrates a system for imploding leukemia cells of a patient, which directs out-of phase sound energy in a plurality of intersecting directions to decohere the sound energy and disperse the sound energy to the entire volume of blood within a vessel, according to an embodiment.

FIG. 18 illustrates one exemplary system 1800 for imploding leukemia cells 192 of patient 180, which directs out-of phase sound energy 140 in a plurality of intersecting directions to decohere sound energy 140 and disperse sound energy 140 to the entire volume of blood 190 within vessel 1720. System 1800 is an embodiment of each of systems 400 and 402, and combines functionality of systems 400 and 402. System 1800 may perform method 600. FIG. 18 shows system 1800 in the same view as used in FIG. 17A. For clarity of illustration, not all transducers 120 are labeled in FIG. 18. Without departing from the scope hereof, system 1800 may include any number of transducers 120 greater than one.

System 1800 is similar to system 1700 except for utilizing mutually opposite polarities of coupling of adjacent transducers 120 to generator 530, as discussed above in reference to FIG. 14, to at least potentially improve the efficiency of decoherence of sound energy 140 and dispersion of sound energy 140 to the entire volume of blood 190 within vessel 1720, as compared to that of system 1700.

Figure 19:
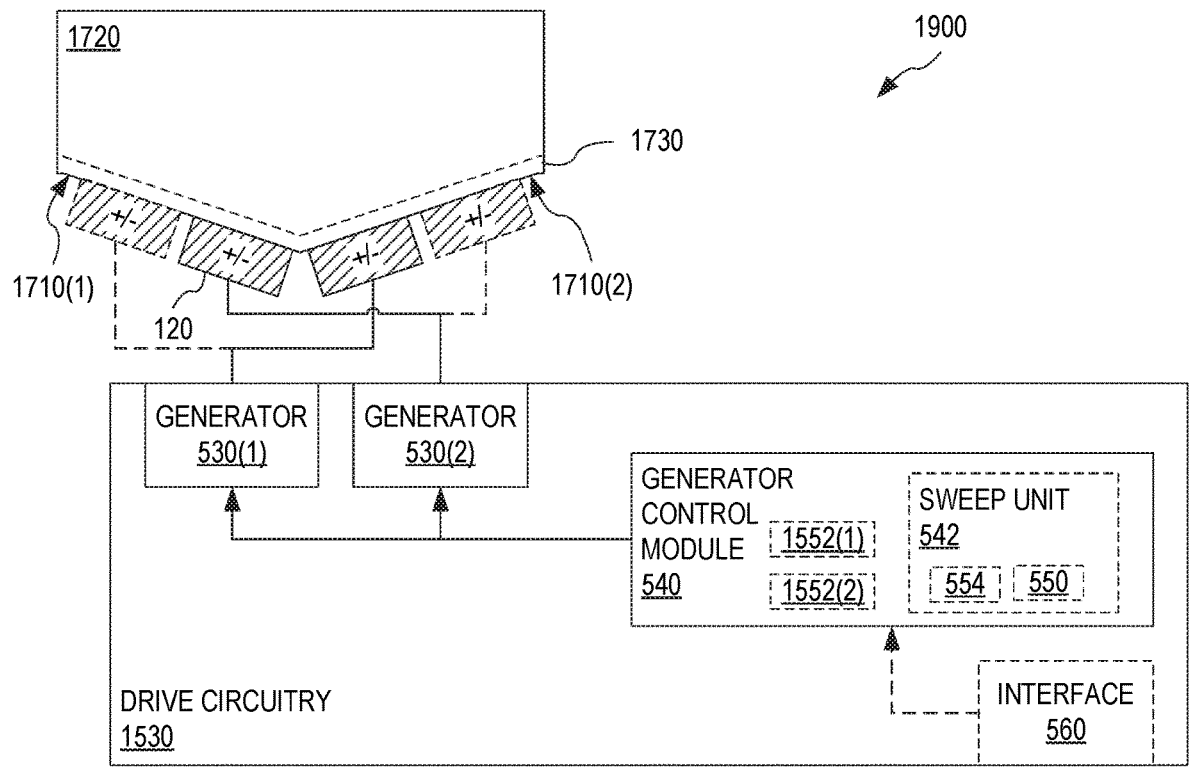
FIG. 19 illustrates a system for imploding leukemia cells of a patient, which directs sound energy of different frequencies in a plurality of intersecting directions to disperse the sound energy to the entire volume of blood within a vessel, according to an embodiment.

FIG. 19 illustrates one exemplary system 1900 for imploding leukemia cells 192 of patient 180, which directs sound energy 140 of different frequencies in a plurality of intersecting directions to decohere sound energy 140 and disperse sound energy 140 to the entire volume of blood 190 within vessel 1720. System 1900 is an embodiment of each of systems 400 and 402, and combines functionality of systems 400 and 402. System 1900 may perform method 600. FIG. 19 shows system 1900 in the same view as used in FIG. 17A. For clarity of illustration, not all transducers 120 are labeled in FIG. 19. Without departing from the scope hereof, system 1900 may include any number of transducers 120 greater than one.

System 1900 is similar to system 1700 except that adjacent transducers 120 are configured to receive respective control signals of different frequencies. For this purpose, system 1700 implements drive circuitry 1530 instead of drive circuitry 1430, as discussed above in reference to FIG. 15. Thus, system 1900 combines the sound energy decoherence and dispersion mechanisms of systems 1700 and 1500 to, at least potentially, improve the efficiency of decoherence of sound energy 140 and dispersion of sound energy 140 to the entire volume of blood 190 within vessel 1720, as compared to that of system 1700.

Optionally, to at least potentially improve the efficiency of decoherence of sound energy 140 and dispersion of sound energy 140 to the entire volume of blood 190 within vessel 1720, adjacent transducers 120 are coupled to generator 530(1)/530(2) with mutually opposite polarities to further obtain the sound energy decoherence and dispersion benefit discussed above in reference to FIG. 14.

Figure 20:
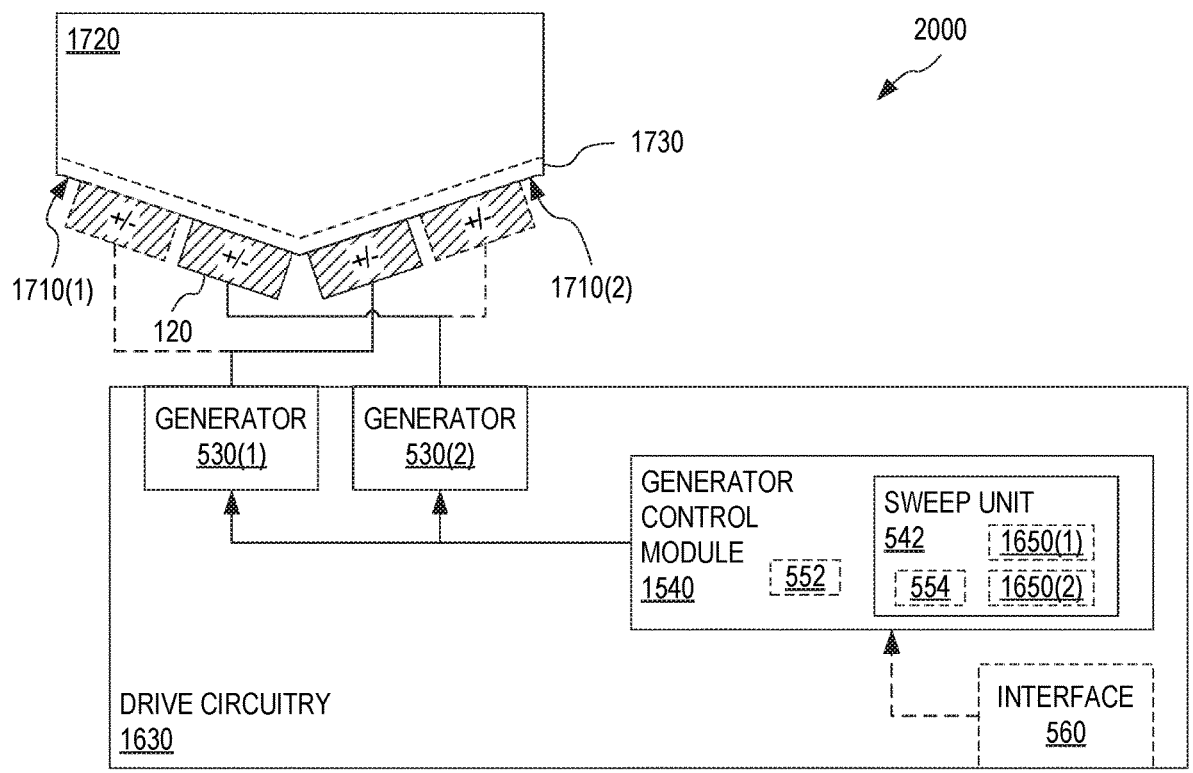
FIG. 20 illustrates a system for imploding leukemia cells of a patient, which directs sound energy in a plurality of intersecting directions and further utilizes frequency sweeping with a plurality of sweep patterns to decohere the sound energy and disperse the sound energy to the entire volume of blood within a vessel, according to an embodiment.

FIG. 20 illustrates one exemplary system 2000 for imploding leukemia cells 192 of patient 180, which directs sound energy 140 in a plurality of intersecting directions and further utilizes frequency sweeping with a plurality of sweep patterns to decohere sound energy 140 and disperse sound energy 140 to the entire volume of blood 190 within vessel 1720. FIG. 20 shows transducer(s) 120 and vessel 110 in the same view as used in FIG. 17A. System 2000 is an embodiment of each of systems 400 and 402, and combines features of systems 400 and 402. System 2000 may perform method 600. For clarity of illustration, not all transducers 120 are labeled in FIG. 20. Without departing from the scope hereof, system 2000 may include any number of transducers 120 greater than one.

System 2000 is similar to system 1900 except for implementing drive circuitry 1630, instead of drive circuitry 1530, to apply different sweep patterns to adjacent transducers 120, as discussed above in reference to FIG. 16. Thus, system 2000 combines the sound energy decoherence and dispersion mechanisms of systems 1700 and 1600 to, at least potentially, improve the efficiency of decoherence of sound energy 140 and dispersion of sound energy 140 to the entire volume of blood 190 within vessel 1720, as compared to that of system 1700.

Optionally, to at least potentially improve the efficiency of decoherence of sound energy 140 and dispersion of sound energy 140 to the entire volume of blood 190 within vessel 1720, adjacent transducers 120 are coupled to generator 530(1)/530(2) with mutually opposite polarities to further obtain the sound energy decoherence and dispersion benefit discussed above in reference to FIG. 14.

Furthermore, although not shown in FIG. 20, drive circuitry 1630 may be configured with frequency settings 1552(1) and 1552(2) to operate adjacent transducers 120 with different center frequencies 352 to improve the efficiency of decoherence of sound energy 140 and dispersion of sound energy 140 to the entire volume of blood 190 within vessel 110, without departing from the scope hereof.

Figure 21:
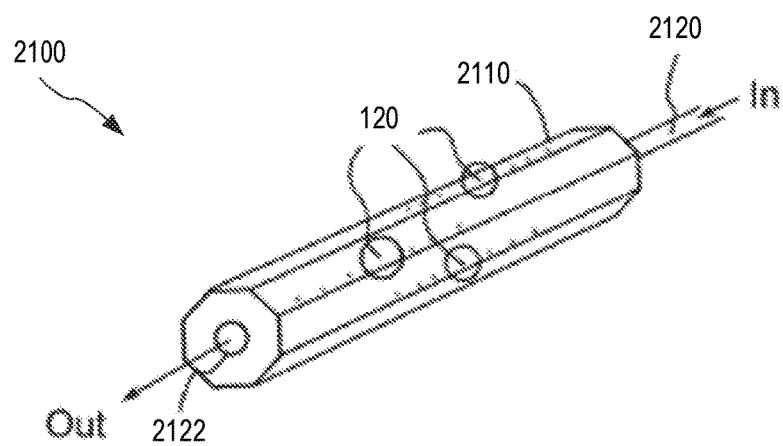
FIG. 21 illustrates a system for imploding leukemia cells of a patient, which is configured to direct sound energy into a vessel, containing blood, from a plurality of intersecting directions to decohere the sound energy and disperse the sound energy to the entire volume of blood within the vessel, according to an embodiment.

FIG. 21 illustrates one exemplary system 2100 for imploding leukemia cells 192 of patient 180, which is configured to direct sound energy into a vessel 2110, containing blood 190, from a plurality of intersecting directions to decohere sound energy 140 and disperse sound energy 140 to the entire volume of blood 190 within vessel 2110. System 2100 is an embodiment of system 100 and may perform method 600.

Vessel 2110 is in the shape of an elongated prism with a polygonal cross section perpendicular to the axis of elongation. The embodiment shown in FIG. 21 has an octagonal cross section. However, the cross section may be a polygon with any number of sides greater than or equal to three, without departing from the scope hereof. For example, the cross section of vessel 2110 may be rectangular or hexagonal. Vessel 2110 includes an inlet 2120 configured to receive blood 190 and an outlet 2122 through which blood 190 may be returned to patient 180. Inlet 2120 and outlet 2122 are located at opposite ends of vessel 2110.

Transducers 120 are mounted to at least three different sides of vessel 2110 to direct sound energy 140 into blood 190 along at least three non-parallel dimensions, respectively, such that sound energy 140 generated by different transducers 120 intersect and inter-couple to decohere sound energy 140 and disperse sound energy 140 to the entire volume of blood 190 within vessel 2110.

Although not shown in FIG. 21, vessel 2110 may incorporate plate 1730 along each side of vessel 2110 that is associated with transducers 120, without departing from the scope hereof. Also, although not shown in FIG. 21, system 2100 may include drive circuitry 130 and, optionally, fluid handling elements discussed above in reference to FIG. 5. The circles labeled "120" indicate transducers 120. The lines of dots adjacent these circles indicate optional additional transducers 120. System 2100 may implement transducers 120 as direct-bonded piezoelectric transducers, Langevin transducers, or a combination thereof.

Figure 22:
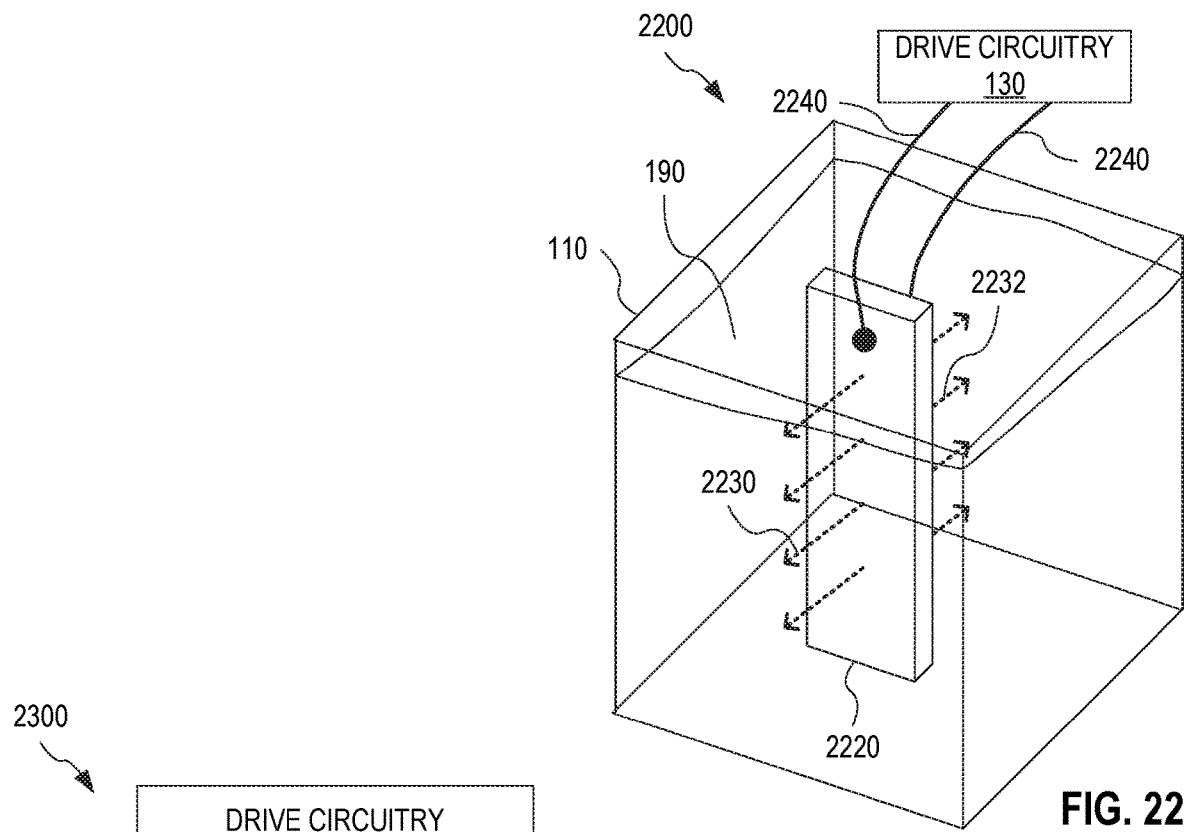
FIG. 22 illustrates a system for imploding leukemia cells of a patient 180, using sweeping-frequency sound energy generated by a single immersible transducer immersed in blood inside a vessel, according to an embodiment.

FIG. 22 illustrates one exemplary system 2200 for imploding leukemia cells 192 of patient 180, using sweeping-frequency sound energy generated by a single immersible transducer 2220 immersed in blood 190 inside vessel 110. Immersible transducer 2220 is an embodiment of transducer 120, and system 2200 is an embodiment of system 302. System 2200 may perform method 600.

System 2200 includes vessel 110, immersible transducer 2220, and drive circuitry 130 configured to drive immersible transducer 2220 with a sweeping frequency as discussed above in reference to FIGS. 3A and 3B. Immersible transducer 2220 generates sound energy 140 that propagates away from immersible transducer 2220 in two substantially opposite directions 2230 and 2232. In one embodiment, immersible transducer 2220 includes a substantially planar piezoelectric ceramic and two electrodes coupled to two opposing sides of the piezoelectric ceramic, wherein the two opposing sides of the piezoelectric ceramic face in directions 2230 and 2232, respectively. Drive circuitry 130 is connected to immersible transducer 2220 via electrical leads 2240. Leads 2240 may pass through a wall of vessel 110.

Although not shown in FIG. 22, system 2200 may include mounting hardware for holding immersible transducer 2220 inside vessel 110, without departing from the scope hereof. In one embodiment, leads 2240 are integrated in such mounting hardware. Also, system 2200 may include fluid handling components such as discussed above in reference to FIG. 5, without departing from the scope hereof. Also without departing from the scope hereof, system 2200 may utilize a vessel 110 of shape different from that shown in FIG. 22, for example a cylindrical vessel.

In operation, drive circuitry 130 drives immersible transducer 2220 with a control signal having a sweeping frequency, such that immersible transducer 2220 generates sound energy 140 at a sweeping frequency. Sound energy 140 propagates away from immersible transducer 2200 along each of directions 2230 and 2232. System 2200 may implement drive circuitry 130 as drive circuitry 1330. As discussed above in reference to FIG. 3B, the sweeping frequency of sound energy 140 causes decoherence of sound energy 140 and dispersion of sound energy 140 to the entire volume of blood 190 within vessel 110.

Figure 23A:
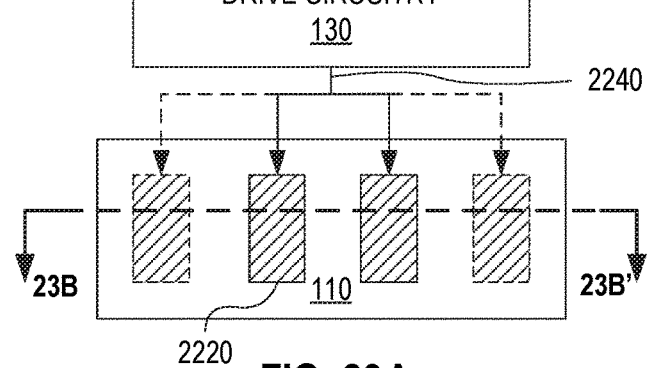
FIGS. 23A and 23B illustrate a system for imploding leukemia cells of a patient, using sound energy generated by a plurality of immersible transducers immersed in blood inside a vessel, according to an embodiment.
Figure 23B:
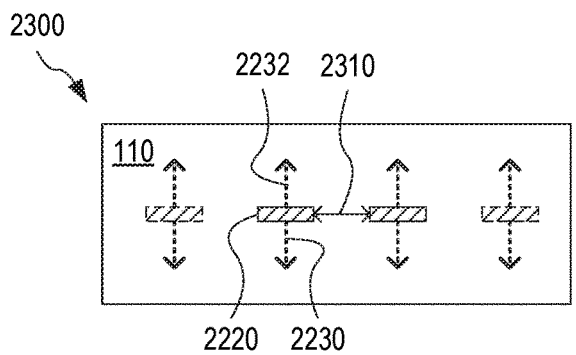

FIGS. 23A and 23B illustrate one exemplary system 2300 for imploding leukemia cells 192 of patient 180, using sound energy 140 generated by a plurality of immersible transducers 2220 immersed in blood 190 inside vessel 110. For clarity of illustration, not all immersible transducers 2220 are labeled in FIGS. 23A and 23B. Without departing from the scope hereof, system 2300 may include any number of immersible transducers 2220 greater than one. System 2300 is an embodiment of system 100. In one implementation, system 2300 is an embodiment of system 302. In another implementation, system 2300 is an embodiment of system 404. System 2300 may perform method 600. FIG. 23A shows system 2300 in a cross-sectional side view. FIG. 23B shows system 2300 in a cross-sectional top view taken along line 23B-23B' indicated in FIG. 23A. FIGS. 23A and 23B are best viewed together.

System 2300 includes vessel 110, at least two immersible transducers 2220 located inside vessel 110 for immersion into blood 190 within vessel 110, drive circuitry 130, and leads 2240 connecting immersible transducers 2220 to drive circuitry 130 (as discussed above in reference to FIG. 22). Each immersible transducer 2220 directs sound energy 140 along directions 2230 and 2232. The plurality of immersible transducers 2220 are arranged such that directions 2230 and 2232 for one immersible transducer 2220 is substantially parallel to directions 2230 and 2232 for every other immersible transducer 2220.

In one implementation, drive circuitry 130 is configured to sweep the frequency of the control signal(s) communicated to immersible transducers 2220, to sweep the frequency of sound energy 140 generated by each immersible transducer 2220. This implementation achieves decoherence of sound energy 140 and dispersion of sound energy 140 to the entire volume of blood 190 within vessel 110 in the same manner as discussed above in reference to FIGS. 3B and 22. This implementation may implement drive circuitry 130 as drive circuitry 1330.

In another implementation, drive circuitry 130 drives each immersible transducer 2220 at a constant frequency. However, the distance 2310 between adjacent immersible transducers 2220 is sufficiently small that sound energy 140 generated by adjacent immersible transducers 2220 couple with each other to decohere sound energy 140 and disperse sound energy 140 to the entire volume of blood 190 within vessel 110, as discussed above in reference to FIG. 4B for example. In this implementation, drive circuitry 130 may drive adjacent immersible transducers 2220 at different frequencies and/or phases to induce decoherence of sound energy 140 and dispersion of sound energy 140 to the entire volume of blood 190 within vessel 110, as discussed above in reference to FIGS. 4B and 4C. In one example of this implementation, drive circuitry 130 is implemented as drive circuitry 1530. In another example of this implementation, drive circuitry 130 is coupled to adjacent immersible transducers 2220 with opposite polarities.

In yet another implementation, drive circuitry 130 is configured to drive each immersible transducer 2220 at a sweeping frequency and is further configured to drive adjacent immersible transducers 2220 at different frequencies, phases, and/or sweep patterns. This implementation combines the sound energy decoherence and dispersion mechanism of the two implementations discussed immediately above, and further allows for sound energy decoherence and dispersion by applying different sweep patterns to adjacent immersible transducers 120 as discussed above in reference to FIG. 16. In one example of this implementation, drive circuitry 130 is implemented as drive circuitry 1530 with sweep unit 542. In another example this implementation, drive circuitry 130 is implemented as drive circuitry 1630.

Although not shown in FIGS. 23A and 23B, system 2300 may include mounting hardware for holding immersible transducers 2220 inside vessel 110, without departing from the scope hereof. In one embodiment, leads 2240 are integrated in such mounting hardware. Also, system 2300 may include fluid handling components such as discussed above in reference to FIG. 5, without departing from the scope hereof. Also without departing from the scope hereof, system 2300 may utilize a vessel 110 of shape different from that shown in FIG. 23, for example a cylindrical vessel.

Figure 24:
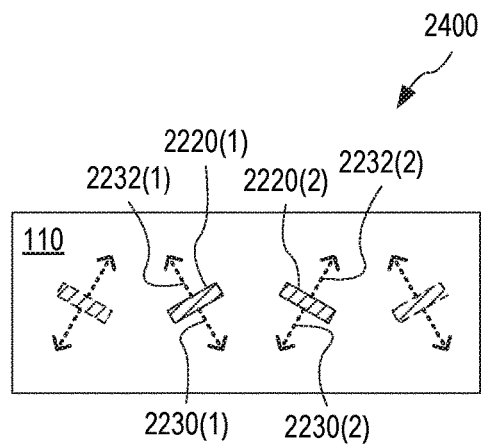
FIG. 24 illustrates another system for imploding leukemia cells of a patient, using sound energy generated by a plurality of immersible transducers immersed in blood inside a vessel, according to an embodiment.

FIG. 24 illustrates another exemplary system 2400 for imploding leukemia cells 192 of patient 180, using sound energy 140 generated by a plurality of immersible transducers 2220 immersed in blood 190 inside vessel 110. FIG. 24 shows system 2400 in the same cross-sectional top view as used for FIG. 23B. For clarity of illustration, not all immersible transducers 2220 are labeled in FIG. 24. Without departing from the scope hereof, system 2400 may include any number of immersible transducers 2220 greater than one. System 2400 is an embodiment of system 404. System 2400 may perform method 600.

System 2400 is similar to system 2300 except that adjacent immersible transducers 2220 direct sound energy 140 in intersecting directions. Thus, system 2400 inter-couples sound energy 140 generated by adjacent immersible transducers, to decohere sound energy 140 and disperse sound energy 140 to the entire volume of blood 190 within vessel 110, as discussed above in reference to FIG. 4C. Without departing from the scope hereof, sound energy 140 generated by one immersible transducer 2220 may intersect with sound energy 140 generated by another immersible transducer 2220 after reflection of sound energy off of a blood-to-solid or blood-to-air interface.

In an manner similar to that of system 2300, discussed above in reference to FIGS. 23A and 23B, system 2400 may further utilize frequency sweeping, and/or application of different frequencies, phases, and/or sweep patterns to adjacent immersible transducers 2220 to, at least potentially, improve the efficiency of decoherence of sound energy 140 and dispersion of sound energy 140 to the entire volume of blood 190 within vessel 110.

Figure 25:
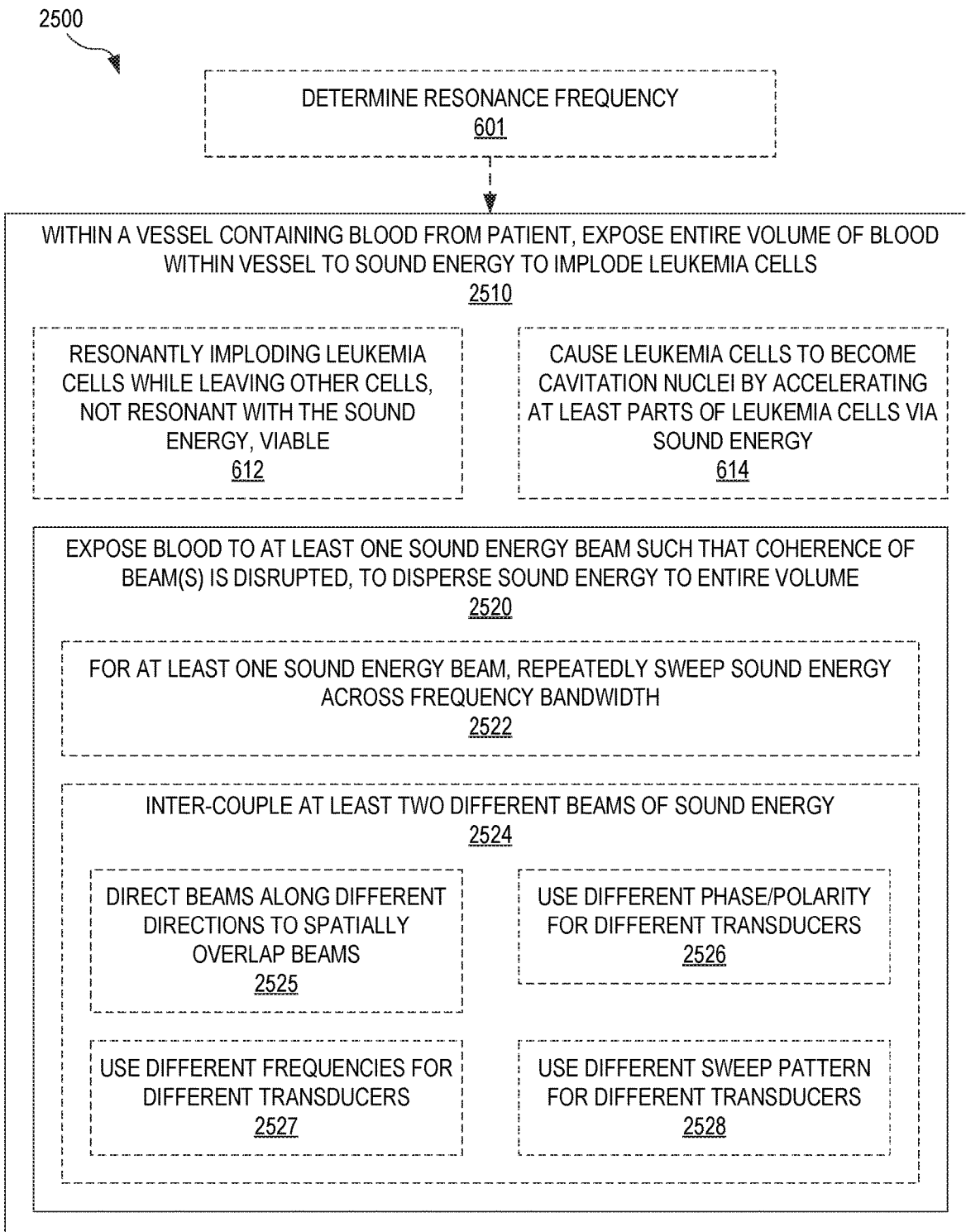
FIG. 25 illustrates another method for imploding leukemia cells in blood of a patient, according to an embodiment.

FIG. 25 illustrates one exemplary method 2500 for imploding leukemia cells 192 in blood 190 of patient 180. Method 2500 is an embodiment of method 600. Method 2500 is performed by an embodiment of system 100, for example.

Method 2500 includes a step 2510 of, within a vessel containing blood 190 from patient 180, exposing the entire volume of blood 190 to sound to implode leukemia cells 192. The sound energy is resonant with implosion of leukemia cells 192. Step 2510 is an embodiment of step 610 of method 600. Step 2510 may be implemented in step 732 of method 700. Method 2500 may further include step 601 to determine the resonance frequency for implosion of leukemia cells 192 prior to performing step 2510.

Step 2510 includes a step 2520 of exposing blood 190, within the vessel, to at least one sound energy beam such that the coherence of the sound energy beam is disrupted. The disruption of the coherence of the sound energy beam leads to dispersion of the sound energy to the entire volume of blood 190 within the vessel. In one example of step 2510, one or more transducers 120 of system 100 exposes blood 190 within vessel 110 to one or more beams 340 of sound energy 140 in such a manner that the coherence of beams 340 is disrupted to disperse sound energy 140 to the entire volume of blood 190 within vessel 110. Step 2510 includes one or both of steps 2522 and 2524.

Step 2522 repeatedly sweeps the frequency of the sound energy of at least one beam across a frequency bandwidth to disrupts the coherence of the at least one beam, so as to disperse the sound energy to the entire volume of blood 190 within the vessel. The frequency bandwidth encompasses the resonance frequency for implosion of leukemia cells 192. In one example of step 2522, drive circuitry 130 implements sweep unit 542 to drive one or more transducers 120 with a sweep pattern as shown in diagram 350 of FIG. 3A. Embodiments of method 2500 that include step 2522 may be performed by any one of systems 300, 302, 800, 900, 1300, 1400 (when including sweep unit 542), 1500 (when including sweep unit 542), 1600, 1700 (when including sweep unit 542), 1800 (when including sweep unit 542), 1900 (when including sweep unit 542), 2000, 2100, 2200, 2300, and 2400.

Step 2524 inter-couples at least two different beams of sound energy to disrupt the coherence of the beams, so as to disperse the sound energy to the entire volume of blood 190 within the vessel. In one example of step 2524, beams 340 of sound energy 140 generated by two transducers 120, and propagating in blood 190 inside vessel 110, inter-couple to disrupt the coherence of these beams 340, so as to disperse sound energy 140 to the entire volume of blood 190 within vessel 110. Embodiments of method 2500 that include step 2524 may be performed by any one of systems 400, 402, 404, 900, 1700, 1800, 1900, 2000, 2100, 2300, and 2400.

Embodiments of method 2500 that include both step 2522 and 2524 may be performed by any one of systems 1700, 1800, 1900, 2000, 2100, 2300, and 2400.

In an embodiment, step 2524 includes a step 2525 of directing beams of sound energy along different directions to spatially overlap the beams. In one example of step 2525, two transducers 120 of system 100 are arranged to generate respective intersecting beams 340. Embodiments of method 2500 that include step 2525 may be performed by any one of systems 400, 404, 900 1700, 1800, 1900, 2000, 2100, and 2400.

In an embodiment, step 2524 includes a step 2526 of using different phase and/or polarity for different transducers. In one example of step 2526, two adjacent transducers 120 of system 100 oscillate out of phase with each other. Embodiments of method 2500 that include step 2526 may be performed by any one of systems 402, 800, 900, 1400, 1500, 1600, 1800, 1900, 2000, 2100, 2300, and 2400.

In an embodiment, step 2524 includes a step 2527 of using different frequencies for different transducers. In one example of step 2527, drive circuitry 130 of system 100 drives adjacent transducers 120 at different frequencies. At least one of these different frequencies is resonant with implosion of leukemia cells 192. Optionally, each of the different frequencies is substantially resonant with implosion of leukemia cells 192. Embodiments of method 2500 that include step 2527 may be performed by any one of systems 402, 800, 900, 1500, 1900, 2100, 2300, and 2400.

In an embodiment, step 2524 includes a step 2528 of using different sweep patterns for different transducers. In one example of step 2528, drive circuitry 130 of system 100 repeatedly sweeps the frequency of sound energy 140 generated by transducers 120, and performs this frequency sweeping with different sweeping patterns applied to adjacent transducers 120. Embodiments of method 2500 that include step 2528 may be performed by any one of systems 300, 800, 900, 1600, 2000, 2100, 2300, and 2400.

In an embodiment, step 2524 simultaneously performs two or more of steps 2525, 2526, 2527, and 2528.

Optionally, step 2510 further includes one or both of steps 612 and 614 of method 600.

Figure 26:
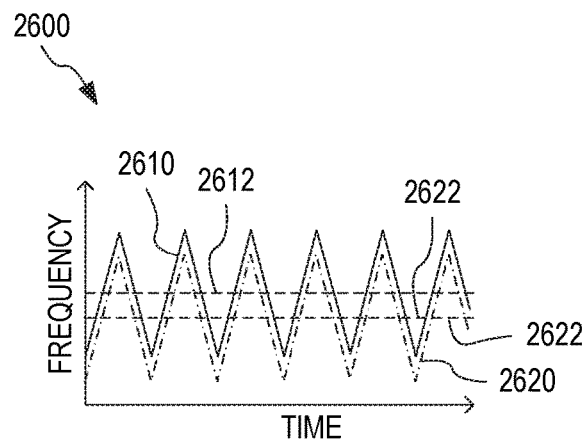
FIG. 26 is a diagram illustrating one exemplary set of drive signals used in the system of FIG. 1 when performing an embodiment of the method of FIG. 25.

FIG. 26 is a diagram 2600 illustrating one exemplary set of drive signals 2610 and 2620 generated by drive circuitry 130 and applied to two respective transducers 120 of system 100 when system 100 simultaneously performs steps 2522 and 2527 of method 2500. Each of drive signals 2610 and 2620 repeatedly sweeps the frequency applied to the respective transducer 120. Drive signal 2610 has center frequency 2612 and drive signal 2620 has center frequency 2622. Each of center frequencies 2612 and 2622 is an example of center frequency 352. The difference between center frequencies 2612 and 2622 is sufficient to at least aid decoherence of sound energy 140 and dispersion of sound energy 140 to the entire volume of blood 190 within vessel 110. In one example, both center frequency 2612 and center frequency 1622 are resonant with imploding leukemia cells 192. In another example, only one of center frequencies 2612 and 2622 is resonant with imploding leukemia cells 192.

Figure 27:
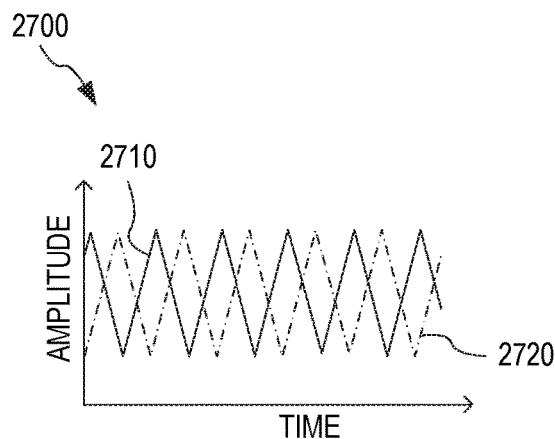
FIG. 27 is a diagram illustrating another exemplary set of drive signals used in the system of FIG. 1 when performing another embodiment of the method of FIG. 25.

FIG. 27 is a diagram 2700 illustrating one exemplary set of drive signals 2710 and 2720 generated by drive circuitry 130 and applied to two respective transducers 120 of system 100 when system 100 performs step 2526 of method 2500. Diagram 2700 shows the amplitude of drive signals 2710 and 2720 as a function of time. The amplitude is a voltage applied across a respective transducer 120, for example. Drive signal 2710 is out of phase with drive signal 2720. In one example, drive signals 2710 and 2720 are out of phase by 180 degrees. In this example, drive signals 2710 and 2720 may be generated from a common drive signal by coupling the two transducers 120 with opposite polarities. In another example, drive signals 2710 and 2720 are out of phase by any number of degrees. In this example, drive signals 2710 and 2720 may be generated by two different generators 530. Alternatively, the two transducers 120 may be coupled to the same generator 530 with a phase shift applied to the drive signal generated by generator 530 and communicated to one of transducers 120.

Figure 28:
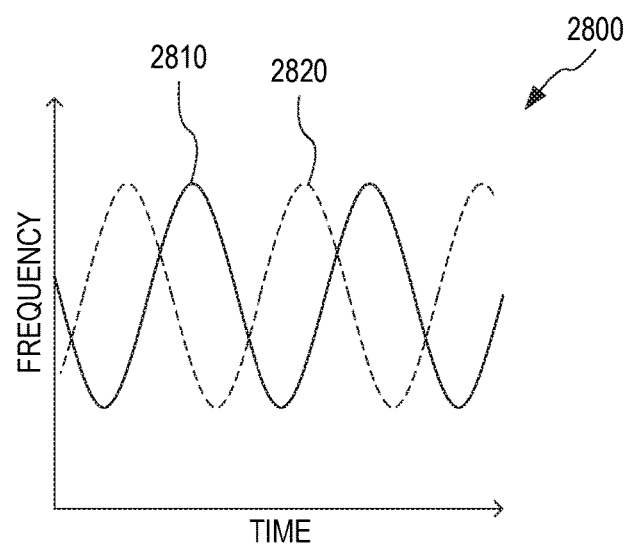
FIG. 28 is a diagram illustrating yet another exemplary set of drive signals used in the system of FIG. 1 when performing yet another embodiment of the method of FIG. 25.

FIG. 28 is a diagram 2800 illustrating one exemplary set of out-of-phase sweep patterns 2810 and 2820 generated by drive circuitry 130 and applied to two respective transducers 120 of system 100 when system 100 performs step 2528 of method 2500. The phase of sweep pattern 2810 is shifted from the phase of sweep pattern 2820 such that transducers 120 generally produce sound energy 140 having different respective frequencies.

Figure 29:
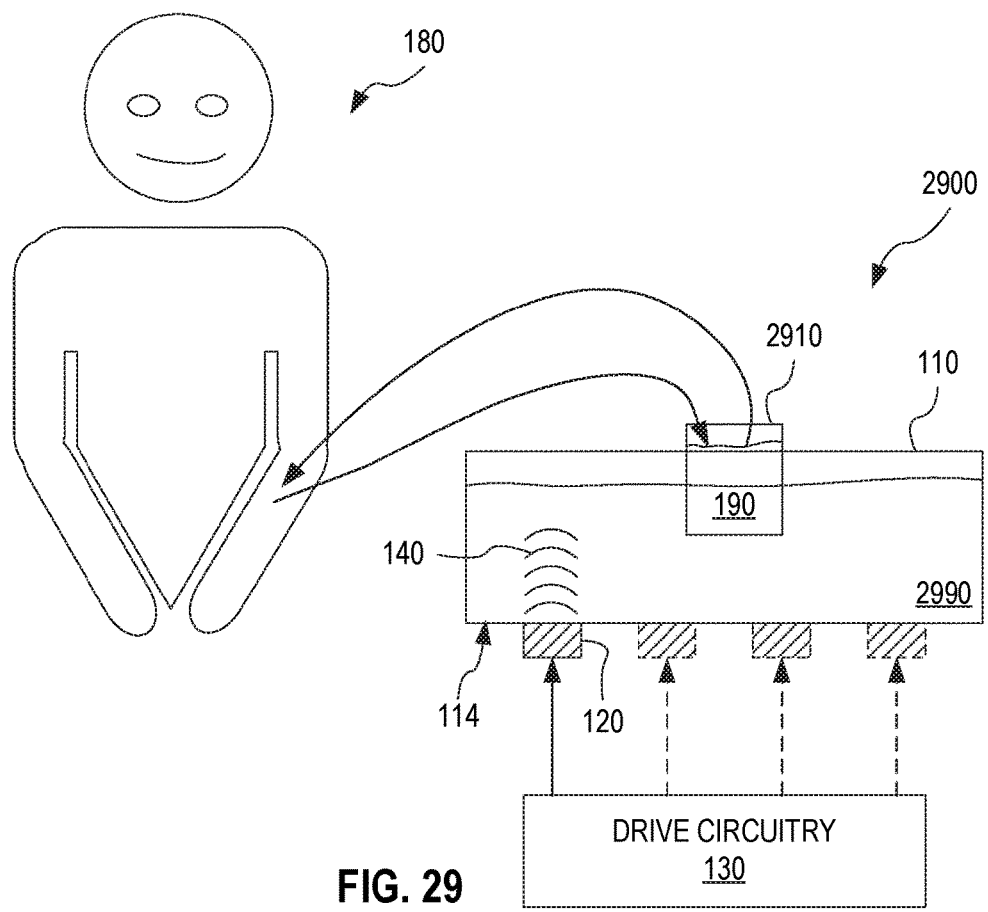
FIG. 29 illustrates a system for imploding leukemia cells of a patient, which utilizes nested vessels, according to an embodiment.

FIG. 29 illustrates one exemplary system 2900 for imploding leukemia cells 192 of patient 180, which utilizes nested vessels. System 2900 is an extension of system 100, wherein blood 190 is located in an inner vessel 2910 that is placed in contact with a liquid 2990 held by vessel 110. System 2900 includes one or more transducers 120 and drive circuitry 130. Vessel 110, transducers 120, and drive circuitry 130 are operated in the same manner as discussed above in reference to FIG. 1 to decohere sound energy 140 and disperse sound energy 140 to the entire volume of liquid 2990 within vessel 110. By virtue of the contact between vessel 2910 and liquid 2990, system 2900 transmits sound energy 140 to the entire volume of blood 190 within inner vessel 2910, so as to implode leukemia cells 192 in blood 190 as discussed above in reference to FIGS. 1 and 2.

Vessel 110, transducer(s) 120, and drive circuitry 130 may be configured according to any of the embodiments discussed above in reference to FIGS. 1, 3A-4C, 5, and 8A-24. System 2900 may include a plurality of transducers 120 or only a single transducer 120 and is configured such that a beam 340 of sound energy 140 generated by one transducer 120 couples with itself and/or a beam 340 of sound energy 140 generated by other transducers 140 to disrupt the coherence of such beam(s) 340. This not only results in the dispersion of sound energy 140 to the entire volume of liquid 2990 but also produces incoherent sound energy 140 incident on inner vessel 2910. At least a portion of this incoherent sound energy 140 is transmitted into blood 190 in inner vessel 2910 and is dispersed to the entire volume of blood 190 within inner vessel 2910.

Liquid 2990 may be conditioned for efficient decoherence of beam(s) 340 and efficient dispersion of sound energy 140 throughout the entire volume of liquid 2990 within vessel 2990. Since liquid 2990 is separated from blood 190, this conditioning may be done without compromising parameters of blood 190. In addition, blood 190 is not in direct contact with any portion of liquid 2990 or vessel 110, thus eliminating the need for decontamination of vessel 110. Inner vessel 2910 may be an inexpensive, disposable container or a container designed for easy decontamination, for example through steam sterilization. In operation, inner vessel 2910 may be filled with blood 190 or only partly filled with blood 190. Likewise, in operation, vessel 110 may be filled with liquid 2990 or only partly filled with liquid 2990.

In an experimental demonstration, a 400 milliliter Pyrex beaker containing about 200 milliliters of cold deionized water with high gas content was placed inside an embodiment of vessel 110 filled with hot degased deionized water. The beaker is an example of inner vessel 2910 and the hot degased deionized water is an example of liquid 2990. It is relatively difficult to induce transient cavitation in cold water with high gas content, and this liquid served as a model for blood 190. On the other hand, it is easier to induce transient cavitation in hot degased water. In this demonstration, a plurality of transducers 120 coupled to vessel 110 generated sound energy 140 at a sweeping frequency with center frequency 352 being 440 kHz and frequency bandwidth 354 being 5 kHz. Vessel 110 and transducers 120 were configured according to the embodiment of system 300. Transient cavitation was evident throughout the entire volume of liquid 2990 and also throughout the entire volume of the water in the beaker, even though the wall thickness of the beaker did not match an integer number of half wavelengths of sound energy 140 at 440 kHz. A hydrophone measured a signal of 19.5 volts rms at location 312 (see FIG. 3A) and a signal of 18.7 volts rms at location 314, which quantitatively demonstrates efficient decoherence of sound energy 140 and dispersion of sound energy 140 throughout the entire volume of liquid 2990. A hydrophone placed in the water in the beaker measured a signal of 19.2 volts rms, which quantitatively demonstrates efficient transmission of sound energy 140 through the wall of the beaker to the water inside the beaker. All hydrophone measurements measured a frequency of 440 kHz. Thus, transmission of sound energy 140 into the water of the beaker maintains the original frequency of 440 kHz.

For comparison, these measurements were repeated without frequency sweeping. In this non-sweeping case, transient cavitation was visibly present only in beams 340 over transducers 120, e.g., at location 312. A hydrophone measured a signal of 19.5 volts rms at location 312, a signal of 0.9 volts rms at location 314, and a signal of 0.9 volts rms in the water in the beaker.

This experiment demonstrates the feasibility of using system 2900 to efficiently transmit sound energy 140 to blood 190 within inner vessel 2910 to implode leukemia cells 192 in blood 190. The experiment also demonstrates the significance of decohering sound energy 140 to efficiently transmit sound energy 140 to blood 190 within inner vessel 2910.

In an embodiment, inner vessel 2910 has a wall thickness, at least for a wall contacting liquid 2990, which matches an integer number of half wavelengths of sound energy 140 resonant with implosion of leukemia cells. In this embodiment, sound energy 140 may be resonantly transmitted by the wall of inner vessel 2910 to blood 190.

Although not shown in FIG. 29, system 2900 may include fluid handling components to extract blood 190 from patient 180, flow blood 190 through inner vessel 2910 for treatment by system 2900, and return blood 190 to patient 180.

Without departing from the scope hereof, system 2900 may be provided without inner vessel 2910, in which case inner vessel 2910 may be supplied by a third party. Likewise, vessel 110, inner vessel 2910 (if included), transducers 120, and plate 520 (if included), and optionally other mounting hardware may form a stand-alone system configured to operate in conjunction with third party drive circuitry 130 to implode leukemia cells 192 in blood 190, without departing from the scope hereof.

Figure 30:
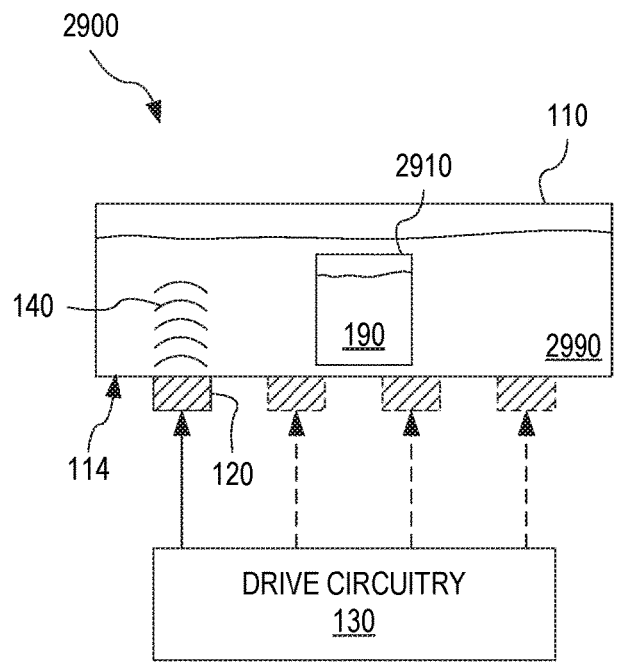
FIG. 30 illustrates an exemplary implementation of the system of FIG. 29, wherein an inner vessel is entirely submerged in liquid held by a main vessel.

FIG. 30 illustrates an implementation of system 2900, wherein inner vessel 2910 is entirely submerged in liquid 2990. This implementation of system 2900 functions as discussed above in reference to FIG. 29.

Figure 31:
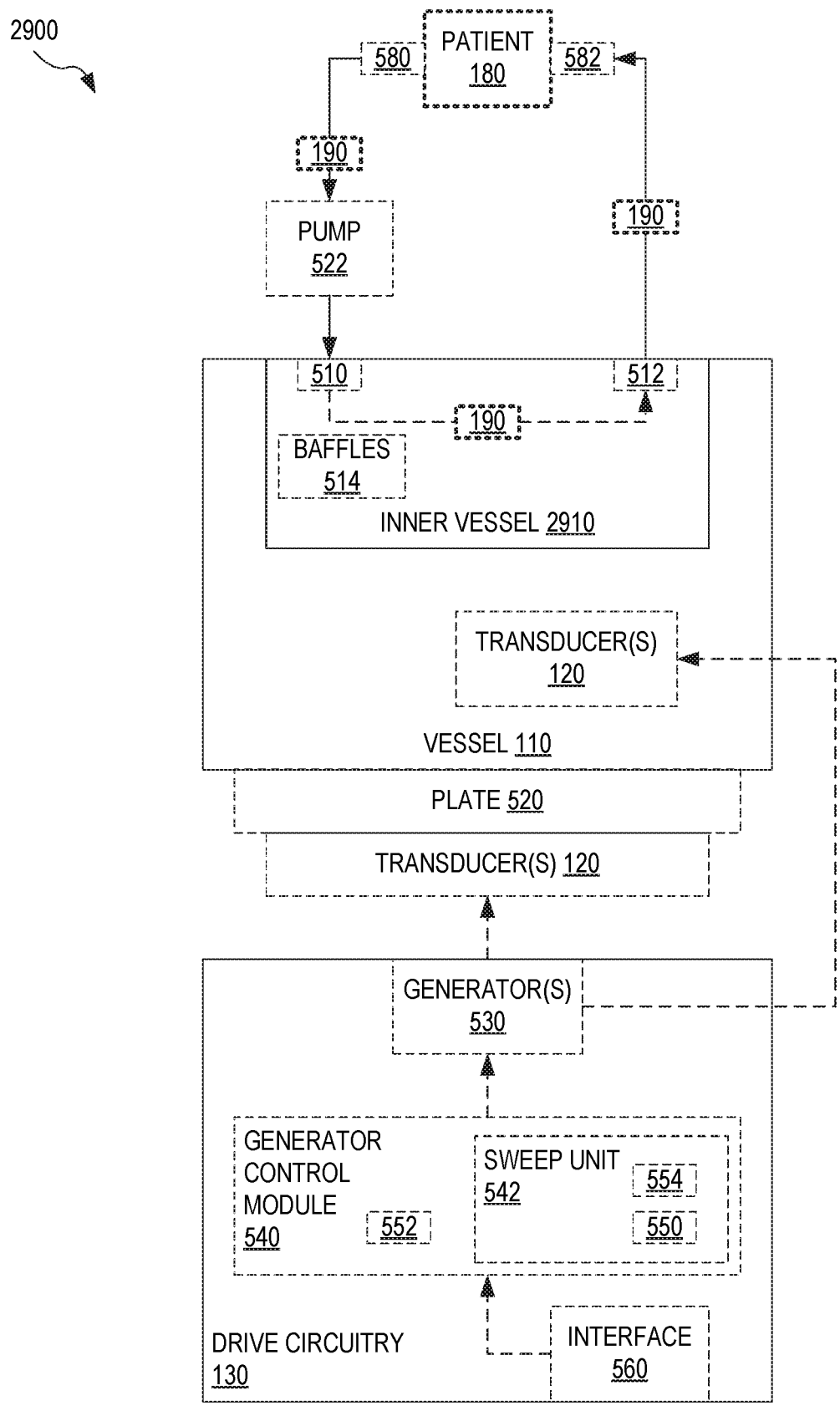
FIG. 31 is a block diagram showing the system of FIG. 29 in further detail, according to an embodiment.

FIG. 31 is a block diagram showing system 2900 in further detail. System 2900 includes vessel 110, transducer(s) 120, and drive circuitry 130, configured as discussed above in reference to FIG. 5. System 2900 may further include plate 520, as discussed above in reference to FIG. 5. In addition, system 2900 may include fluid handling components configured to circulate blood 190 out of patient 180, through inner vessel 2910, and return blood 190 to patient 180. These fluidic handling components may include one or more of catheter 580, catheter 582, inlet 510, outlet 512, and pump 522, configured as discussed above in reference to FIG. 5, except that inlet 510 and outlet 512 are implemented in inner vessel 2910 such that blood 190 flows through inner vessel 2910 instead of vessel 110. Optionally, inner vessel 2910 implements baffles 514 to extend the flow path of blood 190 through inner vessel 2910.

Figure 32:
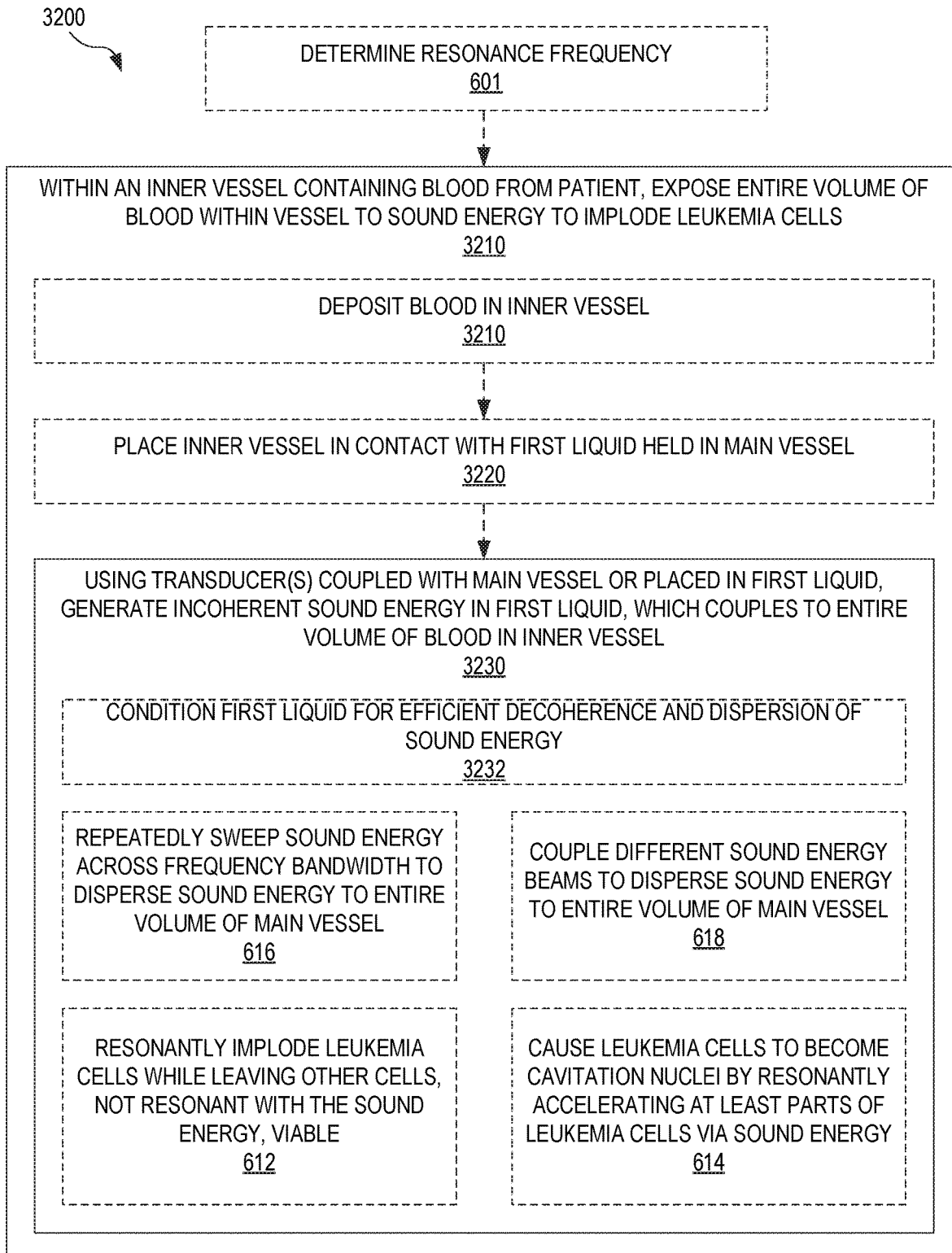
FIG. 32 illustrates a method for imploding leukemia cells in blood of a patient, which utilizes nested vessels, according to an embodiment.

FIG. 32 illustrates one exemplary method 3200 for imploding leukemia cells 192 in blood 190 of patient 180, which utilizes nested vessels. Method 3200 is an extension of method 600 and may be performed by system 2900.

In a step 3210, method 3200 treats blood 190 located within an inner vessel that is external to patient 180. The inner vessel is in contact with a first liquid contained by a main vessel. The main vessel is also external to patient 180.

Step 3210 exposes the entire volume of blood 190, within the inner vessel, to sound energy to implode leukemia cells 192 in blood 190. The sound energy is resonant with implosion of leukemia cells 192. Step 3210 includes a step 3230 of using one or more transducers, coupled with the main vessel or placed in the first liquid, to generate incoherent sound energy in the first liquid, which couples to the entire volume of blood 190 within the inner vessel. Step 3230 uses the transducers to generate sound energy and deliver the sound energy to the first liquid in such a manner that the sound energy is incoherent. In one example of step 3230, performed by system 2900, drive circuitry 130 drives transducer(s) 120 with an electric drive signal having frequency resonant with implosion of leukemia cells 192 to generate sound energy 140 having this resonance frequency. Transducer(s) 120 delivers sound energy 140 to liquid 2990, wherein sound energy decoheres, for example through one or more of the decoherence mechanisms discussed above in reference to FIGS. 3A-4C. The resulting incoherent sound energy 140 is transmitted from liquid 2990 to the entire volume of blood 190 within inner vessel 2910.

In an embodiment, step 3210 also includes one or both of steps 3210 and 3220. Step 3210 deposits blood 190 in the inner vessel. In one example of step 3210, pump 522 pumps blood 190 out of patient 180 via catheter 580 to deposit blood 190 in inner vessel 2910. Pump 522 may maintain pumping of blood 190 to circulate blood 190 through inner vessel. Step 3220 places the inner vessel in contact with the first liquid in the main vessel. In one example of step 3220, inner vessel 2910 is placed in contact with liquid 2990 inside vessel 110. Inner vessel 2910 may be fully submerged in liquid 2990, as shown in FIG. 30. Without departing from the scope hereof, step 3220 may be performed before step 3210, or steps 3210, 3220, and 3230 may be performed concurrently.

In one embodiment, step 3230 includes step 616 applied to the main vessel and the first liquid disposed therein. In another embodiment, step 3230 includes step 618 applied to the main vessel and the first liquid disposed therein. In yet another embodiment, step 3230 includes both of steps 616 and 618 but applied to the main vessel and the first liquid disposed therein. In method 3200, each of steps 616 and 618 serves to decohere the sound energy in the first liquid to ensure that the sound energy is efficiently transmitted to the entire volume of blood 190 in the inner vessel.

Optionally, step 3230 includes a step 3232 of conditioning the first liquid for efficient decoherence and dispersion of the sound energy. In one example of step 3232, the temperature of liquid 2990 is raised above room temperature, for example to a temperature in the range between 100 and 150 degrees Fahrenheit. Alternatively, or in combination therewith, liquid 2990 is degased.

In an embodiment, step 3230 implements one of both of steps 612 and 614 of method 600.

Step 3210 may be preceded by step 601 of method 600 to determine the resonance frequency for implosion of leukemia cells 192.

Figure 33:
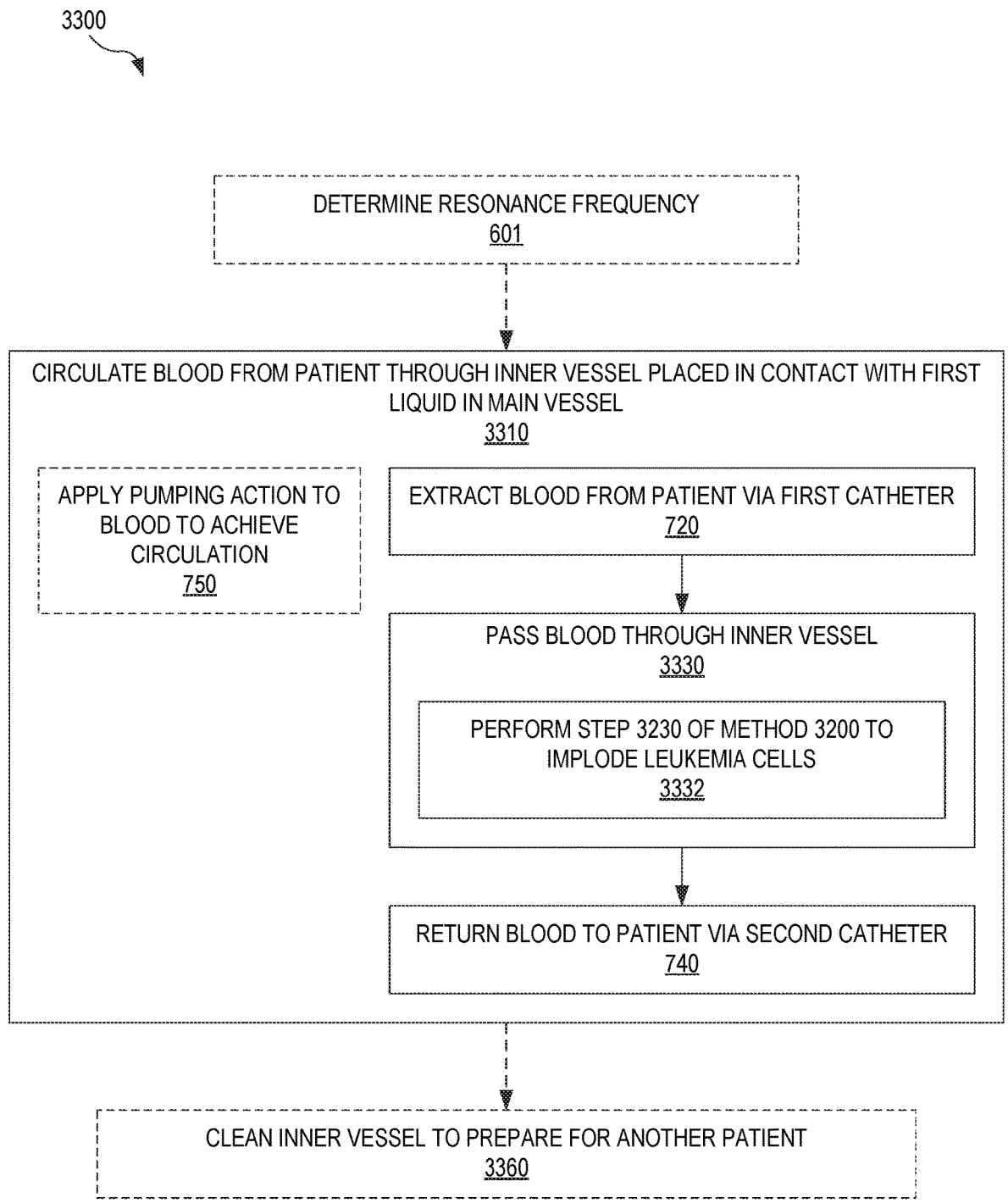
FIG. 33 illustrates a method for circulating blood out of a patient and through a nested vessel system to implode leukemia cells in the blood before returning the blood to the patient, according to an embodiment.

FIG. 33 illustrates one exemplary method 3300 for circulating blood 190 out of patient 180 and through a nested vessel system to implode leukemia cells 192 in blood 190 before returning blood 190 to patient 180. Method 3300 is an embodiment of method 3200 and is an extension of method 700. Method 3200 is performed by system 2900, for example.

A step 3310 circulates blood 190 from patient 180 through an inner vessel that is in contact with a first liquid disposed in a main vessel. Both the inner vessel and the main vessel are external to patient 180. Step 3310 is an embodiment of step 710 and includes steps 720, 3330, and 740. Step 3310 may further include step 750. Step 3330 is an embodiment of step 730. Step 3330 passes blood 190 through the inner vessel. In one example of step 3330, pump 522 pumps blood 190 to pass blood 190 through inner vessel 2910. Step 3330 includes a step 3332 of performing step 3230 of method 3200 to implode leukemia cells 192 in blood 190.

Method 3300 may include performing step 601 of method 600 prior to performing step 3310, to determine the resonance frequency for implosion of leukemia cells 192.

In one embodiment, method 3300 includes a step 3360 of cleaning the inner vessel used in step 3310 to prepare the inner vessel for another patient 180. Step 3360 may utilize methods known in the art for decontaminating medical equipment, such as steam sterilization. In another embodiment, the inner vessel is a disposable vessel that is discarded after a use on a single patient. In this embodiment, method 3300 does not include step 3360.

Figure 34A:
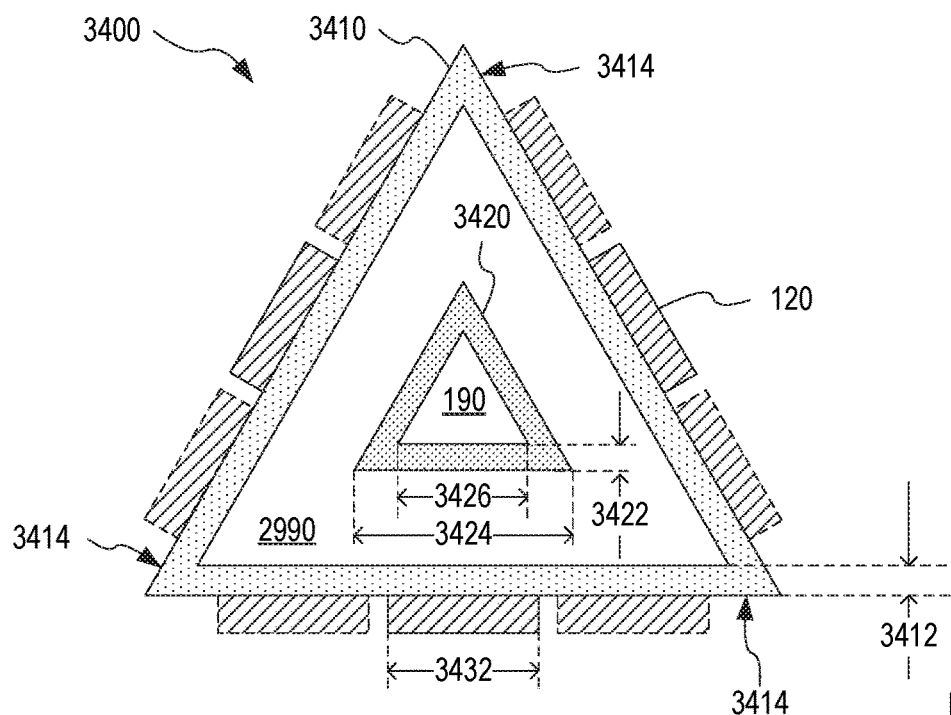
FIGS. 34A and 34B illustrate a nested-vessel system, according to an embodiment.
Figure 34B:
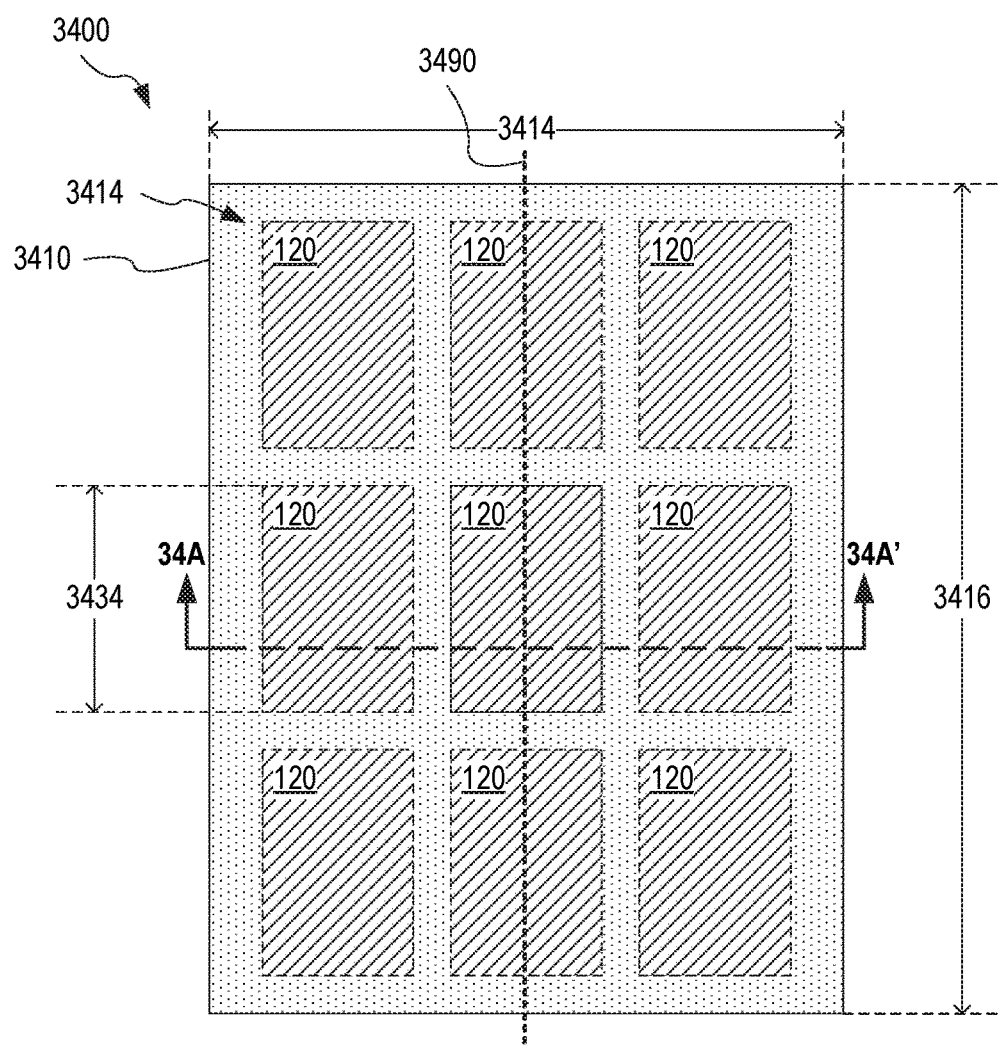

FIGS. 34A and 34B illustrate one exemplary nested-vessel system 3400. FIG. 34A shows a cross-sectional view of nested-vessel system 3400. FIG. 34B shows a side view of nested-vessel system 3400. The cross-section shown in FIG. 34A is taken along line 34A-34A' of FIG. 34B. FIGS. 34A and 34B are best viewed together.

Nested-vessel system 3400 is an embodiment of a portion of system 2900. Vessel 110, inner vessel 2910, and transducer(s) 120 of system 2900 may be configured according to the embodiment of nested-vessel system 3400. Nested-vessel system 3400 includes a vessel 3410, an inner vessel 3420, and a plurality of transducers 120 coupled to outside surfaces 3414 of respective walls of vessel 3410. Vessel 3410 is an embodiment of vessel 110, which implements a plurality of plates 520. Inner vessel 3420 is an embodiment of inner vessel 2910.

Each of vessels 3410 and 3420 is in the shape of an elongated prism with a triangular cross section (shown in FIG. 34A) perpendicular to the elongation axis 3490. The cross section of inner vessel 3420 is smaller than that of vessel 3410, and inner vessel 3420 is nested inside vessel 3410. Without departing from the scope hereof, the cross section of each of vessel 3410 and inner vessel 3420 may be rectangular, hexagonal, or another polygonal shape.

Each side of vessel 3410, parallel to elongation axis 3490, is coupled with at least one transducer 120. FIGS. 34A and 34B show that each such side is equipped with a 3×3 array of transducers 120. However, each such side may be equipped with a smaller or larger number of transducers 120, without departing from the scope hereof. Furthermore, not all sides need to have the same number of transducers 120. For clarity of illustration, not all transducers 120 are labeled in FIG. 34A.

At least in areas coupled to a transducer 120, vessel 3410 has wall thickness 3412. Wall thickness 3412 matches an integer number of half wavelengths of sound energy 140 resonant with implosion of leukemia cells 192. Thus, vessel 3410 resonantly couples sound energy 140 from transducers 120 to liquid 2990. Inner vessel 3420 has wall thickness 3422. In one example, wall thickness 3412 is about 6 millimeters. Optionally, wall thickness 3422 matches an integer number of half wavelengths of sound energy 140. For example, when inner vessel 3420 is made of stainless steel and wall thickness 3422 is 6.214 millimeters, wall thickness 3422 matches three half wavelengths of sound energy 140 with a frequency of 1.4 MHz. However, as discussed above in reference to FIG. 29, wall thickness 3422 need not match an integer number of half wavelengths of sound energy 140 for efficient transmission of incoherent sound energy 140 from liquid 2990 to the entire volume of blood 190 within inner vessel 3420.

In an embodiment, each side of vessel 3410, parallel to elongation axis 3490, has external extents 3414 and 3416. External extent 3414 may be in the range between 10 and 20 centimeters (cm), for example about 14 cm. External extent 3416 may be in the range between 20 and 40 cm, for example about 25 cm. In an embodiment, each side of inner vessel 3410, parallel to elongation axis 3490, has external and internal extents 3424 and 3426, respectively, in dimension orthogonal to elongation axis 3490. External extent 3424 may be in the range between 3 and 10 cm, for example about 5 cm. Internal extent 3424 may be in the range between 2 and 8 cm, for example about 3.8 cm. The internal extent of inner vessel 3420 along elongation axis 3490 may be in the range from about 3 to 20 cm, for example such that inner vessel 3420 may hold between 2% and 10% of the volume of blood 190 of patient 180.

The number of transducers 120 coupled to vessel 3410 and the size of each such transducer 120 may be selected to provide a level of sound energy 140 sufficient to implode leukemia cells 192 in blood 190 within the entire volume of vessel 3420. In an embodiment, each side of vessel 3410, parallel to elongation axis 3490, is coupled to nine transducers 120 arranged in a 3×3 array, and each transducer has extents 3432 and 3434. Extent 3432 may be in the range between 2 and 4 cm, for example about 2.9 cm. Extent 3434 may be in the range between 5 and 10 cm, for example about 6.7 cm.

In an alternate embodiment, not shown in FIGS. 34A and 34B, the cross section of inner vessel 3420 is round, for example circular.

Without departing from the scope hereof, system 2900 may be provided without inner vessel 2910, in which case inner vessel 2910 may be supplied by a third party.

Figure 35A:
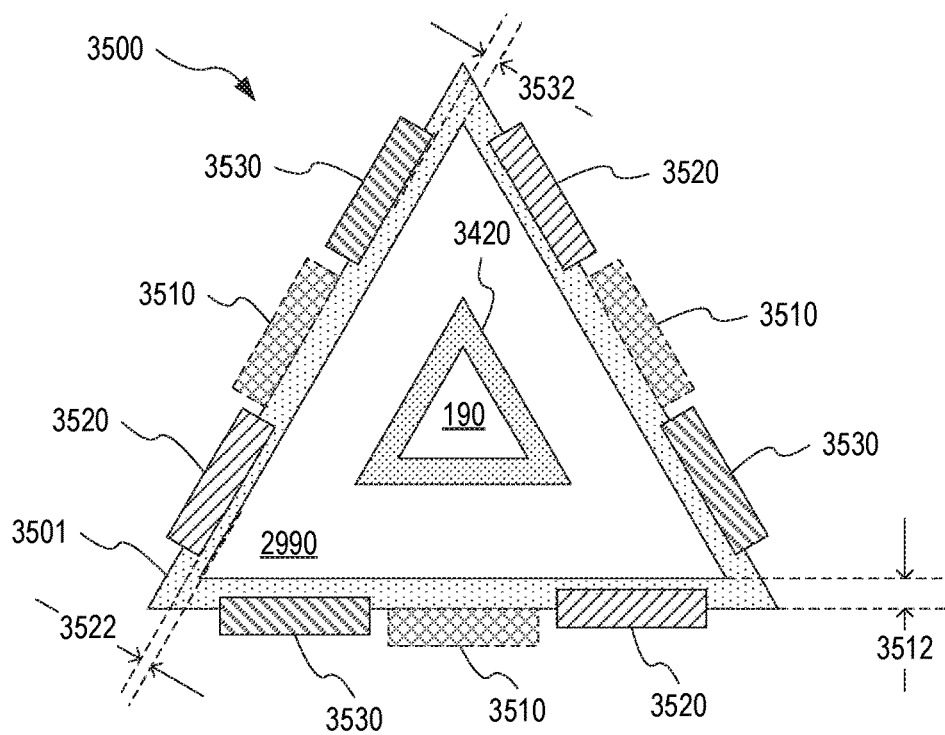
FIGS. 35A and 35B illustrate a multi-frequency, nested-vessel system, according to an embodiment.
Figure 35B:
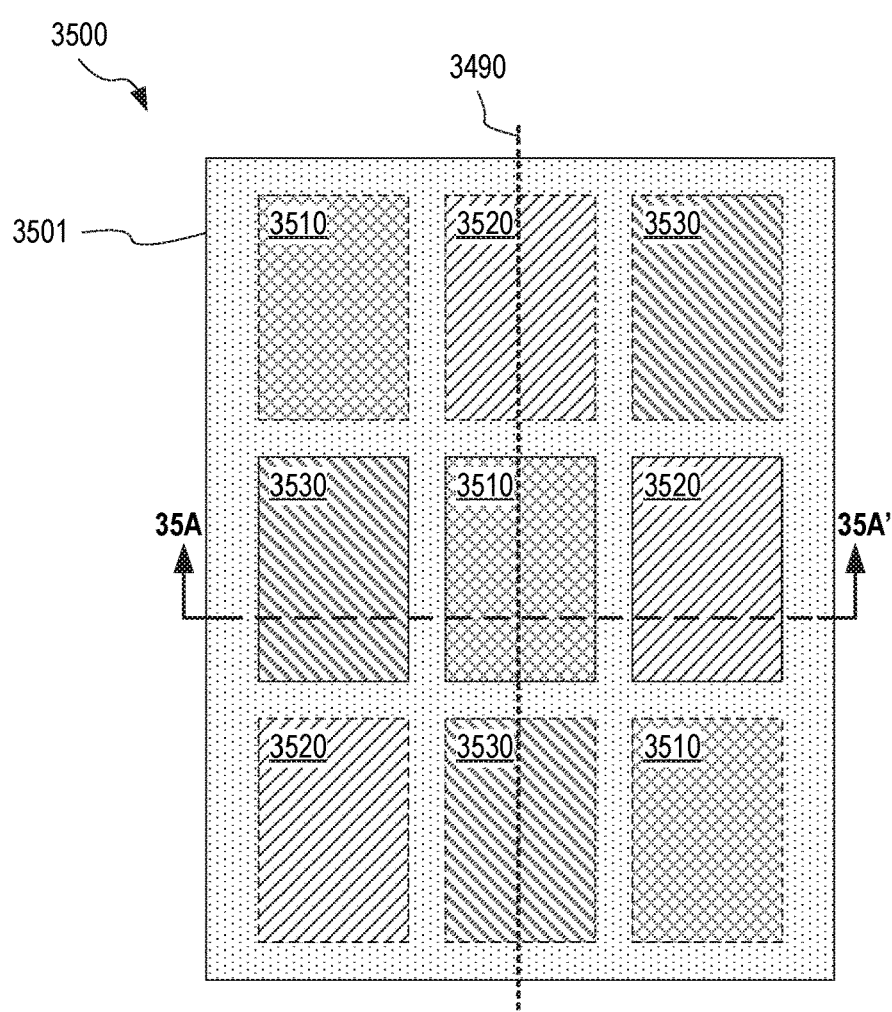

FIGS. 35A and 35B illustrate one exemplary multi-frequency, nested-vessel system 3500. FIG. 35A shows a cross-sectional view of system 3500. FIG. 35B shows a side view of system 3500. The cross-section shown in FIG. 35A is taken along line 35A-35A' of FIG. 35B. FIGS. 35A and 35B are best viewed together.

System 3500 is an embodiment of a portion of system 2900. Vessel 110, inner vessel 2910, and transducer(s) 120 of system 2900 may be configured according to the embodiment of system 3500. System 3500 is similar to system 3400, except for implementing a plurality of different types of transducers, each configured to resonantly generate sound energy 140. By virtue of these different frequencies, system 3500 is capable of imploding a respective plurality of different classes of leukemia cells 192 characterized by different respective sizes. In the example shown in FIGS. 35A and 35B, system 3500 includes a plurality of each of three different types of transducers 3510, 3520, and 3530. Transducers 3510, 3520, and 3530 are configured to resonantly generate sound energy 140 at three different frequencies, respectively. Thus, system 3500, as shown in FIGS. 35A and 35B, is capable of imploding three different classes of leukemia cells 192. Each transducer 3510, 3520, and 3530 is an embodiment of transducer 120.

In order to resonantly couple sound energy 140 generated by each transducer 3510, 3520, and 3530 into liquid 2990, system 3500 implements a vessel 3501 that has a plurality of wall thicknesses. Vessel 3501 is an implementation of vessel 3410 extended to resonantly couple sound energy 140 of a plurality of frequencies into liquid 2990. Each portion of vessel 3501, coupled to a transducer 3510, has wall thickness 3512. Each portion of vessel 3501, coupled to a transducer 3520, has wall thickness 3522. Each portion of vessel 3501, coupled to a transducer 3530, has wall thickness 3532.

Without departing from the scope hereof, system 3500 may be provided without inner vessel 3420, in which case inner vessel 3420 may be supplied by a third party.

The cost of manufacturing vessel 3501, transducers 3510, 3520, and 3520, as well as associated drive circuitry 130 may exceed the cost of manufacturing a single-frequency system. However, since blood 190 does not contact vessel 3501 and since system 3500 may be applicable to treatment of a greater variety of patients 180, system 3500 may be used many times to treat many different patients 180. Without departing from the scope hereof, system 100 may be extended in a similar manner to include a plurality of types of transducers 120, each configured to resonantly generate sound energy 140 at a different frequency, to implode a respective plurality of classes of leukemia cells 192.

Figure 36:
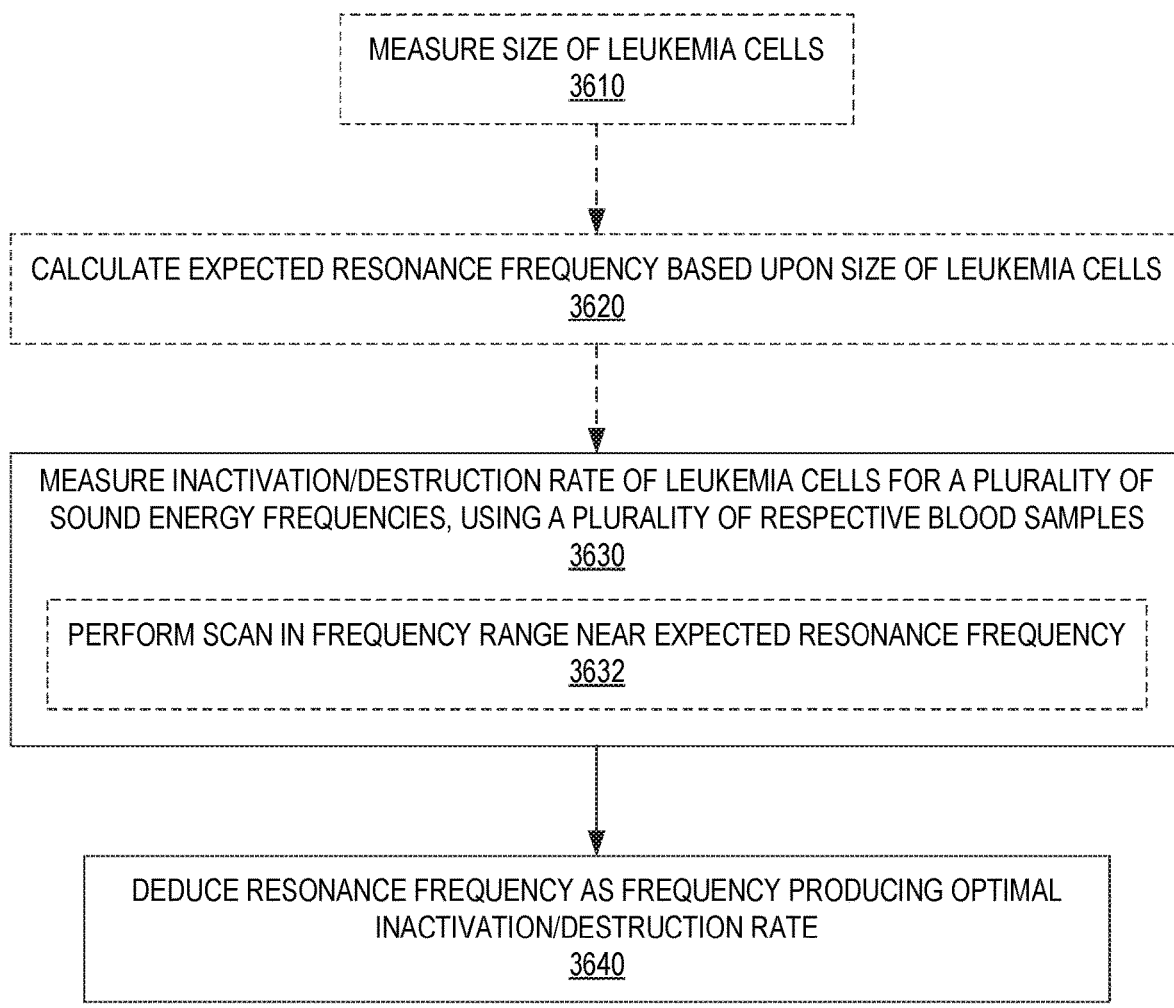
FIG. 36 illustrates a method for determining a resonance frequency for imploding leukemia cells in blood, according to an embodiment.

FIG. 36 illustrates one exemplary method 3600 for determining the resonance frequency for imploding leukemia cells 192 in blood 190. Method 3600 is an embodiment of step 601 of method 600.

In a step 3630, method 3600 measures the implosion rate of leukemia cells 192 for a plurality of sound energy frequencies. Step 3630 utilizes a plurality of blood samples and applies each sound energy frequency to a respective one of the blood samples. In one example of step 3630, a sample of blood 190 from patient 180 is disposed in vessel 110, and transducer(s) 120 generates sound energy 140 at the test frequency assigned to the sample. The implosion rate is measured for this sample, for example using techniques known in the art. This process is repeated for each one of the plurality of samples of blood 190 from patient 180. When disposing the sample of blood 190 in vessel 110, the sample may be contained in a test tube that is immersed in a coupling liquid, water for example, inside vessel 110. This approach may reduce the amount of blood 190 required to perform step 3630. Optionally, different transducers 120 are used for at least some of the different frequencies to ensure resonant operation of transducers 120 at all frequencies tested.

In a step 3640, method 3600 deduces the optimal resonance frequency for implosion of leukemia cells 192 from the measurements made in step 3630. In one example of step 3640, the implosion rate of leukemia cells 192 is plotted as a function of frequency, and a peak fitting routine is applied to the data to determine the optimal resonance frequency. This optimal resonance frequency need not be one of the frequencies tested in step 3630 but may be in between two such frequencies.

In certain embodiments, method 3600 includes a step 3620 that precedes step 3630. Step 3620 calculates an expected, approximate resonance frequency for implosion of leukemia cells 192 based upon the size $R_0$ of leukemia cells 192. In an embodiment, step 3620 utilizes the equation $$R_0 = \frac{1}{\omega_0}\sqrt{\frac{3\kappa p_0}{\rho}},$$

wherein $\kappa$ is the polytropic index of blood 190, $p_0$ is the hydrostatic liquid pressure in blood 190 outside leukemia cell 192, $\rho$ is the density of blood 190, $\omega_0 = 2\pi f_0$, and $f_0$ is the expected, approximate resonance frequency. In this embodiment, step 3620 solves this equation for $f_0$. The polytropic index κ may be about 1.3, the hydrostatic liquid pressure $p_0$ may be about $10^6$ dynes/centimeter$^2$, and the density p may be about one gram/centimeter$^3$.

In embodiments of method 3600 that include step 3620, step 3630 may implement a step 3632 of performing the frequency scan of step 3630 in a frequency range that is around or near the expected, approximate resonance frequency calculated in step 3620.

Optionally, method 3600 further includes a step 3610 that precedes step 3620. Step 3610 measures the size of leukemia cells 192 in blood 190 from patient 180. In one example of step 3610, a sample of blood 190 is extracted from patient 180 and evaluated under a microscope to determine the size of leukemia cells 192 in blood 190 from patient 180.

Figure 37:
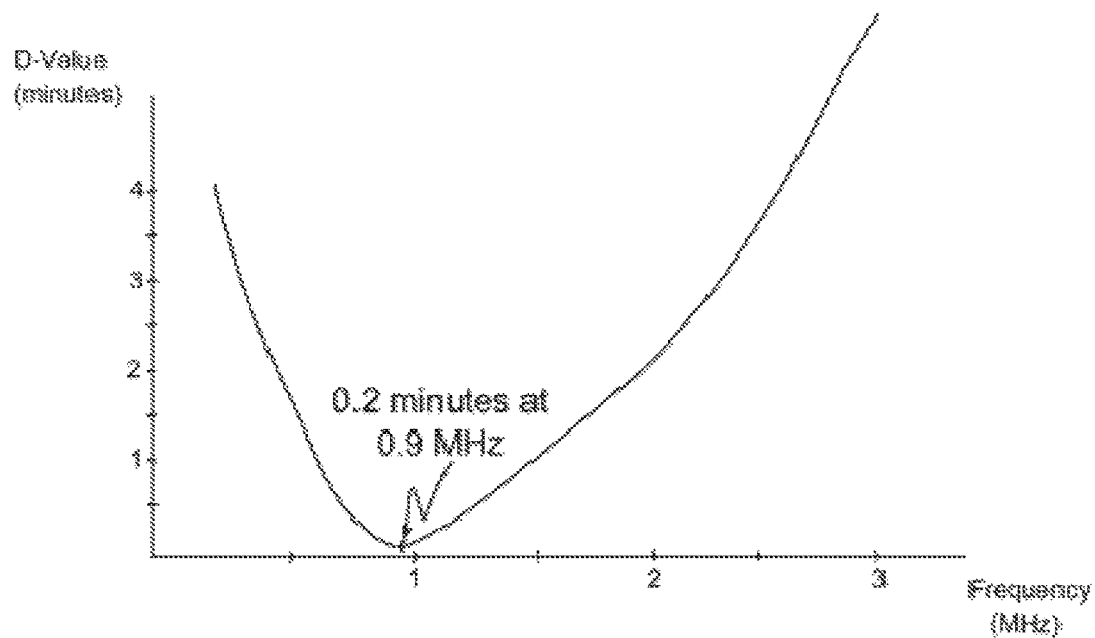
FIG. 37 shows an exemplary modeled graph produced in a D-value based embodiment of the method of FIG. 36 to determine an optimal resonance frequency for implosion of leukemia cells.

FIG. 37 shows one exemplary modeled graph produced in a D-value based embodiment of step 3630 of method 3600 to determine the optimal resonance frequency for implosion of leukemia cells 192. For each sample of blood 190 used, step 3630 measures the D-value for the frequency applied to the sample, i.e., the time required to implode leukemia cells 192 in the sample. FIG. 37 shows exemplary D-values obtained for a plurality of frequencies of sound energy 140 in the range from about 300 kHz to about 3 MHz. The frequency axis shown in FIG. 37 represents center frequency 352 if step 3630 utilizes frequency sweeping.

Step 3640 deduces the optimal resonance frequency for implosion of leukemia cells 192 from the graph of FIG. 37 as the frequency associated with the minimum D-value. Thus, according to the data of FIG. 37, the optimal resonance frequency is about 0.9 MHz.

In an exemplary scenario, step 610 of method 600 may, based upon the data of FIG. 37, expose blood 190 to sound energy that is about 0.9 MHz. If step 616 is implemented in this scenario, step 610 of method 600 may expose blood 190 to sound energy with a frequency that is repeatedly swept about a center frequency 352 of 0.9 MHz with a frequency bandwidth 354 that is in the range between 0.1 percent and 7 percent of 0.9 MHz. For example, step 610 may repeatedly sweep the frequency of the sound energy between 0.89 MHz and 0.91 MH, between 0.87 MHz and 0.93 MHz, or between 0.8996 MHz and 0.9005 MHz, for example.

Figure 38:
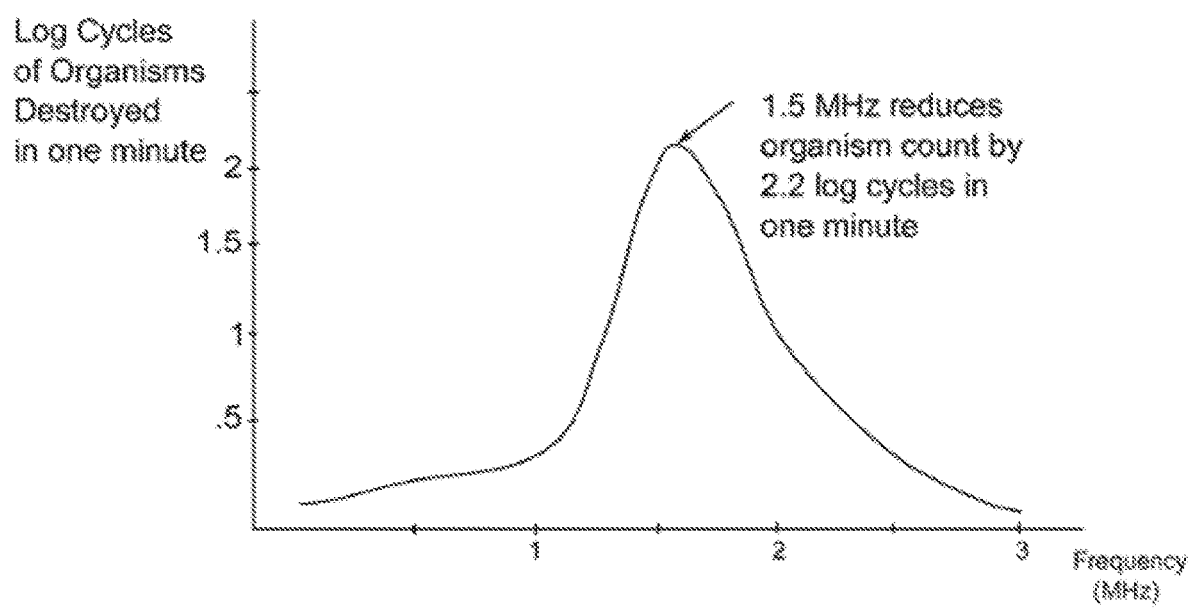
FIG. 38 shows an exemplary modeled graph produced in a culture-based embodiment of the method of FIG. 36 to determine an optimal resonance frequency for implosion of leukemia cells.

FIG. 38 shows one exemplary modeled graph produced in a culture-based embodiment of step 3630 of method 3600 to determine the optimal resonance frequency for implosion of organisms such as leukemia cells 192. For the same number of test frequencies, fewer measurements are required to obtain the data of FIG. 38, as compared to the data of FIG. 37. For each sample of blood 190 used, step 3630 measures an initial organism count, e.g., an initial count of leukemia cells 192. Next, step 3630 exposes the sample of blood 190 to sound energy 140 at the associated test frequency for a fixed period of time that is the same for all samples of blood 190 (for example one minute). After this exposure to sound energy, the sample is cultured to determine the number of log cycles reduction in organism count. The number of log cycles reduction is found as the log to the base 10 of the ratio of the initial count to the post-exposure count. The frequency axis shown in FIG. 38 represents center frequency 352 if step 3630 utilizes frequency sweeping.

Step 3640 deduces the optimal resonance frequency for implosion of leukemia cells 192 from the graph of FIG. 38 as the frequency associated with the maximum number of log cycles reduction. Thus, according to the data of FIG. 38, the optimal resonance frequency is about 1.5 MHz.

In an exemplary scenario, step 610 of method 600 may, based upon the data of FIG. 38, expose blood 190 to sound energy that is about 1.5 MHz. If step 616 is implemented in this scenario, step 610 of method 600 may expose blood 190 to sound energy with a frequency that is repeatedly swept about a center frequency 352 of 1.5 MHz with a frequency bandwidth 354 that is in the range between 0.1 percent and 7 percent of 0.9 MHz. For example, step 610 may repeatedly sweep the frequency of the sound energy between 1.49 MHz and 1.51 MHz, between 1.45 MHz and 1.55 MHz, or between 1.499 MHz and 1.501 MHz, for example.

The systems and methods disclosed herein for imploding leukemia cells 192 in blood 190 of patient 180 may be extended to implosion of other organisms in blood 190, such as other cells circulating in patient 180 with blood 190, without departing from the scope hereof. This extension to implosion of other organisms may include adapting transducers 120 to generate sound energy 140 at a frequency resonant with the implosion of such organisms. Furthermore, the presently disclosed systems and methods may be extended to implosion of organisms in other liquid media than blood, such as lymphatic fluid or a non-human derived fluid.

In addition, the mechanisms disclosed herein for disruption of the coherence of beams 340 to disperse sound energy 140 to the entire volume of blood 190 within vessel 110 may be applied in the fields of megasonic and ultrasonic cleaning. In one example, vessel 110 is at least partly filled with a suitable cleaning liquid and an object to be cleaned is immersed in this cleaning liquid. Transducers 120 generate sound energy 140 that, by virtue of the dispersion mechanisms disclosed herein, is dispersed to the entire volume of the cleaning liquid inside vessel 110, resulting in efficient cleaning of the object immersed in the cleaning liquid.

In an embodiment, the systems and methods disclosed in FIGS. 1-38 are adapted for non-implosion destruction of leukemia cells 192. In general, when leukemia cells 192 absorb sound energy 140, leukemia cells 192 may undergo stable or transient cavitation. In stable cavitation, a leukemia cell 192 vibrates in resonance with sound energy 140, and system 100, through the forces associated with this vibration, causes damage sufficient to destroy, at least to a certain degree, such a leukemia cell 192. For example, stable cavitation may break the cell's reproductive capabilities. In transient cavitation, a leukemia cell 192 vibrates in resonance with sound energy 140, and the forces thus applied by system 100 are so strong that this leukemia cell 192 implodes and is broken into fragments 194. Thus, transient cavitation of a leukemia cell 192 results in destruction of this leukemia cell 192 by implosion as discussed above in reference to FIG. 1 for example. Destruction of leukemia cell 192 through stable cavitation may not require as high a power-level of sound energy 140 as needed to implode leukemia cells 192.

Combinations of Features

Features described above as well as those claimed below may be combined in various ways without departing from the scope hereof. For example, it will be appreciated that aspects of one system or method for imploding leukemia cells of a patient, described herein may, incorporate or swap features of another system or method for imploding leukemia cells of a patient described herein. The following examples illustrate some possible, non-limiting combinations of embodiments described above. It should be clear that many other changes and modifications may be made to the systems herein without departing from the spirit and scope of this invention:

(A1) A system for imploding leukemia cells of a patient may include a first vessel for containing a volume of blood received from the patient, and drive circuitry cooperatively coupled with at least one transducer to produce ultrasound energy that spatially decoheres and disperses throughout the volume, to implode the leukemia cells throughout the volume via absorption of the ultrasound energy by the leukemia cells.

(A2) In the system denoted as (A1), the ultrasound energy may have frequency in range from 20 kilohertz to 15 megahertz.

(A3) In either or both of the systems denoted as (A1) and (A2), the first vessel may include an inlet for receiving the blood from the patient, and an outlet for delivering the blood back to the patient after exposure to the ultrasound energy within the first vessel, wherein the outlet is spaced apart from the inlet to define a flow path of the blood through the first vessel.

(A4) In any of the systems denoted as (A1) through (A3), the at least one transducer may include a plurality of transducers coupled to the first vessel in a plurality of locations.

(A5) In any of the systems denoted as (A1) through (A4), each transducer may be mounted to a wall of the first vessel to direct the ultrasound energy into the blood in a direction substantially orthogonal to the wall.

(A6) In either or both of the systems denoted as (A4) and (A5), the at least one transducer may include a first transducer configured to direct first ultrasound energy into the blood along a first direction, and a second transducer configured to direct second ultrasound energy into the blood along a second direction that is different from the first direction, such that the second ultrasound energy spatially overlaps with the first ultrasound energy to decohere and disperse ultrasound energy throughout volume.

(A7) In the system denoted as (A6), the drive circuitry may be configured to drive the first transducer out of phase with the second transducer, to improve efficiency of decoherence and dispersion of the ultrasound energy.

(A8) In either or both of the systems denoted as (A6) and (A7), the drive circuitry may include a generator for generating a drive signal, wherein the generator is coupled to the first transducer and the second transducer with mutually opposite polarity, so as to drive the first transducer out of phase with the second transducer.

(A9) In any of the systems denoted as (A6) through (A8), the drive circuitry may be configured to drive the first transducer and the second transducer at same frequency.

(A10) In any of the systems denoted as (A6) through (A8), the drive circuitry may include a first generator coupled with the first transducer for generating the first ultrasound energy with a first frequency, and a second generator coupled with the second transducer for generating the second ultrasound energy with a second frequency different from the first frequency, to facilitate decoherence and dispersion of the ultrasound energy.

(A11) In any of the systems denoted as (A1) through (A4), the transducers may include a first transducer configured to direct first ultrasound energy into the blood along a first direction, and a second transducer configured to direct second ultrasound energy into the blood along a second direction that is parallel with the first direction, wherein a distance between the first transducer and the second transducer is sufficiently small to introduce coupling between the first ultrasound energy and the second ultrasound energy such that, when the second ultrasound energy differs from the first ultrasound energy in at least one of phase and frequency, the ultrasound energy decoheres and disperses throughout volume.

(A12) In the system denoted as (A11), the drive circuitry may be configured to drive the first transducer out of phase with the second transducer to decohere and disperse the ultrasound energy throughout the volume.

(A13) In either or both of the systems denoted as (A11) and (A12), the drive circuitry may include a generator for generating a drive signal, wherein the generator is coupled to the first transducer and the second transducer with mutually opposite polarity, so as to drive the first transducer out of phase with the second transducer.

(A14) In any of the systems denoted as (A11) through (A13), the drive circuitry may be configured to drive the first transducer and the second transducer at same frequency.

(A15) In any of the systems denoted as (A11) through (A13), the drive circuitry may include a first generator coupled with the first transducer for generating the first ultrasound energy with a first frequency, and a second generator coupled with the second transducer for generating the second ultrasound energy with a second frequency different from the first frequency to decohere and disperse the ultrasound energy throughout the volume.

(A16) In any of the systems denoted as (A1) through (A3), each transducer may be an immersible transducer configured to be immersed in the blood within the first vessel to generate ultrasound energy propagating, through the blood, away from the immersible transducer in two opposite directions.

(A17) In the system denoted as (A16), the at least one transducer may include a first transducer configured to direct first ultrasound energy into the blood along a first direction, and a second transducer configured to direct second ultrasound energy into the blood along a second direction that is different from the first direction such that the second ultrasound energy spatially overlaps with the first ultrasound energy to decohere and disperse ultrasound energy throughout volume.

(A18) In the system denoted as (A17), the drive circuitry may be configured to drive the first transducer out of phase with the second transducer to improve efficiency of decoherence and dispersion of the ultrasound energy.

(A19) In either or both of the systems denoted as (A17) and (A18), the drive circuitry may include a generator for generating a drive signal, wherein the generator is coupled to the first transducer and the second transducer with mutually opposite polarity, so as to drive the first transducer out of phase with the second transducer.

(A20) In any of the systems denoted as (A17) through (A19), the drive circuitry may be configured to drive the first transducer and the second transducer at same frequency.

(A21) In any of the systems denoted as (A17) through (A19), the drive circuitry may include a first generator coupled with the first transducer for generating the first ultrasound energy with a first frequency, and a second generator coupled with the second transducer for generating the second ultrasound energy with a second frequency different from the first frequency to improve efficiency of decoherence and dispersion of the ultrasound energy.

(A22) In any of the systems denoted as (A1) through (A21), the drive circuitry and the at least one transducer may be cooperatively configured to (a) repeatedly sweep the ultrasound energy generated by each of the at least one transducer about a center frequency and across a frequency bandwidth to decohere and disperse the ultrasound energy to entire volume of the blood in the first vessel.

(A23) In the system denoted as (A22), the frequency bandwidth may be in the range between 0.1 percent and 15 percent of the center frequency.

(A24) In either or both of the systems denoted as (A21) and (A22), the center frequency may be between 20 kilohertz and 15 megahertz.

(A25) Any of the systems denoted as (A1) through (A24) may further include a second vessel for containing a liquid, wherein the at least one transducer is cooperatively configured to deliver the ultrasound energy to the liquid and decohere and disperse the ultrasound energy throughout entire volume of the liquid, such that the first vessel, when placed in contact with the liquid, transmits the ultrasound energy to the entire volume of blood within the first vessel.

(B1) A system for imploding leukemia cells of a patient may include a vessel for containing a volume of blood received from the patient, and drive circuitry cooperatively coupled with at least one immersible transducer, each immersible transducer being configured to be immersed in blood within the vessel, to produce ultrasound energy that spatially decoheres and disperses throughout the volume and implodes leukemia cells throughout the volume via absorption of the ultrasound energy by the leukemia cells.

(B2) In the system denoted as (B1), each immersible transducer may be configured to emit ultrasound energy into the blood in two opposite directions away from the immersible transducer.

(B3) In either or both of the systems denoted as (B1) and (B2), each immersible transducer may be a disposable transducer configured for single use.

(B4) In any of the systems denoted as (B1) through (B3), the drive circuitry and the at least one immersible transducer may be cooperatively configured to repeatedly sweep the ultrasound energy generated by each immersible transducer about a center frequency and across a frequency bandwidth to spatially decohere and disperse the ultrasound energy to entire volume of the blood in the vessel.

(B5) In the system denoted as (B4), the frequency bandwidth may be in the range between 0.1 percent and 15 percent of the center frequency.

(B6) In either or both of the systems denoted as (B4) and (B5), the center frequency may be between 20 kilohertz and 15 megahertz.

(B7) In any of the systems denoted as (B1) through (B6), the at least one immersible transducer may include (a) a first immersible transducer configured to direct first ultrasound energy into the blood along a first direction, and (b) a second immersible transducer configured to direct second ultrasound energy into the blood along a second direction that is different from the first direction such that the second ultrasound energy spatially overlaps with the first ultrasound energy to spatially decohere and disperse ultrasound energy throughout volume.

(B8) In the system denoted as (B7), the drive circuitry may be configured to drive the first immersible transducer out of phase with the second transducer to improve efficiency of spatial decoherence and dispersion of the ultrasound energy.

(B9) In either or both of the systems denoted as (B7) and (B8), the drive circuitry may include a generator for generating a drive signal, wherein the generator is coupled to the first immersible transducer and the second immersible transducer with mutually opposite polarity, so as to drive the first immersible transducer out of phase with the second immersible transducer.

(B10) In any of the systems denoted as (B7) through (B9), the drive circuitry may include (a) a first generator coupled with the first immersible transducer for generating the first ultrasound energy with a first frequency, and (b) a second generator coupled with the second immersible transducer for generating the second ultrasound energy with a second frequency different from the first frequency to improve efficiency of spatial decoherence and dispersion of the ultrasound energy.

(B11) In any of the systems denoted as (B7) through (B9), the drive circuitry may be configured to drive the first immersible transducer and the second immersible transducer at same frequency.

(C1) A system for imploding leukemia cells of a patient may include (a) an outer vessel for containing a liquid permitting spatial decoherence and dispersion of ultrasound energy delivered to the liquid, (b) at least one transducer coupled to an outer surface of the outer vessel, (c) drive circuitry cooperatively coupled with the transducer to produce ultrasound energy that spatially decoheres and disperses as incoherent ultrasound energy throughout the liquid, (d) an inner vessel having an inlet for receiving blood, an outlet for removing the blood, and a plurality of baffles configured to extend flow path of the blood between the inlet and the outlet, and (e) a pump for circulating blood out of the patient through the inner vessel, via the inlet and the outlet, and back to the patient, wherein, when the blood passes through the inner vessel and the inner vessel is in contact with the liquid, the leukemia cells in the blood are imploded via absorption of a portion of the incoherent ultrasound transmitted from the liquid to the blood and dispersed throughout the blood within the inner vessel.

(C2) The system denoted as (C1) may further include a first catheter for extracting the blood from the patient to be circulated through the inner vessel by the pump, and a second catheter for delivering the blood back to the patient after passing through the inner vessel.

(C3) In either or both of the systems denoted as (C1) and (C2), the inner vessel may be nested within the outer vessel.

(C4) In the system denoted as (C3), each of the inner vessel and the outer vessel may have shape of an elongated prism with three sidewalls parallel to axis of elongation, wherein each of the three sidewalls is coupled with a different one of the at least one transducer.

(C5) In the system denoted as (C4), each of the sidewalls may include a plurality of sections of different respective wall thicknesses to efficiently transmit ultrasound energy generated by a respective plurality of transducers and of different respective frequencies.

(C6) In any of the systems denoted as (C1) through (C5), the inner vessel may be a disposable container configured for single use.

(C7) In any of the systems denoted as (C1) through (C5), the inner vessel may be a reusable container compatible with steam sterilization.

(D1) A method for imploding leukemia cells of a patient may include circulating blood from a patient through an external vessel while generating incoherent ultrasound energy throughout entire volume of blood within the external vessel to implode the leukemia cells throughout the entire volume via absorption of the ultrasound energy by the leukemia cells.

(D2) In the method denoted as (D1), the step of generating may include producing at least one ultrasound energy beam such that coherence of the ultrasound energy beam is disrupted to generate the incoherent ultrasound energy.

(D3) In the method denoted as (D2), the step of producing may include producing each ultrasound energy beam with frequency in range from 20 kilohertz to 15 megahertz.

(D4) In either or both of the methods denoted as (D2) and (D3), the step of generating may include intercoupling at least two ultrasound energy beams to spatially decohere and disperse ultrasound energy of the ultrasound energy beams to the entire volume.

(D5) In the method denoted as (D4), the step of intercoupling may include directing the ultrasound energy beams along different directions to spatially overlap the ultrasound energy beams, to spatially decohere and disperse ultrasound energy of the ultrasound energy beams to the entire volume (D6) In either or both of the methods denoted as (D4) and (D5), the step of intercoupling may include producing the ultrasound energy beams using different respective transducers operating at different respective frequencies, to spatially decohere and disperse ultrasound energy of the ultrasound energy beams to the entire volume.

(D7) In any of the methods denoted as (D4) through (D6), the step of intercoupling may include producing the ultrasound energy beams using different respective transducers operating at different respective phases, to spatially decohere and disperse ultrasound energy of the ultrasound energy beams to the entire volume.

(D8) In the method denoted as (D7), the ultrasound energy beams may consist of two ultrasound energy beams, and the step of producing the ultrasound energy beams may include driving two transducers, coupled at mutually opposite polarity to common drive circuitry, to respectively generate the two ultrasound energy beams with mutually opposite phase.

(D9) In the method denoted as (D4), the ultrasound energy beams may include first and second ultrasound energy beams, and the step of intercoupling may include directing the first and second ultrasound energy beams in parallel directions with distance between the first and second ultrasound energy beams being sufficiently small to introduce coupling between the first and second ultrasound beams, so as to spatially decohere and disperse ultrasound energy of the first and second ultrasound energy beams to the entire volume.

(D10) In the method denoted as (D9), the step of intercoupling may include producing the first and second ultrasound energy beams using different respective transducers operating at different respective frequencies, to spatially decohere and disperse ultrasound energy of the first and second ultrasound energy beams to the entire volume.

(D11) In either or both of the methods denoted as (D9) and (D10), the step of intercoupling may include producing the first and second ultrasound energy beams using different respective transducers operating at different respective phases, to spatially decohere and disperse ultrasound energy of the first and second ultrasound energy beams to the entire volume.

(D12) In the method denoted as (D11), the step of producing may include driving two transducers, coupled at mutually opposite polarity to common drive circuitry, to respectively produce the first and second ultrasound energy beams with mutually opposite phase.

(D13) In any of the methods denoted as (D2) through (D12), the step of generating may include repeatedly sweeping frequency of each ultrasound energy beam about a center frequency and across a frequency bandwidth to spatially decohere and disperse ultrasound energy of each ultrasound energy beam to entire volume.

(D14) In the method denoted as (D13), in the step of repeatedly sweeping, the frequency bandwidth may be in the range between 0.1 percent and 15 percent of the center frequency.

(D15) In either or both of the methods denoted as (D13) and (D14), the center frequency may be between 20 kilohertz and 15 megahertz.

(D16) In the method denoted as (D2), the at least one ultrasound energy beam may consist of a single ultrasound energy beam, and the step of generating may include repeatedly sweeping frequency of the single ultrasound energy beam about a center frequency and across a frequency bandwidth to spatially decohere and disperse ultrasound energy of the single ultrasound energy beam to entire volume.

(D17) In any of the methods denoted as (D2) through (D16), the step of generating may include producing each ultrasound energy beam using a respective transducer coupled to a wall of the external vessel.

(D18) In any of the methods denoted as (D2) through (D16), the at least one ultrasound energy beam may include at least one pair of ultrasound energy beams, and the step of generating may include generating each pair of ultrasound energy beams using a respective immersible transducer immersed in the blood.

(D19) In the method denoted as (D18), the step of generating may include, for each pair of ultrasound energy beams, directing the pair of ultrasound energy beams away from the respective immersible transducer in two opposite directions.

(D20) In any of the methods denoted as (D10) through (D19), the step of circulating may include extracting the blood from the patient via a first catheter, passing the blood through the external vessel, and returning the blood to the patient via a second catheter.

(D21) In any of the methods denoted as (D10) through (D20), the step of circulating may include pumping the blood through the external vessel.

(E1) A method for imploding leukemia cells of a patient may include generating spatially incoherent ultrasound energy throughout a liquid held in a first vessel external to the patient, and exposing blood within a second vessel in contact with the liquid to at least a portion of the incoherent ultrasound energy transmitted from the liquid to the blood and dispersed to entire volume of blood in the second vessel, to implode the leukemia cells throughout the entire volume via absorption of the ultrasound energy by the leukemia cells.

(E2) The method denoted as (E1) may further include conditioning the liquid for efficient spatial decoherence and dispersion of ultrasound energy.

(E3) In the method denoted as (E2), the step of conditioning may include raising temperature of the liquid to above room temperature.

(E4) In the method denoted as (E3), the step of raising may include raising temperature of the liquid to range from 100 and 150 degrees Fahrenheit.

(E5) In any of the methods denoted as (E2) through (E4), the step of conditioning may include degassing the liquid.

(E6) In any of the methods denoted as (E1) through (E5), the step of generating may include generating the spatially incoherent ultrasound energy with frequency in range from 20 kilohertz to 15 megahertz.

(E7) In any of the methods denoted as (E1) through (E6), the step of generating may include intercoupling at least two ultrasound energy beams within the liquid to spatially decohere and disperse ultrasound energy of the ultrasound energy beams to entire volume of the liquid.

(E8) In the method denoted as (E7), the step of intercoupling may include directing the ultrasound energy beams along different directions to spatially overlap the ultrasound energy beams, to spatially decohere and disperse ultrasound energy of the ultrasound energy beams to the entire volume of the liquid.

(E9) In either or both of the methods denoted as (E7) and (E8), the step of intercoupling may include producing the ultrasound energy beams using different respective transducers operating at different respective frequencies, to spatially decohere and disperse ultrasound energy of the ultrasound energy beams to the entire volume of the liquid.

(E10) In any of the methods denoted as (E7) through (E9), the step of may include comprising producing the ultrasound energy beams using different respective transducers operating at different respective phases, to spatially decohere and disperse ultrasound energy of the ultrasound energy beams to the entire volume of the liquid.

(E11) In the method denoted as (E10), the ultrasound energy beams may consist of two ultrasound energy beams, and the step of producing may include driving two transducers, coupled at mutually opposite polarity to common drive circuitry, to respectively generate the two ultrasound energy beams with mutually opposite phase.

(E12) In the method denoted as (E7), the ultrasound energy beams may include first and second ultrasound energy beams, and the step of intercoupling may include directing the first and second ultrasound energy beams in parallel directions with distance between the first and second ultrasound energy beams being sufficiently small to introduce coupling between the first and second ultrasound beams, to spatially decohere and disperse ultrasound energy of the first and second ultrasound energy beams to the entire volume of the liquid.

(E13) In the method denoted as (E12), the step of intercoupling may include producing the first and second ultrasound energy beams using different respective transducers operating at different respective frequencies, to spatially decohere and disperse ultrasound energy of the first and second ultrasound energy beams to the entire volume of the liquid.

(E14) In either or both of the methods denoted as (E12) and (E13), the step of intercoupling may include producing the first and second ultrasound energy beams using different respective transducers operating at different respective phases, to spatially decohere and disperse ultrasound energy of the first and second ultrasound energy beams to the entire volume of the liquid.

(E15) In the method denoted as (E14), the step of producing may include driving two transducers, coupled at mutually opposite polarity to common drive circuitry, to respectively generate the first and second ultrasound energy beams with mutually opposite phase.

(E16) In any of the methods denoted as (E1) through (E15), the step of generating may include repeatedly sweeping frequency of at least one ultrasound energy beam, directed into the liquid, about a center frequency and across a frequency bandwidth to spatially decohere and disperse ultrasound energy of each ultrasound energy beam to the entire volume of the liquid.

(E17) In the method denoted as (E1), the step of generating may include repeatedly sweeping frequency of a single ultrasound energy beam about a center frequency and across a frequency bandwidth to spatially decohere and disperse ultrasound energy of the single ultrasound energy beam to entire volume.

(E18) In either or both of the methods denoted as (E16) and (E17), in the step of repeatedly sweeping, the frequency bandwidth may be in range between 0.1 percent and 15 percent of the center frequency.

(E19) In any of the methods denoted as (E16) through (E18), the center frequency may be between 20 kilohertz and 15 megahertz.

(E20) In any of the methods denoted as (E1) through (E19), the step of generating may include producing the incoherent ultrasound energy using at least one transducer coupled to a wall of the first vessel.

(E21) In any of the methods denoted as (E1) through (E19), the step of generating may include generating the incoherent ultrasound energy using at least one immersible transducer immersed in the liquid.

(E22) In the method denoted as (E21), the step of generating may include directing two ultrasound energy beams away from each immersible transducer in two opposite directions, respectively.

(E23) Any of the methods denoted as (E1) through (E22) may further include circulating the blood from the patient through the vessel.

(E24) In the method denoted as (E23), the step of circulating may include extracting the blood from the patient via a first catheter, passing the blood through the vessel, and returning the blood to the patient via a second catheter.

(E25) In either or both of the methods denoted as (E23) and (E24), the step of circulating comprising pumping the blood through the vessel.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present systems and methods, which, as a matter of language, might be said to fall therebetween.

What is claimed is:

1. A system for imploding leukemia cells of a patient, comprising:
   a vessel for containing a volume of blood received from the patient;
   a first transducer coupled to the vessel at a first location to direct first ultrasound energy into the volume of blood along a first direction;
   a second transducer coupled to the vessel at a second location to direct second ultrasound energy into the volume of blood along a second direction that is parallel to the first direction, a distance between the first and second locations being selected to introduce coupling between the first and second ultrasound energies; and
   drive circuitry cooperatively coupled with the first and second transducers and configured to drive the first transducer out of phase with the second transducer such that the first ultrasound energy is out of phase with the second ultrasound energy;
   wherein the first and second ultrasound energies spatially decohere and disperse throughout the volume of blood to implode the leukemia cells in the volume of blood via absorption of the first and second ultrasound energies.

2. The system of claim 1, the drive circuitry being configured to drive the first transducer and the second transducer at a same frequency.

3. The system of claim 1, the drive circuitry comprising a generator for generating a drive signal, the generator being coupled to the first transducer and the second transducer with opposite polarity to drive the first transducer out of phase with the second transducer.

4. A system for imploding leukemia cells of a patient, comprising:
- a vessel for containing a volume of blood received from the patient;
- a first transducer coupled to the vessel at a first location to direct first ultrasound energy into the volume of blood along a first direction;
- a second transducer coupled to the vessel at a second location to direct second ultrasound energy into the volume of blood along a second direction that is parallel to the first direction, a distance between the first and second locations being selected to introduce coupling between the first and second ultrasound energies;
- a first generator cooperatively coupled with the first transducer to drive the first transducer at a first frequency; and
- a second generator cooperatively coupled with the second transducer to drive the second transducer at a second frequency different from the first frequency;
- wherein the first and second ultrasound energies spatially decohere and disperse throughout the volume of blood to implode the leukemia cells in the volume of blood via absorption of the first and second ultrasound energies.

* * * * *